US008062871B2

(12) United States Patent
Burgard et al.

(10) Patent No.: US 8,062,871 B2
(45) Date of Patent: *Nov. 22, 2011

(54) MICROORGANISMS FOR THE PRODUCTION OF ADIPIC ACID AND OTHER COMPOUNDS

(75) Inventors: Anthony P. Burgard, Bellefonte, PA (US); Priti Pharkya, San Diego, CA (US); Robin E. Osterhout, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/088,256

(22) Filed: Apr. 15, 2011

(65) Prior Publication Data

US 2011/0195466 A1 Aug. 11, 2011

Related U.S. Application Data

(63) Continuation of application No. 12/875,084, filed on Sep. 2, 2010, which is a continuation of application No. 12/413,355, filed on Mar. 27, 2009, now Pat. No. 7,799,545.

(60) Provisional application No. 61/040,059, filed on Mar. 27, 2008.

(51) Int. Cl.
*C12P 7/62* (2006.01)
*C12P 7/44* (2006.01)
(52) U.S. Cl. .................. 435/135; 435/136; 435/142
(58) Field of Classification Search .................. None
See application file for complete search history.

(56) References Cited

U.S. PATENT DOCUMENTS

| | | | |
|---|---|---|---|
| 3,513,209 A | 5/1970 | Clement | |
| 3,912,586 A | 10/1975 | Kaneyuki et al. | |
| 3,965,182 A | 6/1976 | Worrel | |
| 4,048,196 A | 9/1977 | Broecker et al. | |
| 4,082,788 A | 4/1978 | Mims | |
| 4,190,495 A | 2/1980 | Curtiss | |
| 4,301,077 A | 11/1981 | Pesa et al. | |
| 4,624,920 A | 11/1986 | Inoue et al. | |
| 4,652,685 A | 3/1987 | Cawse et al. | |
| 4,871,667 A | 10/1989 | Imada et al. | |
| 5,079,143 A | 1/1992 | Klein et al. | |
| 5,143,833 A | 9/1992 | Datta | |
| 5,143,834 A | 9/1992 | Glassner et al. | |
| 5,168,055 A | 12/1992 | Datta et al. | |
| 5,173,429 A | 12/1992 | Gaddy et al. | |
| 5,182,199 A | 1/1993 | Hartley | |
| 5,192,673 A | 3/1993 | Jain et al. | |
| 5,403,721 A | 4/1995 | Ward, Jr. et al. | |
| 5,413,922 A | 5/1995 | Matsuyama et al. | |
| 5,416,020 A | 5/1995 | Severson et al. | |
| 5,457,040 A | 10/1995 | Jarry et al. | |
| 5,478,952 A | 12/1995 | Schwartz | |
| 5,487,987 A | 1/1996 | Frost et al. | |
| 5,504,004 A | 4/1996 | Guettler et al. | |
| 5,512,465 A | 4/1996 | Matsuyama et al. |
| 5,521,075 A | 5/1996 | Guettler et al. |
| 5,573,931 A | 11/1996 | Guettler et al. |
| 5,616,496 A | 4/1997 | Frost et al. |
| 5,686,276 A | 11/1997 | Lafend et al. |
| 5,700,934 A | 12/1997 | Wolters et al. |
| 5,770,435 A | 6/1998 | Donnelly et al. |
| 5,807,722 A | 9/1998 | Gaddy et al. |
| 5,869,301 A | 2/1999 | Nghiem et al. |
| 5,908,924 A | 6/1999 | Burdette et al. |
| 5,958,745 A | 9/1999 | Gruys et al. |
| 6,117,658 A | 9/2000 | Dennis et al. |
| 6,133,014 A | 10/2000 | Mukouyama et al. |
| 6,136,577 A | 10/2000 | Gaddy et al. |
| 6,159,738 A | 12/2000 | Donnelly et al. |
| 6,194,572 B1 | 2/2001 | Buijs et al. |
| 6,214,592 B1 | 4/2001 | Crouzet et al. |
| 6,274,790 B1 | 8/2001 | Kunst et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,353,100 B1 | 3/2002 | Guit et al. |
| 6,432,686 B1 | 8/2002 | Bulthuis et al. |
| 6,448,061 B1 | 9/2002 | Pan et al. |

(Continued)

FOREIGN PATENT DOCUMENTS

CN 1 358 841 7/2002

(Continued)

OTHER PUBLICATIONS

Parke et al. Cloning and genetic characterization of dca genes required for beta-oxidation of straight-chain dicarboxylic acids in *Actinobacter* sp. strain ADP1. Appl. Envirn. Microbiol. Oct. 2001, 67 (10) 4817-4827.*
Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).
Abe et al., "Discovery of amide (peptide) bond synthetic activity in Acyl-CoA synthetase," *J. Biol. Chem.* 283(17):11312-11321 (2008).
Aberhart and Hsu, "Stereospecific hydrogen loss in the conversion of [²H₇] isobutyrate to β-hydroxyisobutyrate in *Pseudomonas putida*. The stereochemistry of β-hydroxyisobutyrate dehydrogenase," *J. Chem. Soc.* [Perkin1] 6:1404-1406 (1979).
Abiko et al., "Localization of NAD-isocitrate dehydrogenase and glutamate dehydrogenase in rice roots: candidates for providing carbon skeletons to NADH-glutamate synthase," *Plant Cell Physiol.* 46:1724-1734 (2005).

(Continued)

*Primary Examiner* — Nashaat Nashed
(74) *Attorney, Agent, or Firm* — Jones Day

(57) ABSTRACT

The invention provides a non-naturally occurring microbial organism having an adipate, 6-aminocaproic acid or caprolactam pathway. The microbial organism contains at least one exogenous nucleic acid encoding an enzyme in the respective adipate, 6-aminocaproic acid or caprolactam pathway. The invention additionally provides a method for producing adipate, 6-aminocaproic acid or caprolactam. The method can include culturing an adipate, 6-aminocaproic acid or caprolactam producing microbial organism, where the microbial organism expresses at least one exogenous nucleic acid encoding an adipate, 6-aminocaproic acid or caprolactam pathway enzyme in a sufficient amount to produce the respective product, under conditions and for a sufficient period of time to produce adipate, 6-aminocaproic acid or caprolactam.

12 Claims, 9 Drawing Sheets

U.S. PATENT DOCUMENTS

| | | |
|---|---|---|
| 6,455,284 B1 | 9/2002 | Gokarn et al. |
| 6,485,947 B1 | 11/2002 | Rajgarhia et al. |
| 6,660,857 B2 | 12/2003 | Agterberg et al. |
| 6,686,194 B1 | 2/2004 | Mutzel et al. |
| 6,686,310 B1 | 2/2004 | Kourtakis et al. |
| 6,743,610 B2 | 6/2004 | Donnelly et al. |
| 6,852,517 B1 | 2/2005 | Suthers et al. |
| 7,127,379 B2 | 10/2006 | Palsson et al. |
| 7,186,541 B2 | 3/2007 | Gokarn et al. |
| 7,223,567 B2 | 5/2007 | Ka-Yiu et al. |
| 7,241,594 B2 | 7/2007 | Lee et al. |
| 7,244,610 B2 | 7/2007 | San et al. |
| 7,256,016 B2 | 8/2007 | San et al. |
| 7,262,046 B2 | 8/2007 | Ka-Yiu et al. |
| 7,285,402 B2 | 10/2007 | Gaddy et al. |
| 7,309,597 B2 | 12/2007 | Liao et al. |
| 7,371,558 B2 | 5/2008 | Cervin et al. |
| 7,393,676 B2 | 7/2008 | Gorkarn et al. |
| 7,432,091 B2 | 10/2008 | Yukawa et al. |
| 7,491,520 B2 | 2/2009 | Raemakers-Franken et al. |
| 7,569,380 B2 | 8/2009 | San et al. |
| 2002/0012939 A1 | 1/2002 | Palsson |
| 2002/0040123 A1 | 4/2002 | Patil et al. |
| 2002/0106358 A1 | 8/2002 | Hopwood et al. |
| 2002/0168654 A1 | 11/2002 | Maranas et al. |
| 2003/0028915 A1 | 2/2003 | Tilton et al. |
| 2003/0032153 A1 | 2/2003 | Yamamoto et al. |
| 2003/0059792 A1 | 3/2003 | Palsson et al. |
| 2003/0087381 A1 | 5/2003 | Gokarn |
| 2003/0113886 A1 | 6/2003 | Brzostowicz et al. |
| 2003/0182678 A1 | 9/2003 | Mitsky et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0152159 A1 | 8/2004 | Causey et al. |
| 2005/0042736 A1 | 2/2005 | San et al. |
| 2005/0079482 A1 | 4/2005 | Maranas et al. |
| 2005/0250135 A1 | 11/2005 | Klaenhammer et al. |
| 2005/0287655 A1 | 12/2005 | Tabata et al. |
| 2006/0035348 A1 | 2/2006 | Gulevich et al. |
| 2006/0073577 A1 | 4/2006 | Ka-Yiu et al. |
| 2006/0099578 A1 | 5/2006 | Wallace et al. |
| 2006/0110810 A1 | 5/2006 | Rajgarhia et al. |
| 2006/0172399 A1 | 8/2006 | Nomoto et al. |
| 2006/0281156 A1 | 12/2006 | Aoyama et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto |
| 2007/0092957 A1 | 4/2007 | Donaldson et al. |
| 2007/0111294 A1 | 5/2007 | Burgard et al. |
| 2007/0117191 A1 | 5/2007 | Kamachi et al. |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0274522 A1 | 11/2008 | Bramucci et al. |
| 2008/0293125 A1 | 11/2008 | Subbian et al. |
| 2009/0047718 A1 | 2/2009 | Blaschek et al. |
| 2009/0047719 A1 | 2/2009 | Burgard et al. |
| 2009/0068207 A1 | 3/2009 | Breitbart et al. |
| 2009/0075351 A1 | 3/2009 | Burk et al. |
| 2009/0191593 A1 | 7/2009 | Burk et al. |
| 2009/0305364 A1 | 12/2009 | Burgard et al. |
| 2010/0009419 A1 | 1/2010 | Burk et al. |
| 2010/0099925 A1 | 4/2010 | Kharas |

FOREIGN PATENT DOCUMENTS

| | | |
|---|---|---|
| EP | 0 494 078 | 7/1992 |
| EP | 1 075 482 A1 | 2/2001 |
| EP | 1 473 368 | 11/2004 |
| EP | 1 647 594 A1 | 4/2006 |
| EP | 2 017 344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 82/03854 | 11/1982 |
| WO | WO 91/13997 | 9/1991 |
| WO | WO 99/06532 | 2/1999 |
| WO | WO 99/58686 | 11/1999 |
| WO | WO 01/16346 | 3/2001 |
| WO | WO 02/42418 | 5/2002 |
| WO | WO 02/055995 | 7/2002 |
| WO | WO 02/090312 | 11/2002 |
| WO | WO 03/010322 | 2/2003 |
| WO | WO 03/106691 | 12/2003 |
| WO | WO 03/106998 | 12/2003 |
| WO | WO 2004/062763 A2 | 7/2004 |
| WO | WO 2005/026338 | 3/2005 |
| WO | WO 2005/047498 | 5/2005 |
| WO | WO 2005/068643 | 7/2005 |
| WO | WO 2006/028063 | 3/2006 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/089102 A2 | 7/2008 |
| WO | WO 2008/131286 | 10/2008 |
| WO | WO 2008/137403 | 11/2008 |
| WO | WO 2008/152016 | 12/2008 |
| WO | WO 2009/013160 A2 | 1/2009 |
| WO | WO 2009/014437 | 1/2009 |
| WO | WO 2009/023493 | 2/2009 |
| WO | WO 2009/031766 | 3/2009 |
| WO | WO 2009/049274 A2 | 4/2009 |
| WO | WO 2009/094485 A1 | 7/2009 |
| WO | WO 2009/103026 | 8/2009 |
| WO | WO 2009/111513 A1 | 9/2009 |
| WO | WO 2009/113853 | 9/2009 |
| WO | WO 2009/113855 | 9/2009 |
| WO | WO 2009/131040 | 10/2009 |

OTHER PUBLICATIONS

Abo-Dalo et al., "A novel member of the GCN5-related N-acetyltransferase superfamily from Caenorhabditis elegans preferentially catalyses the N-acetylation of thialysine [S(2-aminoethyl)-L-cysteine]," *Biochem. J.* 384:129-137 (2004).

Adams and Kletzin, "Oxidoreductase-type enzymes and redox proteins involved in fermentative metabolisms of hyperthermophilic Archaea," *Adv. Protein Chem.* 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri and Liu, "Enoyl-CoA Hydratase: Reaction, Mechanism, and Inhibition," *Bioorg. Med. Chem.* 11(1):9-20 (2003).

Ahmed and Lewis, "Fermentation of Biomass-Generated Synthesis Gas: Effects of Nitric Oxide," *Biotechol. Bioeng.* 97:1080-1086 (2007).

Ahmed et al., "Effects of biomass-generated producer gas constituents on cell growth, product distribution and hydrogenase activity of Clostridium carboxidivorans P7$^T$," *Biomass Bioenergy* 30(7):665-672 (2006).

Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).

Akatsuka et al., "The Serratia marcescens bioH gene encodes an esterase," *Gene* 302(1-2):185-192 (2003).

Akhtar and Jones, "Construction of a synthetic YdbK-dependent pyruvate:H$_2$ pathway in Escherichia coli BL21(DE3)," *Metab. Eng.* 11(3):139-147 (2009).

Alam et al., "Anaerobic Fermentation Balance of *Escherichia coli* as Observed by in Vivo Nuclear Magnetic Resonance Spectroscopy," *J. Bacteriol.* 171(11):6213-6217 (1989).
Alber et al., "3-Hydroxypropionyl-Coenzyme A synthetase from *Metallosphaera sedula*, an enzyme involved in autotrophic $CO_2$ fixation," *J. Bacteriol.* 190:1383-1389 (2008).
Alber et al., "Malonyl-Coenzyme A reductase in the modified 3-hydroxypropionate cycle for autotrophic carbon fixation in archaeal Metallosphaera and *Sulfolobus* spp.," *J. Bacteriol.* 188(24):8551-8559 (2006).
Alber et al., "Propionyl-Coenzyme A synthase from *Chloroflexus aurantiacus*, a key enzyme of the 3-hydroxypropionate cycle for autotrophic $CO_2$ fixation," *J. Biol. Chem.* 277:12137-12143 (2002).
Alber et al., "Study of an alternate glyoxylate cycle for acetate assimilation by *Rhodobacter sphaeroides*," *Mol. Microbiol.* 61(2):297-309 (2006).
Alberty, Biochemical thermodynamics. *Biochim. Biophys. Acta* 1207:1-11 (1994).
Aldor and Keasling, "Metabolic engineering of poly(3-hydroxybutyrate-co-3-hydroxyvalerate) composition in recombinant *Salmonella enterica* serovar typhimurium," *Biotechnol. Bioeng.* 76(2):108-114 (2001).
Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).
Aldrich Catalog, Sigma-Aldrich Company, Milwaukee, WI, p. 481 (2002).
Aldrich et al., "Cloning and complete nucleotide sequence determination of the catB gene encoding cis,cis-muconate lactonizing enzyme," *Gene* 52:185-195 (1987).
Alexeeva et al., "Requirement of ArcA for redox regulation in *Escherichia coli* under microaerobic but not anaerobic or aerobic conditions," *J. Bacteriol.* 185(1):204-209 (2003).
Alexson et al., "NADH-sensitive propionyl-CoA hydrolase in brown-adipose-tissue mitochondria of the rat," *Biochim. Biophys. Acta* 1005(1):13-19 (1989).
Alhapel et al., "Molecular and functional analysis of nicotinate catabolism in *Eubacterium barkeri*," *Proc. Natl. Acad. Sci. U.S.A.* 103(33):12341-12346 (2006).
Alper et al., "Construction of lycopene-overproducing *E. coli* strains by combining systematic and combinatorial gene knockout targets," *Nat. Biotechnol.* 23(5):612-616 (2005).
Alper et al., "Identifying gene targets for the metabolic engineering of lycopene biosynthesis in *Escherichi coli*," *Metab. Eng.* 7(3):155-164 (2005).
Alper et al., "Engineering yeast transcription machinery for improved ethanol tolerance and production," *Science* 314(5805):1565-1568 (2006).
Altamirano et al., "Decoupling cell growth and product formation in Chinese hamster ovary cells throguh metabolic control," *Biotechnol. Bioeng.* 76(4):351-360 (2001).
Altmiller and Wanger, "Purification and properties of dihydroxy acid dehydratase from soluble and mitochondrial fractions of *Neurospora crassa*," *Arch. Biochem. Biophys.* 138:160-170 (1970).
Amann et al., "Tightly regulated tac promoter vectors useful for the expression of unfused and fused proteins in *Escherichia coli*," *Gene* 69:301-315 (1988).
Andersen and Hansen, "Cloning of the lysA gene from Mycobacterium tuberculosis," *Gene* 124(1):105-109 (1993).
Andersen et al., "A gene duplication led to specialized γ-aminobutyrate and β-alanine aminotransferase in yeast," *FEBS J.* 274:1804-1817 (2007).
Anderson and Dawes, "Occurrence, metabolism, metabolic role, and industrial uses of bacterial polyhydroxyalkanoates," *Microbiol. Rev.* 54(4):450-472 (1990).
Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).
Andersson et al., "Effect of different carbon sources on the production of succinic acid using metabolically engineered *Escherichia coli*," *Biotechnol. Prog.* 23(2):381-388 (2007).

Andreesen and Ljungdahl, "Formate Dehydrogenase of Clostridium thermoaceticum: Incorporation of Selenium-75, and the Effects of Selenite, Molybate, and Tungstate on the Enzyme," *J. Bacteriol.* 116(2):867-873 (1973).
Aneja and Charles, "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).
Angrand et al., "Simplified generation of targeting constructs using ET recombination," *Nucleic Acids Res.* 27(17):e16 (1999).
Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68:557-562 (2000).
Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).
Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).
Aoshima et al., "A novel enzyme, citryl-CoA lyase, catalysing the second step of the citrate cleavage reaction in *Hydrogenobacter thermophilus* TK-6," *Mol. Microbiol.* 52(3):763-770 (2004).
Aoshima et al., "A novel enzyme, citryl-CoA synthetase, catalysing the first step of the citrate cleavage reaction in *Hydrogenobacter thermophilus* TK-6," *Mol. Microbiol.* 52(3):751-761 (2004).
Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).
Aoshima, "Novel enzyme reactions related to the tricarboxylic acid cycle: phylogenetic/functional implications and biotechnological applications," *Appl. Microbiol. Biotechnol.* 75(2):249-255 (2007).
Aragon and Lowenstein, "A survey of Enzymes Which Generate or Use Acetoacetyl Thioesters in Rat Liver," *J. Biol. Chem.* 258(8):4725-4733 (1983).
Arendsen et al., "Nitrate-Dependent Regulation of Acetate Biosynthesis and Nitrate Respiration by clostridium thermoaceticum," *J. Bacteriol.* 181:1489-1495 (1999).
Argyrou and Blanchard, "Kinetic and chemical mechanism of Mycobacterium tuberculosis 1-deoxy-D-xylulose-5-phosphate isomeroreductase," *Biochemistry* 43:4375-4384 (2004).
Arikawa et al., "Soluble fumarate reductase isoenzymes from *Saccharomyces cerevisiae* are required for anaerobic growth," *FEMS Microbiol. Lett.* 165:111-116 (1998).
Aristidou et al., "Metabolic Engineering of *Escherichia coli* to Enhance Recombinant Protein Production through Acetate Reduction," *Biotechnol. Prog.* 11(4):475-478 (1995).
Aristidou et al., "Metabolic flux analysis of *Escherichia coli* expressing the *Bacillus subtilis* Acetolactate Synthase in Batch and Continuous Cultures," *Biotechnol. Bioeng.* 63(6):737-749 (1999).
Armstrong et al., "Steroselectivity and sterospecificity of the α,β-dihydroxyacid dehydratase from *Salmonella typhimurium*," *Biochim. Biophys. Acta* 498:282-293 (1977).
Arps et al., "Genetics of serine pathway enzymes in *Methylobacterium extorquens* AM1: phosphoenolpyruvate carboxylase and malyl Coenzyme A lyase," *J. Bacteriol.* 175:3776-3783 (1993).
Asano and Kato, "Crystalline 3-methylaspartase from a facultative anaerobe, *Escherichia coli* strain YG1002," *FEMS Microbiol. Lett.* 118(3):255-258 (1994).
Asano et al., "Alteration of substrate specificity of aspartase by directed evolution," *Biomol. Eng.* 22(1-3):95-101 (2005).
Asanuma et al., "Characterization and transcription of the genes encoding enzymes involved in butyrate production in Butyrivibrio fibrisolvens," *Curr. Microbiol.* 45:203-207 (2003).
Asuncion et al., "Overexpression, purification, crystallization and data collection of 3-methylaspartase from *Clostridium tetanomorphum*," *Acta. Crystallogr. D. Biol. Crystallogr.* 57 (Pt 5):731-733 (2001).

Asuncion et al., "The structure of 3-methylaspartase from *Clostridium tetanomorphum* functions via the common enolase chemical step," *J. Biol. Chem.* 277(10):8306-8311 (2002).

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Atteia et al., "Pyruvate formate-lyase and a novel route of eukaryotic ATP synthesis in *Chlamydomonas* mitochondria," *J. Biol. Chem.* 281:9909-9918 (2006).

Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).

Baba et al., "Construction of *Escherichia coli* K-12 in-frame, single-gene knockout mutants: the Keio collection," *Mol. Syst. Biol.* 2:2006.0008 (2006).

Bachmann and Townsend, "β-Lactam synthetase: a new biosynthetic enzyme," *Proc. Natl. Acad. Sci. U.S.A.* 95(16):9082-9086 (1998).

Bai et al., "Lewis-acid assisted cross metathesis of acrylonitrile with functionalized olefins catalyzed by phosphine-free ruthenium carbene complex," *Org. Biomol. Chem.* 3:4139-4142 (2005).

Bailey et al., "Identification, cloning, purification, and enzymatic characterization of Mycobacterium tuberculosis 1-deoxy-D-xylulose 5-phosphate synthase," *Glycobiology* 12:813-820 (2002).

Baird et al., "Enzymes involved in acetoacetate formation in various bovine tissues," *Biochem. J.* 117(4):703-709 (1970).

Baker and van der Drift, "Purification and properties of L-erythro-3,5-diaminohexanoate dehydrogenase from Clostridium sticklandii," *Biochemistry* 13(2):292-299 (1974).

Baker et al., "Purification and properties of L-erythro-3,5-diaminohexanoate dehydrogenase from a lysine-fermenting Clostridium," *J. Biol. Chem.* 247:7724-7734 (1992).

Bakker et al., "Stoichiometry and compartmentation of NADH metabolism in *Saccharomyces cerevisiae*," *FEMS Microbiol. Rev.* 25:15-37 (2001).

Banerji et al., "The cloning and characterization of the arom gene of *Pneumocystis carinii*," *J. Gen. Microbiol.* 139:2901-2914 (1993).

Barber et al., "Structure and regulation of acetyl-CoA carboxylase genes of metazoa," *Biochimica. Biophysica. Acta* 1733:1-28 (2005).

Barker and Frost, "Microbial synthesis of p-hydroxybenzoic acid from glucose," *Biotechnol. Bioeng.* 76:376-390 (2001).

Barker et al., "Butyryl-CoA:Acetoacetate CoA-transferase from Lysine-fermenting clostridium," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick et al., "Quantitative analysis of ribosome binding sites in *E.coli*," *Nucleic Acids Res.* 22(7):1287-1295 (1994).

Barrowman et al., "Immunological comparison of microbial TPP-dependent non-oxidative α-keto acid decarboxylase," *FEMS Microbiol. Lett.* 34:57-60 (1986).

Barthelmebs et al., "Expression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).

Barthelmebs et al., "Inducible metabolism of phenolic acids in *Pedicoccus pentosaecus* is encoded by an autoregulated operon which involves a new class of negative transcriptional regulator," *J. Bacteriol.* 182:6724-6731 (2000).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).

Basset et al., "Folate synthesis in plants: the p-aminobenzoate branch is initiated by a bifunctional PabA-PabB protein that is targeted to plastids," *Proc. Natl. Acad. Sci U. S. A* 101:1496-1501 (2004).

Battaile et al., "Structures of isobutyryl-CoA dehydrogenase and enzyme-product complex: Comparison with isovaleryl- and short-chain acyl-CoA dehydrogenases," *J. Biol. Chem.* 279:16526-16534 (2004).

Baudin et al., "A simple and efficient method for direct gene deletion in *Saccharomyces cerevisiae*," *Nucleic Acids Res.* 21(14):3329-3330 (1993).

Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).

Beatrix et al., "The biotin-dependent sodium ion pump glutaconyl-CoA decarboxylase from *Fusobactevium nucleatum* (subsp. nucleatum). Comparison with the glutaconyl-CoA decarboxylases from gram-positive bacteria," *Arch. Microbiol.* 154(4):362-369 (1990).

Beckers et al., "Large-scale mutational analysis for the annotation of the mouse genome," *Curr. Opin. Chem. Biol.* 6:17-23 (2001).

Benner et al., "Stereospecificity and sterochemical infidelity of acetoacetate decarboxylase (AAD)," *J. Am. Chem. So.* 103:993-994 (1981).

Benning et al., "New reactions in the crotonase superfamily: Structure of methylmalonyl CoA decarboxylase from *Escherichia coli*," *Biochemistry* 39:4630-4639 (2000).

Berg et al., "A 3-Hydroxypropionate/4-Hydroxybutyrate Autotrophic Carbon Dioxide Assimilation Pathway in Archaea," *Science* 318(5857) 1782-1786 (2007).

Bergquist and Gibbs, "Degenerate oligonucleotide gene shuffling," *Meth. Mol. Biol.* 352:191-204 (2007).

Bergquist et al., "Degenerate oligonucleotide gene shuffling (DOGS) and random drift mutagenesis (RNDM): Two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. U.S.A.* 101:15870-15875 (2004).

Berman and Magasanik, "The pathway of myo-inositol degradation in *Aerobacter aerogenes*," *J. Biol. Chem.* 241(4):800-806 (1966).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Berrios-Rivera et al., "Metabolic Engineering of *Escherichia coli*: Increase of NADH Availability by Overexpressing an $NAD^+$-Dependent Formate Dehydrogenase," *Metab. Eng.* 4(3):217-229 (2002).

Berthold et al., "Structure of the branched-chain keto acid decarboxylase (KdcA) from *Lactococcus lacti* prvides insights into structural basis for the chemoselective enantioselective carboligation reaction," *Acta. Crystallogr. D. Biol. Crystallogr.* 63(Pt 12):1217-1224 (2007).

Biellmann et al., "Aspartate-β-semialdehyde dehydrogenase from *Escherichia coli*. Purification and general properties," *Eur. J. Biochem.* 104(1):53-58 (1980).

Binieda et al., "Purification, characterization, DNA sequence and cloning of a pimeloyl-CoA synthetase from *Pseudomonas mendocina* 35," *Biochem. J.* 340:793-801 (1999).

Binstock and Schulz, "Fatty acid oxidation complex from *Escherichia coli*," *Methods. Enzymol.* 71(Pt C):403-411 (1981).

Birch et al., "Cloning, sequencing, and expression of the gene encoding methylmalonyl-Coenzyme a mutase from *Streptomyces cinnamonensis*," *J. Bacteriol.* 175(11):3511-3519 (1993).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Bisswanger, "Substrate specificity of the Pyruvate Dehydrogenase Complex from *Escherichia coli*," *J. Biol. Chem.* 256(2):815-822 (1981).

Blanco et al., "Critical catalytic functional groups in the mechanism of aspartate-βsemialdehyde dehydrogenase," *Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).
Blombach et al., "Corynebacterium glutamicum tailored for high-yield L-valine production," *Appl. Microbiol. Biotechnol.* 79(3):471-479 (2008).
Blomqvist et al., "Characterization of the genes of the 2,3-butanediol operons from Klebsiella terrigena and *Enterobacter aerogenes*," *J. Bacteriol.* 175:1392-1404 (1993).
Bobik and Rasche, "HPLC assay for methylmalonyl-CoA epimerase," *Anal. Bioanal. Chem.* 375(3):344-349 (2003).
Bobik and Rasche, "Identification of the human methylmalonyl-CoA racemase gene based on the analysis of prokaryotic gene arrangements. Implications for decoding the human genome," *J. Biol. Chem.* 276(40):37194-37198 (2001).
Bobik et al., "Propanediol Utilization Genes (pdu) of *Salmonella typhimurium*: Three Genes for the Propanediol Dehydratase," *J. Bacteriol.* 179(21):6633-6639 (1997).
Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867 (1999).
Boiangiu et al., "Sodium Ion Pumps and Hydrogen Production in Glutamate Fermenting Anaerobic Bacteria," *J. Mol. Microbiol. Biotechnol.* 10:105-119 (2005).
Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).
Bonnarme et al., "Itaconate biosynthesis in *Aspergillus terreus*," *J. Bacteriol.* 177(12):3573-3578 (1995).
Bonner and Bloch, "Purification and properties of fatty acyl thioesterase I from *Escherichia coli*," *J. Biol. Chem.* 247(10):3123-3133 (1972).
Boronin et al., "Plasmids specifying ε-caprolactam degradation in *Pseudomonas* strains," *FEMS Microbiol Lett.* 22(3):167-170 (1984).
Bose et al., "Genetic analysis of the methanol- and methylamine-specific methyltransferase 2 genes of Methanosarcina acetivorans C2A," *J. Bacteriol.* 190(11):4017-4026 (2008).
Bott et al., "Methylmalonyl-CoA decarboxylase from Propionigenium modestum. Cloning and sequencing of the structural genes and purification of the enzyme complex," *Eur. J. Biochem.* 250:590-599 (1997).
Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).
Bottomley et al., "Cloning, sequencing, expression, purification and preliminary characterization of type II dehydroquinase from Helicobacter pylori," *Biochem. J.* 319:559-565 (1996).
Bower et al., "Cloning, sequencing, and characterization of the *Bacillus subtilis* biotin biosynthetic operon," *J. Bacteriol.* 178(14):4122-4130 (1996).
Boylan and Dekker, "L-Threonine Dehydrogenase of *Escherichia coli* K-12," *Biochem. Biophys. Res. Commun.* 85(1):190-197 (1978).
Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol.* 178(11):3015-3024 (1996).
Brachmann et al., "Designer deletion strains derived from *Saccharomyces cerevisiae* S288C: a useful set of strains and plasmids for PCR-mediated gene disruption and other applications," *Yeast* 14(2):115-132 (1998).
Bradford, "A rapid and sensitive method for the quantitation of microgram quantities of protein utilizing the principle of protein-dye binding," *Anal. Biochem.* 72:248-254 (1976).
Branlant, "Nucleotide sequence of *Escherichia coli* gap gene. Different evolutionary behavior of the $NAD^+$-binding domain and of the catalytic domain of D-glyceraldehyde3-phosphate dehydrogenase," *Eur. J. Biochem.* 150:61-66 (1985).
Bräsen and Schönheit, "Unusual ADP-forming acetyl-Coenzyme a synthetases from the mesophilic halophilic euryarchaeon Haloarcula marismortui and from the hyperthermophilic crenarchaeon Pyrobaculum aerophilum," *Arch. Microbiol.* 182(4):277-287 (2004).
Braune et al., "The sodium ion translocating glutaconyl-CoA decarboxylase from Acidaminococcus fermentans: cloning and function on the genes forming a second operon," *Mol. Microbiol.* 31(2):473-487 (1999).
Bravo et al., "Reliable, sensitive, rapid and quantitative enzyme-based assay for gamma-hydroxybutyric acid (GHB)," *J. Forensic Sci.* 49:379-387 (2004).
Bredwell et al., "Reactor Design Issues for Synthesis-Gas Fermentations," *Biotechnol. Prog.* 15(5):834-844 (1999).
Breese et al., "Genes coding for the benzoyl-CoA pathway of anaerobic aromatic metabolism in the bacterium Thauera aromatica," *Eur. J. Biochem.* 256(1):148-154 (1998).
Breitkruez et al., "A novel γ-hydroxybutyrate dehydrogenase: Identification and expression of an Arabidopsis cDNA and potential role under oxygen deficiency," *J. Biol. Chem.* 278:41552-41556 (2003).
Bremer, "Pyruvate Dehydrogenase, Substrate Specificity and Product Inhibition," *Eur. J. Biochem.* 8:535-540 (1969).
Brey et al., "Cloning of multiple genes involved with cobalamin (Vitamin $B_{12}$) biosynthesis in *Bacillus megaterium*," *J. Bacteriol.* 167:623-630 (1986).
Bro et al., "In silico aided metabloic engineering of *Saccharomyces cerevisiae* for improved bioethanol production," *Metab. Eng.* 8(2):102-111 (2006).
Brooke et al., "GAMS: A User's Guide. GAMS Development Corporation," (1998).
Broun et al., "Catalytic plasticity of fatty acid modification enzymes underlying chemical diversity of plant lipids," *Science* 282:1315-1317 (1998).
Brown et al., "A role for *pabAB*, a p-aminobenzoate synthase gene of *Streptomyces venezuelae* ISP5230, in chloramphenicol biosynthesis," *Microbiol.* 142 ( Pt 6):1345-1355 (1996).
Brown et al., "Comparative structural analysis and kinetic properties of lactate dehydrogenases from the four species of human malarial parasites," *Biochemistry* 43:6219-6229 (2004).
Browner et al., "Sequence analysis, biogenesis, and mitochondrial import of the α-subunit of rat liver propionyl-CoA carboxylase," *J. Biol. Chem.* 264:12680-12685 (1989).
Bu and Tobin, "The exon-intron organization of the genes (GAD1 and GAD2) encoding two human glutamate decarboxylases ($GAD_{67}$ and $GAD_{65}$) suggests that they derive from a common ancestral GAD," *Genomics* 21:222-228 (1994).
Bu et al., "Two human glutamate decarboxylases, 65-kDa GAD and 67-kDa GAD, are each encoded by a single gene," *Proc. Natl. Acad. Sci. U.S.A.* 89:2115-2119 (1992).
Buchanan et al., "An extremely thermostable aldolase from *Sulfolobus solfataricus* with specificity for non-phosphorylated substrates," *Biochem. J.* 343:563-570 (1999).
Buck et al., "Primary structure of the succinyl-CoA synthetase of *Escherichia coli*," *Biochem.* 24(22):6245-6252 (1985).
Buckel and Barker, "Two pathways of glutamate fermentation by anaerobic bacteria," *J. Bacteriol.* 117(3):1248-1260 (1974).
Buckel and Golding, "Radical enzymes in anaerobes," *Annu. Rev. Microbiol.* 60:27-49 (2006).
Buckel and Golding, "Radical species in the catalytic pathways of enzymes from anaerobes," *FEMS Microbiol. Rev.* 22(5):523-541 (1999).
Buckel et al., "ATP-Driven electron transfer in enzymatic radical reactions," *Curr. Opin. Chem. Biol.* 8:462-467 (2004).
Buckel et al., "Glutaconate CoA-Transferase from Acidaminococcus fermentans," *Eur. J. Biochem.* 118:315-321 (1981).
Buckel et al., "Radical-mediated dehydration reactions in anaerobic bacteria," *Biol. Chem.* 386:951-959 (2005).
Buckel, "Sodium ion-translocating decarboxylases," *Biochimica. Biophysica. Acta.* 1505:15-27 (2001).
Bueding and Yale, "Production of α-methylbutyric acid by bacteria-free *Ascaris lumbricoides*," *J. Biol. Chem.* 193:411-423 (1951).

Bühler and Simon, "On the kinetics and mechanism of enoate reductase," *Hoppe Seylers Z. Physiol. Chem.* 363(6):609-625 (1982).
Bunch et al., "The *ldhA* gene encoding the fermentative lactate dehydrogenase of *Escherichia coli*," *Microbiol.* 143:187-195 (1997).
Burgard and Maranas, "Probing the performance limits of the *Escherichia coli* metabolic network subject to gene additions or deletions," *Biotechnol. Bioeng.* 74:364-375 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burke et al., "The Isolation, Characterization, and Sequence of the Pyruvate Kinase Gene of *Saccharomyces cerevisiae*," *J. Biol. Chem.* 258(4):2193-2201 (1983).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Ach1p, in *Saccharomyces cerevisiae*," *J. Biol. Chem.* 278:17203-17209 (2003).
Buzenet et al., "Purification and properties of 4-Aminobutyrate 2-Ketoglutarate Aminotransferase From Pig Liver," *Biochimica. Biophysica. Acta* 522:400-411 (1978).
Byrnes et al., "Thermodynamics of reactions catalyzed by anthranilate synthase," *Biophys. Chem.* 84:45-64 (2000).
Cahyanto et al., "Regulation of aspartokinase, asparate semialdehyde dehydrogenase, dihydrodipicolinate synthease and dihydropdipicolinate reductase in *Lactobacillus plantarum*," *Microbiology* 152 (Pt 1): 105-112 (2006).
Caldovic and Tuchman, "N-Acetylglutamate and its changing role through evolution," *Biochem. J.* 372:279-290 (2003).
Calhoun et al., "Threonine deaminase from *Eschericiha coli*. I. Purification and properties," *J. Biol. Chem.* 248(10):3511-3516 (1973).
Camara et al., "Characterization of a Gene Cluster Involved in 4-Chlorocatechol Degradation by *Pseudomonas reinekei* MT1," *J. Bacteriol.* 191(15):4905-4915 (2009).
Campbell and Cronan, Jr., "The enigmatic *Escherichia coli* fadE gene is yafH," *J. Bacteriol.* 184(13):3759-3764 (2002).
Campbell et al., "A complete shikimate pathway in Toxoplasma gondii: an ancient eukaryotic innovation," *Int. J. Parasitol.* 34:5-13 (2004).
Campbell et al., "A new *Escherichia coli* metabolic competency: growth on fatty acids by a novel anaerobic β-oxidation pathway," *Mol. Microbiol.* 47(3):793-805 (2003).
Canovas et al., "Characterization of the genes for the biosynthesis of the compatible solute ecotine in the moderately haliphilic bacterium *Halomonas elongate* DSM 3043," *Syst. Appl. Microbiol.* 21:487-497 (1998).
Cao et al., "Simultaneous Production and recovery of Fumaric Acid from Immobilized Rhizopus oryzae with a Rotary biofilm Contactor and an Adsorption Column," *Appl. Environ. Microbiol.* 62(8):2926-2931 (1996).
Carlini et al., "Guerbet condensation of methanol with n-propanol to isobutyl alcohol over heterogeneous copper chromite/Mg—Al mixed oxides catalysts," *J. Mol. Catal. A. Chem.* 220:215-220 92004).
Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A. Chem.* 206:409-418 (2003).
Carlini et al., "Selective synthesis of isobutanol by means of the Guebet reaction Part 1. Methanol/n-propanol condensation by using copper based catalytic systems," *J. Mol. Catal. A. Chem.* 184:273-280 (2002).
Carlini et al., "Selective synthesis of isobutanol by means of the Guerbet reaction Part 2. Reaction of methanol/ethanol and methanol/ethanol/n-propanol mixtures over copper based MeONa catalytic systems," *J. Mol. Catal. A. Chem.* 200:137-146 (2003).
Carpenter et al., "Structure of dehydroquinate synthase reveals an active site capable of multistep catalysis," *Nature* 394:299-302 (1998).
Carretero-Paulet et al., "Expression and molecular analysis of the Arabidopsis DXR gene encoding1-deoxy-D-xylulose 5-phosphate reductoisomerase, the firszt committed enzyme of the 2-C-methyl-D-erythritiol 4-phosphate pathway," *Plant Physiol.* 129:1581-1591 (2002).
Carta et al., "Production of fumaric acid by fermentation of enzymatic hydrolysates derived from *Cassava bagasse*," *Biores. Tech.* 68:23-28 (1999).
Cary et al., "Cloning and Expression of Clostridium acetobutylicum ATCC 824 Acetoacetyl-Coenzyme A:Acetate/Butyrate:Coenzyme A-Transferase in *Escherichia coli*," *App. Environ. Microbiol.* 56(6):1576-1583 (1990).
Cary et al., "Cloning and expression of *Clostridium acetobutylicum* phosphotransbutyrylase and butyrate kinase genes in *Escherichia coli*," *J. Bacteriol.* 170(10):4613-4618 (1988).
Casero and Pegg, "Spermidine/spermine $N^1$-acetyltransferase—the turning point in polyamine metabolism," *FASEB J.* 7:653-661 (1993).
Caspi et al., "MetaCyc: a multiorganism database of metabolic pathways and enzymes," *Nucleic Acids Res.* 34(Database issue):D511-D516 (2006).
Cavin et al., "Gene cloning, transcriptional analysis, purification, and characterization of phenolic acid decarboxylase from *Bacillus subtilis*," *Appl. Environ. Microbiol.* 64(4):1466-1471 (1998).
Cha and Bruce, "Stereo- and regiospecific cis,cis-muconate cycloisomerization by *Rhodococcus rhodochrous* N75," *FEMS Microbiol. Lett.* 224:29-34 (2003).
Cha and Parks, Jr., "Succinic Thiokinase. I. Purification of the Enzyme from Pig Heart," *J. Biol. Chem.* 239:1961-1967 (1964).
Chandra et al. "Pyruvate decarboxylase: a key enzyme for the oxidative metabolism of lactic acid by Acetobacter pasteurianus," *Arch. Microbiol.* 176:443-451 (2001).
Chang et al., "p-Aminobenzoic acid and chloramphenicol biosynthesis in *Streptomyces venezuelae*: gene sets for a key enzyme, 4-amino-4-deoxychorismate synthase," *Microbiology* 147:2113-2126 (2001).
Chang et al., "Effects of deletions at the carboxyl terminus of Zymomonas mobills pyruvate decarboxylase on the kinetic properties and substrate specificity," *Biochemistry* 39(31):9430-9437 (2000).
Chao and Ramsdell, "The effects of wall populations on coexistence of bacteria in the liquid phase of chemostat cultures," *J. Gen. Microbiol.* 131(5):1229-1236 (1985).
Chaparro-Riggers et al., "Comparison of Three Enoate Reductases and their Potential Use for Biotransformations," *Adv. Synth. Catal.* 349:1521-1531 (2007).
Charles et al., "The isolation and nucleotide sequence of the complex AROM locus of *Aspergillus nidulans*," *Nucleic Acids Res.* 14:2201-2213 (1986).
Charrier et al., "A novel class of CoA-transferase involved in short-chain fatty acid metabolism in butyrate-producing human colonic bacteria," *Microbiology* 152:179-185 (2006).
Chatterjee et al., "A general model for selectively in olefin cross methathesis," *J. Am. Chem. Soc.* 125 (37):11360-11370 (2003).
Chatterjee et al., "Mutation of the ptsG Gene Results in Increased Production of Succinate in Fermentation of Glucose by *Escherichia coli*," *Appl. Env. Microbiol.* 67:148-154 (2001).
Chaudhuri et al., "Identification of the active-site lysine residues of two biosynthetic 3-dehydroquinases," *Biochem. J.* 275:1-6 (1991).
Chen and Hiu, "Acetone-Butanol-Isopropanol Production by *Clostridium beijerinckii* (Synonym, Clostridium Butylicum)," *Biotechnology Letters* 8(5):371-376 (1986).
Chen et al., "A novel lysine 2,3-aminomutase encoded by the yodO gene of *Bacillus subtilis*: characterization and the observation of organic radical intermediates," *Biochem. J.* 348:539-549 (2000).
Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).
Chen et al., "The control region of the pdu/cob regulon in *Salmonella typhimurium*," *J. Bacteriol.* 176:5474-5482 (1994).

Cheng et al., "Genetic Analysis of a Gene Cluser for Cyclohexanol Oxidation in *Acinetobacter* sp. Strain SE19 by In Vitro Transportation," *J. Bacteriol.* 182(17):4744-4751 (2000).

Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).

Cheng et al., "Mammalian Wax Biosynthesis. II. Expression cloning of wax synthase cDNAs encoding a member of the acyltransferase enzyme family," *J. Biol. Chem.* 279(36):37798-37807 (2004).

Cheng et al., "Structural basis for shikimate-binding specificity of *Helicobacter pylori* shikimate kinase," *J. Bacteriol.* 187:8156-8163 (2005).

Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).

Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).

Cho et al., "Critical residues for the Coenzyme specificity of $NAD^+$-dependent 15-hydroxyprostaglandin dehydrogenase," *Arch. Biochem. Biophys.* 419:139-146 (2003).

Choi et al, "Olefin Metathesis Involving Ruthenium Enoic Carbene Complexes," *J. Am. Chem. Soc.* 123(42):10417-10418 (2001).

Choi et al., "Enhanced production of cis,cis-muconate in a cell-recycle bioreactor," *J. Ferment. Bioeng.* 84:70-76 (1997).

Choi-Rhee and Cronan, "The biotin carboxylase-biotin carboxyl carrier protein complex of *Escherichia coli* acetyl-CoA carboxylase," J. Biol. Chem. 278:30806-30812 (2003).

Chopra et al., "Expression, purification, and biochemical characterization of Mycobacterium tuberculosis aspartate decarboxylase, PanD," *Protein Expr. Purif.* 25:533-540 (2002).

Chou et al., "Effect of Modulated Glucose Uptake on High-Level Recombinant Protein Production in a Dense *Escherichia coli* Culture," *Biotechnol. Prod.* 10:644-647 (1994).

Chowdhury et al., "3-Hydroxyisobutyrate dehydrogenase from *Pseudomonas putida* E23: purification and characterization," *Biosci. Biotechnol. Biochem.* 60(12):2043-2047 (1996).

Chowdhury et al., "Cloning and overexpression of the 3-hydroxyisobutyrate dehydrogenase gene from *Pseudomonas putida* E23," *Biosci. Biotechnol. Biochem.* 67(2):438-441 (2003).

Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).

Chuakrut et al., "Characterization of a bifunctional archael acyl Coenzyme A carboxylase," *J. Bacteriol.* 185:938-947 (2003).

Clark and Ljungdahl, "Purification and properties of 5,10-methylenetetrahydrofolate reductase from *Clostridium formicoaceticum*," *Methods Enzymol.* 122:392-399 (1986).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark et al., "Mutants of *Escherichia coli* defective in acid fermentation," *Appl. Biochem. Biotechnol.*17:163-173 (1988).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-Hydroxyacid Dehydrogenase With New Substrate Specificity," *Biochem. Biophys. Res. Commun.* 148:15-23 (1987).

Clausen et al., "PAD1 encodes phenylarcrylic acid decarboxylase which confers resistance to cinnamic acid in *Saccharomyces cerevisiae*," *Gene* 142:107-112 (1994).

Coco et al., "DNA shuffling method for generating highly recombined genes and evolved enzymes," *Nat. Biotechnol.* 19:354-359 (2001).

Coggins et al., "The arom multifunctional enzyme from *Neurospora crassa*," *Methods. Enzymol.* 142:325-341 (1987).

Colby and Chen, "Purification and properties of 3-hydroxybutyryl-Coenzyme A dehydrogenase from *Clostridium beijerinckii* ("Clostridium butylicum") NRRL B593," *Appl. Environ. Microbiol.* 58:3297-3302 (1992).

Coleman, "Expression of a glutamate decarboxylase homologue is required for normal oxidative stress tolerance in *Saccharomyces cerevisiae*," *J. Biol. Chem.* 276:244-250 (2001).

Conrad et al., "D- and L-Isoleucine Metabolism and Regulation of Their Pathways in *Pseudomonas putida*," *J. Bacteriol.* 118(1):103-111 (1974).

Cooper, "Glutamate-γ-aminobutyrate transaminase," *Methods Enzymol.* 113:80-82 (1985).

Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.* 272(41):25659-25667 (1997).

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1992).

Cox et al., "Development of a metabolic network design and optimization framework incorporating implementation constraints: A succinate production case study," *Metab. Eng.* 8(1):46-57 (2006).

Craney et al., "A synthetic luxCDABE gene cluster optimized for expression in high-GC bacteria," *Nucleic Acids Res.* 35(6):e46 (2007).

Cukalovic et al., "Feasibility of production method for succinic acid derivatives: a marriage of renewable resources and chemical technology," *Biofuels Bioprod. Bioref.* 2:505-529 (2008).

Cunningham et al., "Transcriptional regulation of the aconitase genes (acnA and acnB) of *Escherichia coli*," *Microbiology* 143(Pt 12):3795-3805 (1997).

Dai et al., "Highly Selective Diels-Alder Reactions of directly Connected Enzyne Dienphiles," *J. Am. Chem. Soc.* 129:645-657 (2007).

Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).

Dal et al., "Transcriptional Organization of Genes for Protocatechuate and quinate Degradation from *Acinetobacter* sp. Strain ADP1," *Appl. Environ. Microbiol.* 71(2):1025-1034 (2005).

Dangel et al., "Anaerobic metabolism of cyclohexanol by denitrifying bacteria," *Arch. Microbiol.* 150(40):358-362 (1988).

Dangel et al., "Enzyme reactions involved in anaerobic cyclohexanol metabolism by a dentitrifying Psedomonas species," *Arch. Microbiol.* 152:273-279 (1989).

D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*," *J. Biol. Chem.* 266(35):23953-23958 (1991).

Das et al., "Characterization of a corrinoid protein involved in the C1 metabolism of strict anaerobic bacterium Moorella thermoacetica," *Proteins* 67(1):167-176 (2007).

Datar et al., "Fermentation of biomass-generated producer gas to ethanol," *Biotechnol. Bioeng.* 86(5):587-594 (2004).

Datsenko et al., "One-step inactivation of chromosomal genes in *Escherichia coli* K-12 using PCR products," *Proc. Natl. Acad. Sci. U.S.A.* 97:6640-6645 (2000).

Datta et al., "Covalent structure of biodegradative threonine dehydratase of *Escherichi coli*: homology with other dehydratases," *Proc. Natl. Acad. Sci. U.S.A.* 84(2):393-397 (1987).

Davey and Trudgill, "The metabolism of trans-cyclohexan-1,2-diol by an Acinetobacter species," *Eur. J. Biochem.* 74(1):115-127 (1977).

Davids et al, "Characterization of the *N*-acetyltransferases respectively responsible for arylalkylamine and diamine acetylation in Ascaris suum," *Mol. Biochem. Parasitol.* 64(2):341-344 (1994).

Davie et al., "Expression and assembly of a functional E1 component ($\alpha_2\beta_2$) of mammalian branched-chain α-ketoacid dehydrogenase complex in *Escherichia coli*," *J. Biol. Chem.* 267:16601-16606 (1992).

De Biase et al., "Isolation, overexpression, and biochemical characterization of the two isoforms of glutamic acid decarboxylase from *Escherichia coli*," *Protein Expr. Purif.* 8:430-438 (1996).

de Bok et al., "Two W-containing formate dehydrogenases ($CO_2$-reductases) involving syntrophic propionate oxidation by Syntrophobacter fumaroxidans," *Eur. J. Biochem.* 270:2476-2485 (2003).

de Crecy et al., "Development of a novel continuous culture device for experimental evolution of bacterial populations," *Appl. Microbiol. Biotechnol.* 77(2): 489-496 (2007).

de la Torre et al., "Identification and functional analysis of a prokaryotic-type aspartate aminotransferase: implications for plant amino acid metabolism," *Plant. J.* 46(3):414-425 (2006).

de Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).

de Mendonca et al., "Functional characterization by genetic complementation of aroB-encoded dehydroquinate synthase from Mycobacterium tuberculosis H37Rv and its heterologous expression and purification," *J. Bacteriol.* 189:6246-6252 (2007).

de Smidt et al., "The alcohol dehydrogenases of *Saccharomyces cerevisiae*: a comprehensive review," *FEMS Yeast Rev.* 7:967-978 (2008).

Deana, "Substrate specificity of a dicarboxyl-CoA: dicarboxylic acid Coenzyme A transferase from rat liver mitochondria," *Biochem. Int.* 26(4):767-773 (1992).

DeFeyter and Pittard, "Purification and properties of shikimate kinase II from *Escherichia coli* K-12," *J. Bacteriol.* 165:331-333 (1986).

Del Campillo-Campbell et al., "Biotin-requiring Mutants of *Escherichia coli* K-12," *J. Bacteriol.* 94(6):2065-2066 (1967).

Deno, "The Diels-Alder Reaction with α, β, γ, δ-Unsaturated Acids," *J. Am. Chem. Soc.* 72:4057-4059 (1950).

Department of Energy, "Top value added chemicals from biomass. vol. I—Results of Screening for Potential Candidates from Sugars and Synthesis Gas," *Biomass*, Aug. 2004.

Desvaux, "Clostridium cellulolyticum: model organism of mesophilic cellulolytic clostridia," *FEMS Microbiol. Rev.* 29(4):741-764 (2005).

Devos et al., "Practical limits of function prediction," *Proteins* 41:98-107 (2000).

Di Gennaro, "Styrene lower catabolic pathway in *Pseudomonas fluorescens* ST: identification and characterization of genes for phenylacetic acid degradation," *Arch. Microbiol.* 188(2):117-125 (2007).

Diao et al., "Crystal structure of butyrate kinase 2 from Thermotoga maritima, a member of the ASKHA superfamily of phosphotransferases," *J. Bacteriol.* 191:2521-2529 (2009).

Diao et al., "Crystallization of the butyrate kinase 2 from Thermotoga maritima mediated by vapor diffusion of acetic acid," *Acta. Crystallogr D. Biol. Crystallogr.* 59(Pt 6):1100-1102 (2003).

Dias et al., "Well-Defined Ruthenium Olefin Metathesis Catalyst: Mechanism and Activity," *J. Am. Chem. Soc.* 119(17):3887-3897 (1997).

Diaz et al., "Gene cloning, heterologous overexpression and optimized refolding of the NAD-glutamate dehydrogenase from *Haloferax mediterranei*," *Extremophiles* 10:105-115 (2006).

Diderichsen et al., "Cloning of aldB, Which Encodes α-Acetolactate Decarboxylase, an Exoenzyme from *Bacillus brevis*," *J. Bacteriol.* 172(8):4315-4321 (1990).

Dittrich et al., "Redistribution of Metabolic Fluxes in the Central Aerobic Metabolic Pathway of *E. coli* Mutant Strains with Deletion of the ackA-pta and poxB Pathways for the Synthesis of Isoamyl Acetate," *Biotechnol Prog.* 21(2):627-631 (2005).

Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).

Do et al., "Growth of rhodospirillum rubrum on synthesis gas: conversion of CO to $H_2$ and Poly-β-hydroxyalkanoate," *Biotechnol. Bioeng.* 97(2):279-286 (2007).

Dobbek et al., "Crystal structure of a carbon monoxide dehydrogenase reveals a [Ni-4Fe-5S] cluster," *Science* 293(5533):1281-1285 (2001).

Dombek and Ingram, "Ethanol production during batch fermentation with *Saccharomyces cerevisiae*: Changes in glycolytic enzymes and internal pH," *Appl. Environ. Microbiol.* 53:1286-1291 (1987).

Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).

Donnelly and Cooper, "Two succinic semialdehyde dehydrogenases are induced when *Escherichia coli* K-12 Is grown on γ-aminobutyrate," *J. Bacteriol.* 145:1425-1427 (1981).

Donnelly et al., "A novel fermentation pathway in an *Escherichia coli* mutant producing succinic acid, acetic acid, and ethanol," *App. Biochem. Biotech.* 70-72:187-198 (1998).

Doten et al., "Cloning and Genetic Organization of the pca Gene cluster from *Acinetobacter calcoaceticus*," *J. Bacteriol.* 169(7):3168-3174 (1987).

Doyle et al., "Structural Basis for a Change in substrate Specificity: Crystal Structure of S113E Isocitrate Dehydrogenase in a Complex with Isopropylmalate, $Mg^{2+}$ and NAPD," *Biochemistry* 40:4234-4241 (2001).

Drake and Daniel, "Physiology of the thermophilic acetogen Moorella thermoacetica," *Res. Microbiol.* 155(10):869-883 (2004).

Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).

Drake, "Demonstration of hydrogenase in extracts of the homoacetate-fermenting bacterium Clostridium thermoaceticum," *J. Bacteriol.* 150(2):702-709 (1982).

Draths and Frost, "Environmentally compatible synthesis of adipic acid from D-glucose," *J. Am. Chem. Soc.* 116:399-400 (1994).

Drevland et al., "Enzymology and Evolution of the Pyruvate Pathway to 2-Oxobutyrate in Methanocaldococcus jannachii," *J. Bacteriol.* 189(12):4391-4400 (2007).

Drewke et al., "4-O-Phosphoryl-L-threonine, a substrate of the pdxC(serC) gene product involved in vitamin $B_6$ biosynthesis," *FEBS Lett.* 390:179-182 (1996).

Drewke et al., "Ethanol formation in adh) mutants reveals the existence of a novel acetaldehyde-reducing activity in *Saccharomyces cerevisiae*," *J. Bacteriol.* 172:3909-3917 (1990).

Driscoll and Taber, "Sequence Organization and Regulation of the*Bacillus subtilis* menBE Operon," *J. Bacteriol.* 174(15):5063-5071 (1992).

Drummond and Stern, "Enzymes of ketone body metabolism. II. Properties of an acetoacetate-synthesizing enzyme prepared from ox liver," *J. Biol. Chem.* 235:318-325 (1960).

Du et al., "Succinic acid production from wheat using a biorefining strategy," *Appl. Mirobiol. Biotechnol.* 76:1263-1270 (2007).

Duarte et al., "Reconstruction and validation of *Saccharomyces cerevisiae* iND750, a fully compartmentalized genome-scale metabolic model," *Genome Res.* 14(7):1298-1309 (2004).

Duckworth et al., "The Binding of Reduced Nicotinamide Adenine Dinucleotide to Citrate Synthase of *Escherichia coli* K12," *Biochemistry* 15(1):108-114 (1976).

Duncan et al., "The pentafunctional arom enzyme of *Saccharomyces cerevisiae* is a mosaic of monofunctional domains," *Biochem. J.* 246:375-386 (1987).

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Duncombe and Frerman, "Molecular and catalytic properties of the acetoacetyl-Coenzyme A thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anaerobic mitochondria of the parasitic nematode Ascaris suum," *J. Biol. Chem.* 268(30):22391-22396 (1993).

Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).

Durre and Bahl, "Microbial Production of Acetone/Butanol/Isopropanol," In Biotechnology vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Dürre et al., "Solventogenic enzymes of Clostridium acetobutylicum: catalytic properties, genetic organization, and transcriptional regulation," *FEMS Microbiol. Rev.* 17:251-262 (1995).

Dürre, "Biobutanol: an attractive biofuel," *Biotechnol. J.* 2(12):1525-1534 (2007).

Dürre, "New insights and novel developments in clostridial acetone/butanol/isopropanol fermentation," *Appl. Microbiol. Biotechnol.* 49:639-648 (1998).

Dusch et al., "Expression of the Corynebacterium glutamicum panD gene encoding L-aspartate-α-decarboxylase leads to pantothenate overproduction in *Escherichia coli*," *Appl. Environ. Microbiol.* 65(4)1530-1539 (1999).

Dutscho et al., "Cloning and sequencing of the genes of 2-hydoxyglutaryl-CoA dehydratase from *Acidaminococcus fermentans*," *Eur. J. Biochem.* 181(3):741-746 (1989).

Dwiarti et al., "Purification and characterization of cis-aconitic acid decarboxylase from *Aspergillus terreus* TN484-M1," *J. Biosci Bioeng.* 94(1):29-33 (2002).

Dwyer et al., "Proton Abstraction reaction, Steady-State kinetics, and Oxidation-Reduction Potential of Human Glutaryl-CoA Dehydrogenase," *Biochemistry* 39:11488-11499 (2000).

Dykhuizen, "Chemostats used for studying natural selection and adaptive evolution," *Methods. Enzymol.* 224:613-631 (1993).

Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).

Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol.* 55:296-300 (2001).

Edwards and Palsson, "Metabolic flux balance analysis and the in silico analysis of *Escherichia coli* K-12 gene deletions," *BMC Bioinform.* 1:1 (2000).

Edwards and Palsson, "Systems properties of the Haemophilus influenzae Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).

Edwards et al., "Metabolic modelling of microbes: the flux-balance approach," *Environ. Microbiol.* 4(3):133-140 (2002).

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol. Bioeng.* 99:1392-1406 (2008).

Egland et al., "A cluster of bacterial genes for anaerobic benzene ring biodegradation," *Proc. Natl. Acad. Sci. U.S.A.* 94:6484-6489 (1997).

Eikmanns et al., "The phosphoenolpyruvate carboxylase gene of Corynebacterium glutamicum: Molecular cloning, nucleotide sequence, and expression." *Mol. Gen. Genet.* 218:330-339 (1989).

Elshahed et al., "Metabolism of Benzoate, Cyclohex-1-ene Carboxylate, and Cyclohexane Carboxylate by "Syntrophus aciditrophicus" Strain SB in Syntrophic Association with $H_2$-Using Microorganisms," *Appl. Environ. Microbiol.* 67(4):1728-1738 (2001).

Engel, "Butyryl-CoA Dehydrogenase from *Megasphaera elsdenii*," *Methods Enzymol.* 71:359-366 (1981).

Enomoto et al., "Cloning and sequencing of the gene encoding the soluble fumarate reductase from *Saccharomyces cerevisiae*," *DNA Res.* 3:263-267 (1996).

Ensign and Ludden, "Characterization of the CO Oxidation/$H_2$ Evolution System of *Rhodospirillum rubrum*. Role of a 22-kDa ironsulfur protein in mediating electron transfer between carbon monoxide dehydrogenase and hydrogenase," *J. Biol. Chem.* 266(27)18395-18403 (1991).

Estévez et al., "X-ray crystallographic and kinetic correlation of a clinically observed human fumarase mutation," *Protein Sci.* 11(6):1552-1557 (2002).

Eulberg et al., "Characterization of a protocatechuate catabolic gene cluster from *Rhodococcus opacus* 1CP: evidence for a merged enzyme with 4-carboxymuconolactone-cecarboxylating and 3-oxoadipate enol-lactone-hydrolyzing activity," *J. Bacteriol.* 180:1072-1081 (1998).

Evans et al., "[$^{13}$C]propionate oxidatin in wild-type and citrate synthase mutant *Escherichia coli*: evidence for multiple pathways of propionate utilization," *Biochem. J.* 291(Pt 3):927-932 (1993).

Ezeji et al., "Butanol fermentation research: upstream and downstream manipulations," *Chem. Rec.* 4(5):305-314 (2004).

Faehnle et al., "A New Branch in the Family: Structure of Aspartate-β-semialdehyde Dehydrogenase from Methanococcus jannaschii," *J. Mol. Biol.* 353:1055-1068 (2005).

Feist et al., "The growing scope of applications of genome-scale metabolic reconstructions using *Escherichia coli*," *Nat. Biotechnol.* 26(6):659-667 (2008).

Feldberg and Datta, "L-threonine deaminase of *Rhodospirillum rubrum*. Purification and characterization," *Eur. J. Biochem.* 21(3):438-446 (1971).

Fell and Small, "Fat Synthesis in Adipose Tissue. An Examination of Stoichiometric Constraints," *Biochem. J.* 238(3):781-786 (1986).

Fernandez-Canon and Penalva, "Characterization of a fungal maleylacetoacetate isomerase gene and indentification of its human homologue," *J. Biol. Chem.* 273:329-337 (1998).

Fernandez-Valverde et al., "Purification of Pseudomonas putida Acyl Coenzyme A Ligase Active with a Range of aliphatic and Aromatic substrates," *Appl. Environ. Microbiol.* 59(4):1149-1154 (1993).

Fischer and Sauer, "Metabolic flux profiling of *Escherichi coli* mutants in central carbon metabolism using GC-MS," *Eur. J. Biochem.* 270(5):880-891 (2003).

Fish and Blumenthal, "2-Keto-3-deoxy-D-glucarate aldolase," *Methods Enzymol.* 9:529-534 (1996).

Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem.* 241:4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibria," *J. Biol. Chem.* 241:4842-4847 (1966).

Fitzgerald and Flanagan, "Characterization and sequence analysis of the human ornithine decarboxylase gene," *DNA* 8:(9):623-634 (1989).

Flint et al., "The role and properties of the iron-sulfur cluster in *Escherichia coli* dihydroxy-acid dehydratase," *J. Biol. Chem.* 268:14732-14742 (1993).

Flint, "Initial kinetic and mechanistic characterization of *Escherichia coli* fumarase A," *Arch. Biochem. Biophys.* 311(2):509-516 (1994).

Fochi, "Selective catalytic dehydrogenation of 1,4-cyclohexadiene to benzene. 1. Radical anions derived from stransition-metal arene complexes as promoters," *Organometallics* 7:2255-2256 (1988).

Fomine and Tlenkopatchev, "Cross-methathesis of dimethyl maleate and ethylene catalyzed by second generation ruthenium carbene compleses: B3LYP and MPW1K comparison study," *J. Org. Chem.* 691:5189-5196 (2006).

Fong and Palsson, "Metabolic gene-deletion strains of *Escherichia coli* evolve to computationally predicted growth phenotypes," *Nat. Genet.* 36(10):1056-1058 (2004).

Fong et al., "Description and Interpretation of Adaptive Evolution of *Escherichia coli* K-12 MG1655 by Using a Genome-Scale in Silico Metabolic Model," *J. Bacteriol.* 185(21):6400-6408 (2003).

Fong et al., "In Silico design and adaptive evolution of *Escherichia coli* for production of lactic acid," *Biotechnol. Bioeng.* 91(5):643-648 (2005).

Fonknechten et al., "A conserved gene cluster rules anaerobic oxidative degradation of L-ornithine," *J. Bacteriol.* 191(9):3162-3167 (2009).

Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).

Fontaine et al., "A New Type of Glucose Fermentation by *Clostridium thermoaceticum* N.Sp.," *J. Bacteriol.* 43(6):701-715 (1942).

Ford et al., "Molecular properties of the lystl+ gene and the regulation of α-aminoadipate reductase in *Schizosaccharomyces pombe*," *Curr. Genet.* 28:131-137 (1995).

Forouhar et al., "Structural and Functional Evidence for *Bacillus subtilis* PaiA as a Novel $N^1$-Spermidine/spermine Acetyltransferase," *J. Biol. Chem.* 280(48):40328-40336 (2005).

Forster et al., "Genome-scale reconstruction of the *Saccharomyces cerevisiae* metabolic network," *Genome Res.* 13(2):244-253 (2003).

Fox et al., "Characterization of the region encoding the Co-induced hydrogenase of *Rhodospirillum rubrum*," *J. Bacteriol.* 178(21):6200-6208 (1996).

Freiberg et al., "Identification and characterization of the first class of potent bacterial acetyl-CoA carboxylase inhibitors with antibacterial activity," *J. Biol. Chem.* 279:26066-26073 (2004).

Freidrich et al., "The complete stereochemistry of the enzymatic dehydration of 4-hydroxybutyryl Coenzyme A to crotonyl Coenzyme A," *Angew. Chem. Int. Ed.* 47:3254-3257 (2008).

Frerman and Duncombe, "Studies on the subunits of *Escherichia coli* Coenzyme A transferase. Reconstitution of an active enzyme," *Biochim. Biophys. Acta* 580(2):289-297 (1979).

Fries et al., "Reaction Mechanism of the heterotetrameric ($\alpha_2\beta_2$) E1 Component of 2-Oxo Acid Dehydrogenase Multienzyme Complexes," *Biochemistry* 42:6996-7002 (2003).

Frost and Draths, "Synthesis of adipic acid from biomass-derived carbon sources," *Biotechnol Adv.* 15(1):294 (1997).

Frost et al., "Dehydroquinate synthase from *Escherichia coli*: purification, cloning, and construction of overproducers of the enzyme," *Biochemistry* 23:4470-4475 (1984).

Frost, "Redefining chemical manufacture. Replacing petroleum with plant-derived feedstocks," *Ind. Biotechnol.* 1(1):23-24 (2005).

Fu et al., "Crystal structures of human glutaryl-CoA dehydrogenase with and without an alternate substrate: structural bases of dehydrogenation and decarboxylation reactions," *Biochemistry* 43(30):9674-9684 (2004).

Fujii et al., "Characterization of L-lysine 6-aminotransferase and its structural gene from *Flavobacterium lutescens* IFO3084," *J. Biochem.* 128:391-397 (2000).

Fujii et al., "Error-prone rolling circle amplification: the simplest random mutagenesis protocol," *Nat. Protoc.* 1:2493-2497 (2006).

Fujii et al., "One-step random mutagenesis by error-prone rolling circle amplification," *Nucleic Acids Res.* 32:e145 (2004).

Fujii, T. et al. "Molecular Cloning, Sequence Analysis, and Expression of the Yeast Alcohol Acetyltransferase Gene," *Appl. Environ. Microbiol.* 60:2786-2792 (1994).

Fujishiro et al., "Crystallization and Some Properties of Acetylpolyamine Amidohydrolase From Mycoplana Bullata," *Biochem. Biophys. Res. Commun.* 157(3):1169-1174 (1988).

Fujita et al., "Novel Substrate Specificity of Designer 3-Isopropylmalate Dehydrogenase Derived from *Thermus thermophilus* HB8," *Biosci. Biotechnol. Biochem.* 65(12):2695-2700 (2001).

Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys. Acta* 1597:74-80 (2002).

Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 268:5639-5646 (2001).

Fukui et al., "Engineering of Ralstonia eutropha for production of poly(3-hydroxybutyrate-co-3-hydroxyhexanoate) from fructose and solid-state properties of the copolymer," *Biomacromolecules* 3(3):618-624 (2002).

Fukumura et al, "Hydrolysis of cyclic and linear oligomers of 6-aminocaproic acid by a bacterial cell extract," *J. Biochem.* 59(6):531-536 (1966).

Fukumura et al., "Purification and properties of a novel enzyme, L-α-amino-ε-caprolactamase from *Cryptococcus laurentii*," *FEBS Lett.* 89(2):298-300 (1978).

Fuller and Leadlay, "Proton transfer in methylmalonyl-CoA epimerase from *Propionibacterium shermanii*. The reaction of (2R)-methyl-malonyl-CoA in tritiated water," *Biochem. J.* 213(3):643-650 (1983).

Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).

Furukawa et al., "Increased alcohol acetyltransferase activity by inositol limitation in *Saccharomyces cerevisiae* in sake mash," *J. Biosci. Bioeng.* 96(4):380-386 (2003).

Galagan et al., "The genome of *M. acetivorans* reveals extensive metabolic and physiological diversity," *Genome Res.* 12(4):532-542 (2002).

Gallagher et al., "The crystal structure of chorismate lyase shows a new fold and a tightly retained product," *Proteins* 44:304-311 (2001).

Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).

Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys Acta* 1255(2):154-160 (1995).

Garvie, "Bacterial lactate dehydrogenases," *Microbiol. Rev.* 44:106-139 (1980).

Gay et al., "Cloning Structural Gene sacB, Which Codes for Exoenzyme Levansucrase of *Bacillus subtilis*: Expression of the Gene in *Escherichia coli*," *J. Bacteriol.* 153(3):1424-1431 (1983).

Genda et al., "Purification and characterization of fumarase from Corynebacterium glutamicum," *Biosci. Biotechnol. Biochem.* 70:1102-1109 (2006).

Gerhardt et al. "Fermentation of 4-aminobutyrate by Clostridium aminobutyricum: cloning of two genes involved in the formation dehydration of 4-hydroxybutyrl-CoA," *Arch. Microbiol.* 174:189-199 (2000).

Gerischer and Dürre, "mRNA Analysis of the *adc* Gene Region of *Clostridium acetobutylicum* during the Shift to Solventogenesis," *J. Bacteriol.* 174(2):426-433 (1992).

Gescher et al., "Genes coding for a new pathway of aerobic benzoate metabolism in *Azoarcus evansii*," *J Bacteriol.* 184(22):6301-6315 (2002).

Giaever et al., "Functional profiling of the *Saccharomyces cerevisiae* genome," *Nature* 418(6896):387-391 (2002).

Gibbs et al., "Degenerate olignucleotide gene shuffling (DOGS): a method for enhancing the frequence of recombination with family shuffling," *Gene* 271:13-20 (2001).

Gibson (née Thomas) et al., "Cross metathesis of the amino acid homoallylglycine," *Chem. Commun.* 1107-1108 (1997).

Gibson and McAlister-Henn, "Physical and genetic interactions of cytosolic malate dehydrogenase with other gluconeogenic enzymes," *J. Biol. Chem.* 278:25628-25636 (2003).

Giesel and Simon, "On the occurrence of enoate reductase and 2-oxo-carboxylate reductase in clostridia and some observations on the amino acid fermentation by *Peptostreptococcus anaerobius*," *Arch. Microbiol.* 135(1):51-57 (1983).

Gillyon et al., "Putrescine Breakdown in the Yeast Candida boidinii: Subcellular Location of Some of the Enzymes Involved and Properties of Two Acetamidoaldehyde Dehydrogenases," *J. of Gen. Microbiol.* 133:2477-2485 (1987).

Glasemacher et al., "Purification and properties of acetyl-CoA synthetase (ADP-forming), an archael enzyme of acetate formation and ATP synthesis, from the hyperthermophile *Pyrococcus furiosus*," *Eur. J. Biochem.* 244:561-567 (1997).

Gäbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).

Goda et al., "Cloning, sequencing, and expression in *Escherichia coli* of the Clostridium tetanomorphum gene encoding β-methylaspartase and characterization of the recombinant protein," *Biochemistry* 31(44):10747-10756 (1992).

Gokarn et al., "Expression of pyruvate carboxylase enhances succinate production in *Escherichia coli* without affecting glucose uptake," *Biotechnol. Lett.* 20:795-798 (1998).

Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).

Gokarn, et al., "The physiological effects and metabolic alterations caused by the expression of *Rhizobium etli* pyruvate carboxylase in *Escherichia coli*," *Appl. Microbiol. Biotechnol.* 56(1-2):188-195 (2001).

Gokulan et al., "Crystal structure of Mycobacterium tuberculosis diaminipimelate decarboxylase, an essential enzyme in bacterial lysine biosynthesis," *J. Biol. Chem.* 278(20):18588-18596 (2003).

Goldberg et al., "Improved Conversion of Fumarate to Succinate by *Escherichia coli* Strains Amplified for Fumarate Reductase," *Appl. Environ. Microbiol.* 45:1838-1847 (1983).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

González and Robb, "Genetic analysis of Carboxydothermus hydrogenoformans carbon monoxide dehydrogenase genes cooF and cooS," *FEMS Microbiol. Lett.* 191(2):243-247 (2000).

Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).

Gonzalez-Pajuelo et al., "Metabolic engineering of *Clostridium acetobutylicum* for the industrial production of 1,3-propanediol from glycerol," *Met. Eng.* 7:329-336 (2005).

Gordon and Doelle, "Purification, properties and immunological relationship of L(+)-lactate dehydrogenase from *Lactobacillus casei*," *Eur. J. Biochem.* 67:543-555 (1976).

Goupil et al., "Imbalance of Leucine Flux in *Lactococcus lactis* and Its Use for the Isolation of Diacetyl-Overproducing Strains," *Appl. Environ. Microbiol.* 62(7):2636-2640 (1996).

Goupil-Feuillerat et al., "Transcriptional and Translational Regulation of α-Acetolactate Decarboxylase of *Lactococcus lactis* subsp. Lactis," *J. Bacteriol.* 182(19):5399-5408 (2000).

Gourley et al., "The two types of 3-dehydroquinase have distinct structures but catalyze the same overall reaction," *Nat. Struct. Biol.* 6:521-525 (1999).

Grant and Patel. "The non-oxidative decarboxylation of p-hydroxybenzoic acid, gentisic acid, protocatechuic acid and gallic acid by *Klebsiella aerogenes* (*Aerobacter aerogenes*)," *Antonie Van Leeuwenhoek* 35:325-343 (1969).

Green and Bennett, "Genetic manipulation of acid and solvent formation in clostridium acetobutylicum ATCC 824," *Biotechnol. Bioeng.* 58(2-3):215-221 (1998).

Green and Nichols, "p-Aminobenzoate biosynthesis in *Escherichia coli*. Purification of aminodeoxychorismate lyase and cloning of pabC," *J. Biol. Chem.* 266:12971-12975 (1991).

Green et al., "Catabolism of α-ketoglutarate by a sucA mutant of Bradyrhizobium japonicum: evidence for an alternative tricarboxylic acid cycle," *J. Bacteriol.* 182:2838-2844 (2000).

Green et al., "Characterization and sequence of *Escherichia coli* pabC, the gene encoding aminodeoxychorismate lyase, a pyridoxal phosphate-containing enzyme," *J. Bacteriol.* 174:5317-5323 (1992).

Grethlein and Jain, "Bioprocessing of coal-derived synthesis gases by anaerobic bacteria," *Trends Biotech.* 10:418-423 (1992).

Grolle et al., "Isolation of the dxr gene of Zymomonas mobilis and characterization of the 1-deoxy-D-xylulose 5-phosphate reductoisomerase," *FEMS Microbiol. Lett.* 191:131-137 (2000).

Grubbs, "Olefin Meethathesis," *Tetrahedron* 60:7117-7140 (2004).

Gu et al., "Crystal structure of shikimate kinase from Mycobacterium tuberculosis reveals the dynamic role of the LID domain in catalysis," *J. Mol. Biol.* 319:779-789 (2002).

Gueldener et al., "A second set of *loxP* marker cassettes for Cre-mediated multiple gene knockouts in budding yeast," *Nucleic Acids Res.* 30(6):e23 (2002).

Guerra et al., "Role of transmembrane segment M8 in the biogenesis and function of yeast plasma-membrane $H^+$-ATPase," *Biochim. Biophys. Acta* 1768:2383-2392 (2007).

Guest et al., "The fumarase genes of *Escherichia coli*: location of the fumB gene and discovery of a new gene (fumC)," *J. Gen. Microbiol.* 131(11):2971-2984 (1985).

Guettler et al., "*Actinobacillus succinogenes* sp. nov., a novel succinic-acid-producing strain from the bovine rumen," *Int. J. Syst. Bacteriol.* 49:207-216 (1999).

Guirard and Snell, "Purification and properties of ornithine decarboxylase from *Lactobacillus* sp. 30a," *J. Biol. Chem.* 255:5960-5964 (1980).

Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from Schizosaccharomyces pombe," *Yeast* 21:1279-1288 (2004).

Guo and Bhattacharjee, "Site-directed mutational analysis of the novel catalytic domains of α-aminoadipate reductase (Lys2p) from *Candida albicans*," *Mol. Gen. Gemonics* 269:271-279 (2003).

Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).

Gutierrez et al., "A mutant D-amino acid aminotransferase with broad substrate specificity: construction by replacement of the interdoman loop Pro119-Arg120-Pro121 by Gly-Gly-Gly," *Protein Eng.* 11:53-58 (1998).

Gutknecht et al., "The dihydroxyacetone kinase of *Escherichia coli* utilizes a phosphoprotein instead of ATP as phosphoryl donor," *EMBO J.* 20(10):2480-2486 (2001).

Guyer et al., "Identification of a sex-factor-affinity site in *E. coli* as γδ," *Cold Spring Harbor Symp. Quant. Biol.* 45:135-140 (1981).

Guzman et al., "Tight regulation, modulation, and high-level expression by vectors containing the arabinose $P_{BAD}$ promoter," *J. Bacterio.* 177:4121-4130 (1995).

Haarasilta and Oura, "On the activity and regulation of anaplerotic and gluconeogenetic enzymes during the growth process of baker's yeast. The biphasic growth," *Eur. J. Biochem.* 52:1-7 (1975).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).

Hahm et al., "Characterization and evaluation of a pta (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hambraeus and Nyberg, "Enzymatic Hydrogenation of trans-2-Nonenal in Barley," *J. Agric. Food Chem.* 53:8714-8721 (2005).

Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).

Han et al., "Biochemical characterization and inhibitor discovery of shikimate dehydrogenase from *Helicobacter pylori*," *FEBS J.* 273:4682-4692 (2006).

Hanai et al., "Engineered synthetic pathway for isopropanol production in *Escherichia coli*," *Appl. Environ. Microbiol.* 73(24):7814-7818 (2007).

Hansford, "Control of mitochondrial substrate oxidation," *Curr. Top Bioenergy* 10:217-278 (1980).

Harder, "Anaerobic degradation of cyclohexane-1,2-diol by a new *Azoarcus* species," *Arch. Microbiol.* 168:199-204 (1997).

Hardison et al., "Globin Gene Server: A prototype E-Mail Database Server Featuring Extensive Multiple Alignments and Data Compilation for Electronic Genetic Analysis," *Genomics* 21:344-353 (1994).

Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).

Harms and Thauer, "Methylcobalamin: Coenzyme M methyltransferase isoenzymes MtaA and MtbA from Methanosarcina barkeri. Cloning, sequencing and differential transcription of the encoding genes, and functional overexpression of the mtaA gene in *Escherichia coli*," *Eur. J. Biochem.* 235(3):653-659 (1996).

Harrison and Harwood, "The pimFABCDE operon from *Rhodopseudomonas palustris* mediates dicarboxylic acid degradation and participates in anaerobic benzoate degradation," *Microbiology* 151:727-736 (2005).

Hartel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood and Parales, "The β-ketoadipate pathway and the biology of self-identity," *Annu. Rev. Microbiol.* 50:553-590 (1996).

Harwood et al., "Anaerobic metabolism of aromatic compounds via the benzoyl-CoA pathway," *FEMS Microbiol. Rev.* 22:439-458 (1999).

Harwood et al., "Identification of the pcaRKF Gene cluster from *Pseudomonas putida*: Involvement in Chemotaxis, Biodegradation, and Transport of 4-Hydroxybenzoate," *J. Bacteriol.* 176(21):6479-6488 (1994).

Hasan and Nester, "Dehydroquinate synthase in *Bacillus subtilis*. An enzyme associated with chorismate synthase and flavin reductase," *J. Biol. Chem.* 253:4999-5004 (1978).

Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (pofK) gene from *Klebsielss oxytoca* and its constitutive expression in *Escherichia coli* JM109 cells," *Biosci. Biotech. Biochem.* 58(1):217-218 (1994).

Hashimoto et al., "Activation of L-Lysine ε-Dehydrogenase from *Agrobacterium tumefaciens* by Several Amino Acids and Monocarboxylates," *J. Biochem.* 106:76-80 (1989).

Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from *Serratia marcescens*," *Biosci. Biotechnol. Biochem.* 64:1477-1485 (2000).

Hatakeyama et al., "Gene Cloning and Characterization of Maleate cis-trans Isomerase from *Alcaligenes faecalis*," *Biochem. Biophys. Res. Comm.* 239:74-79 (1997).

Hawes et al., "Primary structure and tissue-specific expression of human β-hydroxyisobutyryl-Coenzyme A hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from *Fusobacterium*," *J. Nihon. Univ. Sch. Dent.* 28(1):12-21 (1986).

Hayden et al., "Glutamate dehydrogenase of *Halobacterium salinarum*: evidence that the gene sequence currently assigned to the $NADP^+$-dependent enzyme is in fact that of the $NAD^+$-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. U.S.A.* 99(25):15926-15931 (2002).

Hayes et al., "The Biofine Process: Production of Levulinic Acid, Furfural and Formic Acid from Lignocellulosic Feedstocks," In *Biorefineries: Industrial Proceses and Products* Wiley, Weinheim, Germany, 139-164. (2006).

Haywood and Large, "4-Acetamidobutyrate Deacetylase in the Yeast Candida boidinii Grown on Putrescine or Spermidine as Sole Nitrogen, Source and Its Probable Role in Polyamine Catabolism," *J. Gen. Microbiol.* 132:7-14 (1986).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*," *Eur. J Biochem.* 229:77-82 (1995).

Heidlas and Tressl, "Purification and Properties of two oxidoreductases catalyzing the enantioselective reduction of diacetyl and other diketones from baker's yeast," *Eur. J. Biochem.* 188:165-174 (1990).

Heipieper and Isken, "Ethanol tolerance and membrane fatty acid adaptation in adh multiple and null mutants of *Kluyveromyces lactis*," *Res. Microbiol.* 151:(9):777-784 (2000).

Helin et al., "The refined x-ray structure of muconate lactonizing enzyme from *Pseudomonas putida* PRS2000 at 1.85 Å resolution," *J. Mol. Biol.* 254:918-941 (1995).

Heller et al., "Cloning and expression of the gene for the vitamin $B_{12}$ receptor protein in the outer membrane of *Escherichia coli*," *J. Bacteriol.* 161:896-903 (1985).

Hemschemeier et al., "Biochemical and physiological characterization of the pyruvate formate-lyase Pfl1 of *Chlamydomonas reinhardtii*, a typically bacterial enzyme in eukaryotic alga," *Eukaryot. Cell* 7:518-526 (2008).

Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy et al., "The reactivity of gamma-hydroxybutyric acid (GHB) and gamma-butyrolactone (GBL) in alcoholic solutions," *J. Forensic. Sci.* 49(6):1220-1229 (2004).

Henning et al., "Identification of novel benzoylformate decarboxylases by growth selection," *Appl. Environ. Microbiol.* 72:7510-7517 (2006).

Henriksson et al., "The 1.9 Å resolution structure of *Mycobacterium tuberculosis* 1-deoxy-D-xylulose 5-phosphate reductoisomerase, a potential drug target," *Acta. Crystallogr. D. Biol. Crystallogr.* 62(Pt 7):807-813 (2006).

Henstra et al., "Microbiology of synthesis gas fermentation for biofuel production," *Curr. Opin. Biotechnol.* 18:200-206 (2007).

Hermes et al., "Searching sequence space by definably random mutagenesis: Improving the catalytic potency of an enzyme," *Proc. Natl. Acad. Sci U.S.A.* 87:696-700 (1990).

Herrmann et al., "Energy Conservation via Electron-Transferring Flavoprotein in Anaerobic Bacteria," *J. Bacteriol.* 190(3):784-791 (2008).

Herrmann et al., "Two β-alanyl-CoA:ammonia lyases in *Clostridium propionicum*," *FEBS J.* 272:813-821 (2005).

Hespell et al., "Stabilization of pet Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Hester et al., "Purification of active E1$\alpha_2\beta_2$ of *Pseudomonas putida* branched-chain-oxoacid dehydrogenase," *Eur. J. Biochem.* 233:828-836 (1995).
Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).
Heydari et al., "Highly Stable L-Lysine 6-Dehydrogenase from the thermophile *Geobacillus stearothermophilus* Isolated from a Japanese Hot Spring: characterization, Gene Cloning and sequencing, and Expression," *Appl. Environ. Microbiol.* 70(2):937-942 (2004).
Hibbert et al., "Directed evolution of biocatalytic processes," *Biomol. Eng.* 22:11-19 (2005).
Highbarger et al., "Mechanism of the reaction catalyzed by acetoacetate decarboxylase. Importance of lysine 116 in determining the $pK_a$ of active-site lysine 115," *Biochemistry* 35(1):41-46 (1996).
Hijarrubia et al., "Domain Structure Characterization of the Multifunctional $\alpha$-Aminoadipate Reductase from *Penicillium chrysogenum* by Limited Proteolysis," *J. Biol. Chem.* 278(10):8250-8256 (2003).
Hill et al., "PCR based gene engineering of the *Vibrio harveyi* lux operon and the *Escherichia coli* trp operon provides for biochemically functional native and fused gene products," *Mol. Gen. Genet.* 226:41-48 (1991).
Hillmer and Gottschalk, "Particulate Nature of Enzymes Involved in the Fermentation of Ethanol and Acetate by *Clostridium kluyveri*," *FEBS Lett.* 21(3):351-354 (1974).
Hillmer and Gottschalk, "Solubilization and partial characterization of particulate dehydrogenases from *Clostridium kluyveri*," *Biochim. Biophys. Acta* 334:12-23 (1974).
Hirano et al., "Purification and characerization of the Alcohol Dehydrogenase with a Broad Substrate Specificy Originated from 2-Phenylethanol-Assimilating *Brevibacterium* sp. KU 1309," *J. Biosci. Bioeng.* 100(3): 318-322 (2005).
Hirata et al., "Stereochemistry of reduction of the endocyclic double bond of (−)-carvone with the enzyme preparation from cultured cells of *Nicotiana tabacum*," *Phytochemistry* 28(12):3331-3333 (1989).
Hiser et al., "ERG10 from *Saccharomyces cerevisiae* encodes acetoacetyl-CoA thiolase," *J. Biol. Chem.* 269:31383-31389 (1994).
Ho et al., "Regulation of serine biosynthesis in *Arabidopsis*. Crucial role of plastidic 3-phosphoglycerate dehydrogenase in non-photosynthetic tissues," *J. Biol. Chem.* 274:397-402 (1999).
Hoang et al., "A broad-host-range Flp-FRT recombination system for site-specific excision of chromosomally-located DNA sequences: application for isolation of unmarked *Pseudomonas aeruginosa* mutants," *Gene* 212(1):77-86 (1998).
Hoffmann and Dimroth, "Sterochemistry of the methylmalonyl-CoA decarboxylation reaction," *FEBS Lett.* 220:121-125 (1987).
Hoffmeister et al., "Mitochondrial trans-2-enoyl-CoA reductase of wax ester fermentation from *Euglena gracilis* defines a new family of enzymes involved in lipid synthesis," *Biol. Chem.* 280(6):4329-4338 (2005).
Hofmeister and Buckel, "(R)-lactyl-CoA dehydratase from Clostridium propionicum. Stereochemistry of the dehydration of (R)-2-hydroxybutyryl-CoA to crotonly-CoA," *Eur. J. Biochem.* 206(2):547-552 (1992).
Hofmeister et al., "Cloning and expression of the two genes coding for L-serine dehydratase from Peptostreptococcus asaccharolyticus: relationship of the iron-sulfur protein to both L-serine dehydratases from *Escherichia coli*," *J. Bacteriol.* 179(15):4937-4941 (1997).
Hogan et al., "Improved Specificity toward Substrates with Positively Charged Side chains by Site-Directed Mutagenesis of the L-Lactate Dehydrogenase of *Bacillus stearothermophilus*," *Biochemistry* 34:4225-4230 (1995).
Holloway and Marsh, "Adenosylcobalamin-dependent glutamate mutase from Clostridium tetanomorphum. Overexpression in *Escherichia coli*, purification, and characterization of the recombinant enzyme," *J. Biol. Chem.* 269(32):20425-20430 (1994).
Holms, "The central metabolic pathways in *Escherichia coli*: relationship between flux and control at a branch point, efficiency of conversion to biomass, and excretion of acetate," *Curr. Top Cell. Regul.* 28:69-105 (1986).
Hong and Lee, "Metabolic flux analysis for succinic acid production by recombinant *Escherichia coli* with amplified malic enzyme activity," *Biotechnol. Bioeng.* 74(2):89-95 (2001).
Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).
Hong et al., "The genome sequence of the capnophilic rumen bacterium Mannheimia succiniciproducens." *Nat. Biotechnol.* 22(10):1275-1281 (2004).
Hong et al., "Importance of redox balance on the production of succinic acid by metabolically engineered *Escherichia coli*," *Appl. Microbiol. Biotechnol.* 58:286-290 (2002).
Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).
Howard et al., "Titanium Metallacarbene-Metallacylobutane Reactions: Stepwise Metathesis," *J. Am. Chem. Soc.* 102:6876-6878 (1980).
Hsu et al., "Expression of an aromatic-dependent decarboxylase which provides growth-essential $CO_2$ equivalents for the acetogenic (Wood) pathway of *Clostridium thermoaceticum*," *J. Bacteriol.* 172:5901-5907 (1990).
Hu et al., "The catalytic intermediate stabilized by a "down" active site loop for diaminopimelate decarboxylase from *Helicobacter pylori*. Enzymatic characterization with crystal structure analysis," *J. Biol. Chem.* 283(30):21284-21293 (2008).
Huang et al., "Genetic characterization of the resorcinol catabolic pathway in Corynebacterium glutamicum," *Appl. Environ. Microbiol.* 72:7238-7245 (2006).
Huang et al., "Purification and characterization of a ferulic acid decarboxylase from *Pseudomonas fluorescens*," *J. Bacteriol.* 176:5912-5918 (1994).
Huang et al., "Identification and characterization of a second butyrate kinase from *Clostridium acetobutylicum* ATCC 824," *J. Mol. Microbiol. Biotechnol.* 2(1):33-38 (2000).
Hübner et al., "The mechanism of substrate activation of pyruvate decarboxylase: A first approach," *Eur. J. Biochem.* 92:175-181 (1978).
Huder and Dimroth, "Sequence of the sodium ion pump methylmalonyl-CoA decarboxylase from *Veillonella parvula*," *J. Biol. Chem.* 268:24564-24571 (1993).
Hughes et al., "Cloning and expression of pca genes from *Pseudomonas putida* in *Escherichia coli*," *J. Gen. Microbiol.* 134:2877-2887 (1988).
Hughes et al.," Evidence for isofunctional enzymes in the degradation of phenol, m- and p-toluate, and p-cresol via catechol metacleavage pathways in Alcaligenes eutrophus," *J. Bacteriol.* 158(1):79-83 (1984).
Hugler et al., "Malonyl-Coenzyme a Reductase from *Chloroflexus aurantiacus*, a Key Enzyme of the 3-Hydroxypropionate Cycle for Autotrophic CO2 Fixation," *J. Bacteriol.* 184(9):2404-2410 (2002).
Huh et al., "Global analysis of protein localization in budding yeast," *Nature* 425:686-691 (2003).
Huisman and Lalonde, "Enzyme evolution for chemical process applications," In R.N. Patel (ed.), *Biocatalysis in the pharmaceutical and biotechnology industries*, CRC Press, p. 717-742 (2007).
Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).

Hustede et al., "Cloning of poly(3-hydroxybutyric acid) synthase genes of *Rhodobacter sphaeroides* and Rhodospirillum rubum and heterologous expression in Alcaligenes eutrophys," *FEMS Microbiol. Lett.* 93:285-290 (1992).

Ibarra et al., "*Escherichia coli* K-12 undergoes adaptive evolution to achieve in silico predicted optimal growth," *Nature* 420(6912):186-189 (2002).

Ichikawa et al., "Catalytic reaction of 1,3-butanediol over solid acids," *J. Mol. Catalysis A Chem.* 256:106-112 (2006).

Ichikawa et al., "PIO study on 1,3-butanediol dehydration over $CeO_2$ (1 1 1) surface," *J. Mol. Catalysis A Chem.* 231:181-189 (2005).

Iffland et al., "Directed Molecular Evolution of Cytochrome *c* Peroxidase," *Biochemistry* 39:10790-10798 (2000).

Ikai and Yamamoto, "Identification and analysis of a gene encoding L-2,4-diaminobutyrate:2-ketoglutarate 4-aminotransferase involved in the 1,3-diaminopropane production pathway in Acinetobacter baummanni," *J. Bacteriol.* 179:5118-5125 (1997).

Imai and Ohno, "Measurement of yeast intracellular pH by image processing and the change it undergoes during growth phase," *J.Biotechnol.* 38:165-172 (1995).

Ingoldsby et al., "The discovery of four distinct glutamate dehydrogenase genes in a strain of *Halobacterium salinarum*," *Gene* 349:237-244 (2005).

Ingram and Vreeland, "Differential-Effects of Ethanol and Hexanol on the *Escherichia-coli* Cell-Envelope," *J. Bacteriol.* 144:481-488 (1980).

Inui et al., "Occurrence of Oxygen-Sensitive, $NADP^+$-Dependent Pyruvate-Dehydrogenase in Mitochondria of *Euglena-gracilis*," *J. Biochem.* 96:931-934 (1984).

Inui et al., "Pyruvate-$NADP^+$ Oxidoreductase from *Euglena-gracilis*—the Kinetic-Properties of the Enzyme," *Arch. Biochem Bipophys.* 274:434-442 (1989).

Inui et al., "Wax Ester Fermentation in *Euglena-gracilis*," *FEBS Lett.* 150:89-93 (1982).

Inui et al., "Fatty acid synthesis in mitochondria of *Euglena gracilis*," *Euro. J. Biochem.* 142(1):121-126 (1984).

Inui et al., "Production and Composition of Wax Esters by Fermentation of *Euglena gracilis*," *Agr. Biol. Chem.* 47(11):2669-2671 (1983).

Inui et al., "Purification and characterization of pyruvate:$NADP^+$ oxidoreductase in *Euglena gracilis*," *J. Biol. Chem.* 262(19):9130-9135 (1987).

Inui et al., "Pyruvate:$NADP^+$ oxidoreductase from *Euglena gracilis*: mechanism of $O_2$-inactivation of the enzyme and its stability in the aerobe," *Arch. Biochem. Biophys.* 280:292-298 (1990).

Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).

Ishida et al., "Efficient production of L-Lactic acid by metabolically engineered *Saccharomyces cerevisiae* with a genome-integrated L-lactate dehydrogenase gene," *Appl. Envirom. Microbiol.* 71:1964-1970 (2005).

Ishige et al., "Long-chain aldehyde dehydrogenase that participates in n-alkane utilization and wax ester synthesis in *Acinetobacter* sp. strain M-1," *Appl. Environ. Microbiol.* 66:3481-3486 (2000).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2005).

Ito and Yanofsky, "Anthranilate synthetase, an enzyme specified by the tryptophan operon of *Escherichia coli*: Comparative studies on the complex and the subunits," *J. Bacteriol.* 97:734-742 (1969).

Ito et al., "Colistin nephrotoxicity: report of a case with light and electron microscopic studies," *Acta. Pathol. Jpn.* 19:55-67 (1969).

Ito et al., "D-3-hydroxybutyrate dehydrogenase from *Pseudomonas fragi*: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Iwakura et al., "Studies on regulatory functions of malic enzymes. VI. Purification and molecular properties of NADP-linked malic enzyme from *Escherichia coli* W," *J. Biochem.* 85:1355-1365 (1979).

Izard and Blackwell, "Crystal structures of the metal-dependent 2-dehydro-3-deoxy-galacarate aldolase suggest a novel reaction mechanism," *EMBO J.* 19:3849-3856 (2000).

Izumi et al., "Structure and Mechanism of HpcG, a Hydratase in the Homoprotocatechuate Degradation Pathway of *Escherichia coli*," *J. Mol. Biol.* 370:899-911 (2007).

Jacobi et al., "The hyp operon gene products are required for the maturation of catalytically active hydrogenase isoenzymes in *Escherichia coli*," *Arch. Microbiol.* 158(6):444-451 (1992).

Jacques et al., "Characterization of yeast homoserine dehydrogenase, an antifungal target: the invariant histidine 309 is important for enzyme integrity," *Biochem. Biophys. Acta* 1544:28-41 (2001).

Jäger and Färber, "Die Alanatreduktion von β-Carbonyl-oxalylsäure-estern," *Chem. Ber.* 92:2492-2499 (1959).

James and Cronan, "Expression of two *Escherichia coli* acetyl-CoA carboxylase subunits is autoregulated," *J. Biol. Chem.* 279:2520-2527 (2004).

James and Viola, "Production and characterization of bifunctional enzymes. Domain swapping to produce new bifunctional enzymes in the aspartate pathway," *Biochemistry* 41(11) 3720-3725 (2002).

Jansen and Wanders, "L-2-hydroxyglutarate dehydrogenase: identification of a novel enzyme activity in rat and human liver. Implications for L-2-hydroxyglutaric academia," *Biochim. Biophys. Acta* 1225(1):53-56 (1993).

Janssen, "Propanol as an end product of theonine fermentation," *Arch. Microbiol.* 182:482-486 (2004).

Jantama et al., "Combining metabolic engineering and metabolic evolution to develop nonrecombinant strains of *Escherichia coli* C that produce succinate and malate," *Biotechnol. Bioeng.* 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Javid-Majd and Blanchard, "Mechanistic Analysis of the argE-Encoded N-Acetylornithine Deacetylase," *Biochemistry* 39:1285-1293 (2000).

Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jennert et al., "Gene transfer to *Clostridium cellulolyticum* ATCC 35319," *Microbiol.* 146:3071-3080 (2000).

Jenssen et al., "A literature network of human genes for high-throughput analysis of gene expression," *Nat. Gene.* 28:21-28 (2001).

Jeon et al., "Heterologous expression of the alcohol dehydrogenase (adhl) gene from Geobacillius thermoglucosidasius strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jiang et al., "De Novo Computational Design of Retro-Aldol Enzymes," *Science* 319:1387-1391 (2008).

Jin and Sonenshein, "Characterization of the major citrate synthase of *Bacillus subtilis*," *J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Johnston et al., "Structure of naphthoate synthase (MenB) from *Mycobacterium tuberculosis* in both native and product-bound forms," *Acta. Crystallogr. D. Biol. Crystallogr.* 61(Pt 9):1199-1206 (2005).

Jojima et al., "Production of isopropanol by metabolically engineered *Escherichia coli*," *Appl. Microbiol. Biotechnol.* 77:1219-1224 (2008).

Jones and Woods, "Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kahng et al., "Characterization of strain HY99, a novel microorganism capable of aerobic and anaerobic degradation of aniline," *FEMS Microbiol. Lett.* 190:215-221 (2000).

Kai et al., "Phosphoenol pyruvate carboxylase: three-dimensional structure and molecular mechanisms," *Arch. Biochem. Biophys.* 414:170-179 (2003).

Kakimoto et al., "β-aminoisobutyrate-α-ketoglutarate transaminase in relation to β-aminoisobutyric aciduria," *Biochim. Biophys. Acta* 156(2):374-380 (1968).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalpos, "On the mammalian acetone metabolism: from chemistry to clinical implications," *Biochim. Biophys. Acta* 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in Acinetobacter calcoaceticus ADP1," *J. Biol. Chem.* 278(10):8075-8082 (2003).

Kalscheuer et al., "Analysis of storage lipid accumulation in Alcanivorax borkumensis: Evidence for alternative triacylglycerol biosynthesis routes in bacteria," *J. Bacteriol.* 189(3):918-928 (2007).

Kanagawa et al., "Characterization of the 6-aminohexanoate-dimer hydrolase from *Pseudomonas* sp. NK87," *J. Gen. Microbiol.* 139(4):787-795 (1993).

Kanamasa et al., "Cloning and functional characterization of the cis-aconitic acid decarboxylase (CAD) gene from *Aspergillus terreus*," *Appl. Microbiol. Biotechnol.* 80(2):223-229 (2008).

Kanao et al., "Characterization of isocitrate dehydrogenase from the green sulfur bacterium *Chlorbium limicola*. A carbon dioxide-fixing enzyme in the reductive tricarboxylic acid cycle," *Eur. J. Biochem.* 269(7):1926-1931 (2002).

Kanaujia et al., "Cloning, expression, purification, crystallization and preliminary X-ray crystallographic study of DHNA synthetase from *Geobacillus kaustophilus*," *Acta. Crystallogr. Sect. F. Struct. Biol. Cryst. Commun.* 63(Pt 2):103-105 (2007).

Kanehisa and Goto, "KEGG: Kyoto Encyclopedia of Genes and Genomes database," *Nucleic Acids Res.* 28(1):27-30 (2000).

Kapatral et al., "Genome Sequence and Analysis of the Oral Bacterium Fusobacterium nucleatum Strain ATCC 25586," *J. Bacteriol.* 184(7):2005-2018 (2002).

Karyakin et al., "Kinetic properties of L-lysine-2-monooxygenase from *Pseufomonas putida* and its application to biosensors for L-lysine," *Prikladnaya Biokhimiya I Mikrobiologiva* 27:825-832 (1991).

Kasberg et al., "Cloning, characterization, and sequence analysis of the clcE gene encoding the maleylacetate reductase of *Pseufomonas* sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

Kaschabek and Reineke, "Maleylacetate reductase of *Pseufomonas* sp. Strain B13: specificity of substrate conversion and halide elimination," *J. Bacteriol.* 177:320-325 (1995).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).

Kashket and Cao, "Isolation of a Degeneration-Resistant Mutant of clostridium acetobutylicum NCIMB 8052," *Appl. Environ. Microbiol.* 59:4198-4202 (1993).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Katti et al., "Crystal structure of muconolactone isomerase at 3.3 Å resolution," *J. Mol. Biol.* 205:557-571 (1989).

Katz et al., "Screening of two complementary collections of *Saccharomyces cerevisiae* to identify enzymes involved in stereo-selective reductions of specific carbonyl compounds: an alternative to protein purification," *Enzyme Microb. Technol.* 33:163-172 (2003).

Kawabata et al., "The Effect of Growth Temperature on Wax Ester Content and Composition of *Euglena gracilis*," *J. Gen. Microbiol.* 135: 1461-1467 (1989).

Kazahaya et al, "Aerobic Dissimilation of Glucose by Heterolactic Bacteria III. Aldehyde dehydrogenase and alcohol dehydrogenase of luconostoc mesenteroids," *J. Gen. Appl. Microbiol.* 18(1):43-55 (1972).

Kefala et al., "Cloning, expression, purification, crystallization and preliminary x-ray diffraction analysis of LysA (Rv1293) from *Mycobacterium tuberculosis*," *Acta. Crystallogr. Sect. F. Struct. Biol. Cryst. Commun.* 61 (Pt 8):782-784 2005.

Kellum and Drake, "Effects of cultivation gas phase on hydrogenase of the acetogen *Clostridium thermoaceticum*," *J. Bacteriol.* 160(1):466-469 (1984).

Kenealy et al., "Biochemical Aspects of Fumaric Acid Accumulation by *Rhizopus arrhizus*," *Appl. Environ. Microbiol.* 52:128-133 (1986).

Keng and Viola, "Specificity of Aspartokinase III from *Escherichia coli* and Examination of Important Catalytic Residues," *Arch. Biochem. Biophys.* 335(1):73-81 (1996).

Kenklies et al., "Proline biosynthesis from L-ornithine in Clostridium sticklandii: purification of $\Delta^1$-pyrroline-5-carboxylate reductase, and sequence and expression of encoding gene, proC," *Microbiology* 145(Pt 4):819-826 (1999).

Kerby et al., "Carbon Monoxide-Dependent Growth of *Rhodospirillum rubrum*," *J. Bacteriol.* 177:2241-2244 (1995).

Kerby et al., "Genetic and physiological characterization of the *Rhodospirillum rubrum* carbon monoxide dehydrogenase system," *J. Bacteriol.* 174(16):5284-5294 (1992).

Kern et al., "Isoamyl alcohol-induced morphological change in *Saccharomyces cerevisiae* involves increases in mitochondria and cell wall chitin content," *FEMS Yeast Res.* 5:43-49 (2004).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Khan et al., "Molecular Properties and Enhancement of Thermostability by Random Mutagenesis of Glutamate Dehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al, "Effect of Overexpression of Actinobacillus succinogenes Phosphoenolpyruvate Carboxykinase on Succinate Production in *Escherichia coli*," *Appl. Env. Microbiol.* 70(2) 1238-1241 (2004).

Kim et al., "2-Hydroxyisocaproyl-CoA dehydratase and its activator from *Clostridium difficile*," *FEBS J.* 272:550-561 (2005).

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).

Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).

Kim et al., "Studies of the hyperthermophile *Thermotoga maritima* by random sequencing of cDNA and genomic libraries. Identification and sequencing of the trpEG (D) operon," *J. Mol. Biol.* 231:960-981 (1993).

Kim, "Purification and Properties of a diamine α-Ketoglutarate Transminase from *Escherichia coli*," *J. Biol. Chem.* 239(3):783-786 (1964).

Kino et al. Synthesis of DL-tryptophan by modified broad specificity amino acid racemase from *Pseudomonas putida* IFO 12996, *Appl. Microbiol. Biotechnol.* 73:1299-1305 (2007).

Kinoshita et al., "Purification and characterization of 6-aminohexanoic-acid-oligomer hydrolase of *Flavobacterium* sp. KI72," *Eur. J. Biochem.* 116(3):547-551 (1981).

Kinoshita, "Purification of two alcohol dehydrogenases from *Zymomonas mobilis* and their properties," *Appl. Microbiol. Biotechnol.* 22:249-254 (1985).

Kisselev L., "Polypeptide release factors in prokaryotes and eukaryotes: same function, different structure," *Structure* 10:8-9 (2002).

Klasson, et al., "Biological conversion of coal and coal-derived synthesis gas," *Fuel* 72(12):1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

Kleanthous et al., "A comparison of the enzymological and biophysical properties of two distinct classes of dehydroquinase enzymes," *Biochem. J.* 282(Pt3):687-695 (1992).

Klyosov, "Kinetics and specificity of human liver aldehyde dehydrogenases toward aliphatic, aromatic, and fused polycyclic aldehydes," *Biochemistry* 35(14):4457-4467 (1996).

Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Knappe et al., "Post-translational activation introduces a free radical into pyruvate formate-lyase," *Proc. Natl. Acad. Sci. U.S.A.* 81:1332-1335 (1984).

Knothe, "'Designer' Biodiesel: Optimizing Fatty Ester Composition to Improve Fuel Properties," *Energy Fuels* 22:1358-1364 (2008).

Kobayashi et al., "Physicochemical, catalytic, and immunochemical properties of fumarases crystallized separately from mitochondrial and cytosolic fractions of rat liver," *J. Biochem.* 89(6):1923-1931 (1981).

Koch and Fuchs, "Enzymatic reduction of benzoyl-CoA to alicyclic compounds, a key reaction in anaerobic aromatic metabolism," *Eur. J. Biochem.* 205:195-202 (1992).

Koch et al., "Products of enzymatic reduction of benzoyl-CoA, a key reaction in anaerobic aromatic metabolism," *Eur. J. Biochem.* 211:649-661 (1993).

Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).

Kollmann-Koch et al.,"Nicotinic acid metabolism. Dimethylmaleate hydratase," *Hoppe Seylers Z Physiol Chem.* 365:s.847-857 (1984).

Koo et al., "Cloning and characterization of the bifunctional alcohol/acetaldehyde dehydrogenase gene (adhE) in *Leuconostoc mesenteroides* isolated from kimchi," *Biotechnol. Lett.* 27(7):505-510 (2005).

Korbert et al., "Crystallization of the NADP$^+$-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase α-subunit structure using 3.4 Å MAD and 1.9 Å native data," *Acta. Crystallogr. D. Biol. Crystallogr.* 58(Pt 12):2116-2121 (2002).

Korotkova and Lidstrom, "Connection between poly-β-hydroxybutyrate biosynthesis and growth on $C_1$ and $C_2$ compounds in the methylotroph *Methylobacterium extorquens* AM1," *J. Bacteriol.* 183(3):1038-1046 (2001).

Korotkova and Lidstrom, "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium *Thermotoga maritima*: molecular characterization and phylogenetic implications," *Extremorhiles* 1:52-60 (1997).

Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver D-Methylmalonyl Coenzyme A Hydrolase," *J. Biol. Chem.* 258(18):11415-11421 (1983).

Kowalchuk et al., "Contrasting patterns of evolutionary divergence within the Acinetobacter calcoaceticus pca operon," *Gene* 146:23-30 (1994).

Kraus et al., "Biosynthesis and mitochondrial processing of the β subunit of propionyl Coenzyme A carboxylase from rat liver," *J. Biol. Chem.* 258:7245-7248 (1983).

Kreimeyer et al., "Identification of the Last Unknown Genes in the Fermentation Pathway of Lysine," *J. Biol. Chem.* 282(10):7191-7197 (2007).

Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).

Kress et al., "Tungsten(VI) and molybdenum(VI) oxo-alkyl species. Their role in the metathesis of olefins," *J. Chem. Soc. Chem. Commun.* 431-432 (1980).

Kretz et al., "Gene site saturation mutagenesis: a comprehensive mutagenesis approach," *Methods Enzymol.* 388:3-11 (2004).

Krieger et al., "Pyruvate decarboxylase from *Kluyveromyces lactis* an enzyme with an extraordinary substrate activation behaviour," *Eur. J. Biochem.* 269:3256-3263 (2002).

Krishna et al., "Enzymatic synthesis of isoamyl acetate using immobilized lipase from *Rhizomucor miehei*," *J. Biotechnol.* 87:193-201 (2001).

Kuchta and Abeles, "Lactate Reduction in *Clostridium propionicum* Purification and properties of lactyl-CoA dehydratase," *J. Biol. Chem.* 260(24):13181-13189 (1985).

Kühnl et al., "Functional analysis of the methylmalonyl-CoA epimerase from *Caenorhabditis elegans*," *FEBS J.* 272(6):1465-1477 (2005).

Kulkarni and Kanekar, "Bioremediation of ε-caprolactum from nylon-6 waste water by use of *Pseudomonas aeruginosa* MCM B-407," *Curr. Microbiol.* 37(3):191-194 (1998).

Kumamaru et al., "Enhanced degradation of polychlorinated biphenyls by directed evolution of biphenyl dioxygenase," *Nat. Biotechnol.* 16:663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kurihara et al., "γ-Glutamyputrescine synthetase in the putrescine utilization pathway of *Escherichia coli* K-12," *J. Biol. Chem.* 283(29)19981-19990 (2008).

Kurihara et al., "A Novel Putrescine Utilization Pathway Involves γ-Glutamylated Intermediates of *Escherichia coli* K-12," *J. Biol. Chem.* 280(6):4602-4608 (2005).

Kuznetsova et al., "Enzyme genomics: Application of general enzymatic screens to discover new enzymes," *FEMS Microbiol. Rev.* 29(2):263-279 (2005).

Kwok and Hanson, "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium *Thauera aromatica*," *Eur. J. Biochem.* 263(2):420-429 (1999).

Laivenieks et al., "Cloning sequencing, and overexpression of the *Anaerobiospirillum succiniciproducens* phosphoenolpyruvate carboxykinase (*pckA*) gene," *Appl. Environ. Microbiol.* 63:2273-2280 (1997).

Lam and Winkler, "Metabolic Relationships between Pyridoxine (Vitamin $B_6$) and Serine Biosynthesis in *Escherichia coli* K-12," *J. Bacteriol.* 171(11):6518-6528 (1990).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem. J.* 395(1):147-155 (2006).

Lamed and Zeikus, "Novel NADP-linked alcohol-aldehyde/ketone oxidoreductase in thermophilic ethanologenic bacteria," *Biochem. J.* 195:183-190 (1981).

Lardizabal et al., "Purification of a jojoba embryo wax synthase, cloning of its cDNA, and production of high levels of wax in seeds of transgenic arabidopsis," *Plant Physiol.* 122(3):645-655 (2000).

Lawrence and Roth, "Evolution of Coenzyme $B_{12}$ synthesis among enteric bacteria: evidence for loss and reacquisition of a multigene complex," *Genetics* 142(1):11-24 (1996).

Lawrence and Roth, "The cobalamin (Coenzyme $B_{12}$) biosynthetic genes of *Escherichia coli*," *J. Bacteriol.* 177(22):6371-6380 (1995).

Lebbink et al., "Engineering activity and stability of Thermotoga maritima glutamate dehydrogenase I. Introduction of a six-residue ion-pair network in the hinge region," *J. Mol. Biol.* 280:287-296 (1998).

Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee and Cho, "Identification of essential active-site residues in ornithine decarboxylase of Nicotiana glutinosa decarboxylating both L-ornithine and L-lysine," *Biochem. J.* 360:657-665 (2001).

Lee et al., "A new approach to directed gene evolution by recombined extension on truncated templates (RETT)," *J. Molec. Catalysis* 26:119-129 (2003).

Lee et al., "Batch and continuous cultivation of *Anaerobiospirillum succiniciproducens* for the production of succinic acid from whey," *Appl. Microbiol. Biotechnol.* 54(1):23-27 (2000).

Lee et al., "Biological conversion of wood hydrolysate to succinic acid by *Anaerobiospirillum succiniciproducens*," *Biotechnol. Lett.* 25(2):111-114 (2003).

Lee et al., "Biosynthesis of enantiopure (S)-3-hydroxybutyric acid in metabolically engineered *Escherichia coli*," *App. Microbiol. Biotechnol.* 79:633-641 (2008).

Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).

Lee et al., "Cloning and Characterization of Mannheimia succiniciproducens MBEL55E Phosphoenolpyruvate Carboxykinase (*pckA*) Gene," *Biotechnol. Bioprocess Eng.* 7:95-99 (2002).

Lee et al., "Fermentative production of chemicals that can be used for polymer synthesis," *Macromol. Biosci.* 4:157-164 (2004).

Lee et al., "Genome-based metabolic engineering of Mannheimia succiniciproducens for succinic acid productiion," *Appl. Environ. Microbiol.* 72(3):1939-1948 (2006).

Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).

Lee et al., "Phylogenetic diversity and the structural basis of substrate specificity in the β/α-barrel fold basic amino acid decarboxylases," *J. Biol. Chem.* 282:27115-27125 (2007).

Lee et al., "Metabolic engineering of *Escherichia coli* for enhanced production of succinic acid, based on genome comparison and in silico gene knockout simulation," *Appl Environ Microbiol.* 71(12):7880-7887 (2005).

Lehtio and Goldman, "The pyruvate format lyase family: sequences, structures and activation," *Protein Eng. Des.Sel.* 17:545-552 (2004).

Lehtio et al., "Crystal structure of glycyl radical enzyme from *Archaeoglobus fulgidus*," *J. Mol. Biol.* 357(1):221-235 (2006).

Lei et al., "A shared binding site for $NAD^+$ and Coenzyme A in an acetaldehyde dehydrogenase involved in bacterial degradation of aromatic compounds," *Biochemistry* 47:6870-6882 (2008).

Lemoine et al., "Microcorrespondence: Monofunctional biosynthetic peptidoglycan transglycosylases," *Mol. Microbiol.* 19(3):639-647 (1996).

Lemonnier and Lane, "Expression of the second lysine decarboxylase gene of *Escherichia coli*," *Microbiology* 144(Pt 3):751-760 (1998).

Lenski and Travisano, "Dynamics of adaptation and diversification: a 10,000-generation experiment with bacterial populations," *Proc. Natl. Acad. Sci. U.S.A.* 91(15):6808-6814 (1994).

Leonardo et al., "Anaerobic Regulation of the adh*E* gene, Encoding the Fermentative Alcohol Dehydrogenase of *Escherichia coli*," *J. Bacteriol.* 175(3):870-878 (1993).

Lepore et al., "The x-ray crystal structure of lysine-2,3-aminomutase from *Clostridium subterminale*," *Proc. Natl. Acad. Sci U.S.A.* 102:13819-13824 (2005).

Leppänen et al., "Pyruvate formate lyase is structurally homologous to type I ribonucleotide reductase," *Structure* 7:733-744 (1999).

Lessner et al., "An unconventional pathway for reduction of $CO_2$ to methane in CO-grown Methanosarcina acetivorans revealed by proteomics," *Proc. Natl. Acad. Sci. U.S.A.* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Levanon et al., "Effect of Oxygen on the *Escherichia coli* ArcA and FNR Regulation Systems and Metabolic Responses," *Biotechnol. Bioeng.* 89(5):556-564 (2005).

Li and Jordan, "Effects of substitution of tryptophan 412 in the substrate activation pathway of yeast pyruvate decarboxylase," *Biochemistry* 38:10004-10012 (1999).

Li et al., "Properties of Nicotinamide Adenine Dinucleotide Phosphate-Dependent Formate Dehydrogenase from *Clostridium thermoaceticum*," *J. Bacteriol.* 92(2):405-412 (1966).

Li et al., "Purification, crystallization and preliminary crystallographic studies on 2-dehydro-3-deoxygalactarate aldolase from Leptospira interrogans," *Acta. Crystallogr. Sect. F. Struct. Biol. Cryst. Commun.* 62(Pt 12):1269-1270 (2006).

Li, Guang-Shan, "Development of a reporter system for the study of gene expression for solvent production in *Clostridium beijerinckii* NRRL B592 and *Clostridium acetobutylicum* ATCC 824," Dissertation, Department of Biochemestry, Virginia Polytechnic Institute and State University (Sep. 1998).

Lian et al., "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).

Lin et al., "Functional Expression of Horseradish Peroxidase in *E. coli* by Directed Evolution," *Biotechnol. Prog.* 15:467-471 (1999).

Lin et al., "Effect of carbon sources differing in oxidation state and transport route on succinate production in metabolically engineered *Escherichia coli*," *J. Ind. Microbiol. Biotechnol.* 32:87-93 (2005).

Lin et al., "Fed-batch culture of a metabolically engineered *Escherichia coli* strain designed for high-level succinate production and yield under aerobic conditions," *Biotechnol. Bioeng.* 90:775-779 (2005).

Lin et al., "Genetic Reconstruction of the Aerobic Central Metabolism in *Escherichia coli* for the Absolute Aerobic Production of Succinate," *Biotechnol. Bioeng.* 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol. Prod.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, "Metabolic Network Design and Engineering in *Escherichia coli*" Ph.D. Thesis, Rice University, Dept. of Bioengineering (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl. Microbiol. Biotechnol.* 67(4): 515-523 (2005).

Lingen et al., "Alteration of the substrate specificity of benzoylformate decarboxylase from *Pseudomonas putida* by directed evolution," *Chembiochem.* 4:721-726 (2003).

Lingen et al., "Improving the carboligase activity of benzoylformate decarboxylase from *Pseudomonas putida* by a combination of directed evolution and site-directed mutagenesis," *Protein Eng.* 15:585-593 (2002).

Link et al., "Methods for generating precise deletions and insertions in the genome of wild-type *Eshcerichia coli*: application to open reading frame characterization," *J. Bacteriol.* 179:6228-6237 (1997).

Liou et al., "*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov," *Int. J. Syst. Evol. Microbiol.* 55(Pt 5):2085-2091 (2005).

Liu et al., "Kinetic and crystallographic analysis of active site mutants of *Escherichia coli* γ-aminobutyrate aminotransferase," *Biochemistry* 44:(8):2982-2992 (2005).

Liu et al., "Microbial production of R-3-hydroxybutyric acid by recombinant *E. coli* harboring genes of phbA, phbB , and tesB," *Appl. Microbiol. Biotechnol.* 76:811-818 (2007).

Liu et al., "Purification and characterization of ornithine acetyltransferase from *Saccharomyces cerevisiae*," *Eur. J. Biochem.* 228:291-296 (1995).

Liu et al., "Crystal structures of unbound and aminooxyacetate-bound *Escherichia coli* γ-aminobutyrate aminotransferase," *Biochemistry* 43(34):10896-10905 (2004).

Liu et al., "Economical succinic acid production from cane molasses by *Actinobacillus succinogenes*," *Bioresour Technol* 99(6):1736-1742 (2008).

Ljungdahl and Andreesen, "Formate dehydrogenase, a selenium-tungsten enzyme from *Clostridium thermoaceticum*," *Methods Enzymol.* 53:360-372 (1978).

Ljungdahl and Andreesen, "Tungsten, a component of active formate dehydrogenase from *Clostridium thermoacetium*," *FEBS Lett.* 54:279-282 (1975).

Ljungdahl, "The Autotrophic Pathway of Acetate Synthesis in Acetogenic Bacteria," *Ann. Rev. Microbiol.* 40:415-450 (1986).

Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle," *Angew Chem Int Ed.* 44(45):7442-7447 (2005).

Lokanath et al., "Crystal structure of novel NADP-dependent 3-hydroxyisobutyrate dehydrogenase from *Thermus thermophilus* HB8," *J. Mol. Biol.* 352(4):905-917 (2005).

Loke et al., "Active acetyl-CoA synthase from *Clostridium thermoaceticum* obtained by cloning and heterologous expression of acsAB in *Escherichia coli*," *Proc. Natl. Acad. Sci. U.S.A.* 97:12503-12535 (2000).

Longtine et al., "Additional modules for versatile and economical PCR-based gene deletion and modification in *Saccharomyces cerevisiae*," *Yeast* 14(10): 953-961 (1998).

Lopez-Barragan et al., "The *bzd* gene cluster, coding for anaerobic benzoate catabolism, in *Azoarcus* sp. Strain CIB," *J. Bacteriol.* 186(17):5762-5774 (2004).

Louie and Chan, "Cloning and characterization of the gamma-glutamyl phosphate reductase gene of *Campylobacter jejuni*," *Mol. Gen. Genet.* 240:29-35 (1993).

Louis et al., "Restricted distribution of the butyrate kinase pathway among butyrate-producing bacteria from the human colon," *J. Bacteriol.* 186:2099-2106 (2004).

Lovell et al., "Cloning and expression in *Escherichia coli* of the *Clostridium thermoaceticum* gene encoding thermostable formyltetrahydrofolate synthetase," *Arch. Microbiol.* 149(4):280-285 (1988).

Lovell et al., "Primary structure of the thermostable formyltetrahydrofolate synthetase from *Clostridium thermoaceticum*," *Biochemistry* 20(29):5687-5694 (1990).

Low et al., "Mimicking somatic hypermutation: Affinity maturation of antibodies displayed on baceriophage using a bacterial mutator strain," *J. Mol. Biol.* 260(3):359-368 (1996).

Lu et al., "Controlled Poetntial Enzymology of Methyl Transfer Reactions Involved in Acetyl-CoA Synthesis by CO Dehydrogenase and the Corrinoid/Iron-Sulfur Protein from *Clostridium thermoaceticum*," *J. Biol. Chem.* 265(6):3124-3133 (1990).

Lu et al., "Functional Analysis and Regulation of the Divergent spuABCDEFGH-spuI Operons for Polyamine Uptake and Utilization in *Pseudomonas aeruginosa* PAO1," *J. Bacteriol.* 184(14):3765-3773 (2002).

Lu et al., "Sequence and expression of the gene encoding the corrinoid/iron-sulfur protein from *Clostridium thermoaceticum* and reconstitution of the recombinant protein to full activity," *J. Biol. Chem.* 268(8):5605-5614 (1993).

Luersen, "Leishmania major thialsine $N^\epsilon$-acetyltransferase: Identification of amino acid residues crucial for substrate binding," *FEBS Lett.* 579:5347-5352 (2005).

Luli and Strohl, "Comparison of Growth, Acetate Production, and Acetate Inhibition of *Escherichia coli* Strains in Batch and Fed-Batch Fermentations," *Appl. Environ. Microbiol.* 56:1004-1011 (1990).

Lupa et al., "Distribution of genes encoding the microbial non-oxidative reversible hydroxyarylic acid decarboxylases/phenol carboxylases," *Genomics* 86:342-351 (2005).

Lupa et al., "Properties of the reversible nonoxidative vanillate/4-hydroxybenzoate decarboxylase from *Bacillus subtilis*," *Can. J. Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Lutz and Bujard, "Independent and tight regulation of transcriptional units in *Escherichia coli* via the LacR/O, the TetR/O and AraC/$I_1$-$I_2$ regulatory elements," *Nucleic Acids Res.* 25(6):1203-1210 (1997).

Lutz et al., "Creating multiple-crossover DNA libraries independent of sequence identity," *Proc. Natl. Acad. Sci U.S.A.* 98:11248-11253 (2001).

Lutz et al., "Dissecting the functional program of *Escherichia coli* promoters: the combined mode of action of Lac repressor and AraC activator," *Nucleic Acids Res.* 29(18):3873-3881 (2001).

Lutz et al., "Rapid generation of incremental truncation libraries for protein engineering using α-phosphothioate nucleotides," *Nucleic Acids Res.* 29:E16 (2001).

Lynch et al., "SCALEs: multiscale analysis of library enrichment," *Nat. Methods* 4(1):87-93 (2007).

Lynd et al., "Microbial Cellulose Utilization: Fundamentals and Biotechnology," *Microbiol. Mol. Biol. Rev.* 66:506-577 (2002).

Lynn et al., "Living Ring-Opening Metathesis Polymerization in Aqueous Media Catalyzed by Well-Defined Ruthenium Carbene Complexes," *J. Am. Chem. Soc.* 118(4):784-790 (1996).

Lynn et al., "Living Ring-Opening Metathesis Polymerization in Water," *J. Am. Chem. Soc.* 120(7):1627-1628 (1998).

Ma et al., "Induced rebuilding of aspartase conformation," *Ann. NY Acad. Sci.* 672:60-65 (1992).

Macis et al., "Properties and sequence of the Coenzyme $B_{12}$-dependent glycerol dehydratase of *Clostridium pasteurianum*," *FEMS Microbiol. Lett.* 164:21-28 (1998).

Mack and Buckel, "Conversion of glutaconate CoA-transferase from *Acidaminococcus fermentans* into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in *Acidaminococcus fermentans*," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The Methanosarcina barkeri genome: comparative analysis with *Methanosarcina acetivorans* and *Methanosarcina mazei* reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).

Mahadevan and Schilling, "The effects of alternate optimal solutions in constraint-based genome-scale metabolic models," *Metab. Eng.* 5(4):264-276 (2003).

Mahan and Csonka, "Genetic analysis of the proBA genes of *Salmonella typhimurium*: physical and genetic analyses of the cloned $proB^+A^+$ genes of *Escherichia coli* and of a mutant allele that confers proline overproduction and enhanced osmotolerance," *J. Bacteriol.* 156:1249-1262 (1983).

Mai and Adams, "Purification and characterization of two reversible and ADP-dependent acetyl Coenzyme A synthetases from the hyperthermophilic archaeon *Pyrococcus furiosus*," *J. Bacteriol.* 178:5897-5903 (1996.)

Maicas, S. et al., "NAD(P)H regeneration is the key for heterolactic fermentation of hexoses in Oenococcus oeni," *Microbiology* 148:325-332 (2002).

Maitra and Sprinson, "5-Dehydro-3-deoxy-D-arabino-heptulosonic acid 7-phosphate. An intermediate in the 3-dehydroquinate synthase reaction," *J Biol. Chem.* 253:5426-5430 (1978).

Majewski and Domach, "Simple Constrained-Optimization View of Acete Overflow in *E. coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from Pseudomonas sp strain CF600," *Acta. Crystallogr. D. Biol. Crystallogr.* 57(Pt 4):582-585 (2001).

Manning and Pollitt, "Tracer studies of the interconversion of R- and S-methylmalonic semialdehydes in man," *Biochem. J.* 231(2):481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170:991-994 (1988).

Marks et al., "Molecular cloning and characterization of (R)-3-hydroxybutyrate dehydrogenase from human heart," *J. Biol. Chem.* 267(22):15459-15463 (1992).

Martin et al., "Engineering a mevalonate pathway in *Escherichia coli* for production of terpenoids," *Nat. Biotechnol.* 21:796-802 (2003).

Martin et al., "Nematode.net update 2008: improvements enabling more efficient data mining and comparative nematode genomics," *Nucleic Acids Res.* 37:D571-D578 (2009).

Martinez-Blanco et al., "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe-4S] cluster and flavin," *Proc. Natl. Acad. Sci. U.S.A.* 101(44):15645-15649 (2004).

Mason and Dufour, "Alcohol acetyltransferases and the significance of ester synthesis in yeast," *Yeast* 16(14):1287-1298 (2000).

Matiasek et al., "Volatile ketone formation in bacteria: release of 3-oxopentanoate by soil pseudomonads during growth on heptanoate," *Curr. Microbiol.* 42:276-281 (2001).

Mat-Jan et al "Mutants of *Escherichia coli* Deficient in the Fermentative Lactate Dehydrogenase," *J. Bacteriol.* 171(1):342-348 (1989).

Matsumura et al., "Constitutive expression of catABC genes in the aniline-assimilating bacterium Rhodococcus species AN-22: production, purification, characterization and gene analysis of CatA, CatB and CatC," *Biochem. J.* 393:219-226 (2006).

Matsushima et al., "An enone reductase from Nicotiana tabacum: cDNA cloning, expression in *Escherichia coli*, and reduction of enones with the recombinant proteins," *Bioorg. Chem.* 36:23-28 (2008).

Matta et al., "Interactions of the antizyme AtoC with regulatory elements of the *Escherichia coli* atoDAEB operon," *J. Bacteriol.* 189(17):6324-6332 (2007).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus et al., "Insights into the Evolution of Allosteric Properties. The NADH Binding Site of Hexameric Type II Citrate Synthases," *Biochemistry* 42:5555-5565 (2003).

Mavrovouniotis, Estimation of standard Gibbs energy changes of biotransformations, *J. Biol. Chem.* 266:14440-14445 (1991).

Maynard et al., "Autocatalytic activation of acetyl-CoA synthase," *J. Biol. Inorg. Chem.* 9:316-322 (2004).

Mazur et al., "Cis,cis-muconate lactonizing enzyme from *Trichosporon cutaneum*: evidence for a novel class of cycloisomerases in eucaryotes," *Biochemistry* 33:1961-1970 (1994).

McAlister-Henn and Thompson, "Isolation and expression of the gene encoding yeast mitochondrial malate dehydrogenase," *J. Bacteriol.* 169:5157-5166 (1987).

McCarthy et al., "Crystal structure of methylmalonyl-Coenzyme A epimerase from *P. shermanii*: a novel enzymatic function on an ancient metal binding scaffold," *Structure* 9(7):637-646 (2001).

McCullough et al., "Enzymatic decarboxylation of the aminobenzoates," *J. Am. Chem. Soc.* 79:628-630 (1957).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McInerney et al., "The genome of *Syntrophus aciditrophicus*: Life at the thermodynamic limit of microbial growth," *Proc. Natl. Acad. Sci U.S.A.* 104:7600-7605 (2007).

McKinlay et al., "Prospects for a bio-based succinate industry," *Appl. Microbiol. Biotechnol.* 76(4):727-740 (2007).

McPherson and Wootton, "Complete nucleotide sequence of the *Escherichia coli* gdhA gene," *Nucleic Acids Res.* 11:5257-5266 (1983).

McPherson et al., "Multiple interactions of lysine-128 of *Escherichia coli* glutamate dehydrogenase revealed by site-directed mutagenesis studies," *Protein Eng.* 2(2):147-152 (1988).

Meagher, "Purification and partial amino acid sequence of the cyanogen bromide fragments of muconolactone isomerase from *Pseudomonas putida*," *Biochim. Biophys. Acta* 494:33-47 (1977).

Mechichi et al., "Alicycliphilus denitrificans gen. nov., sp. nov., a cyclohexanol-degrading, nitrate-reducing β-proteobacterium," *Int. J. Syst. Evol. Microbiol.* 53:147-152 (2003).

Megraw et al., "Formation of lactyl-Coenzyme A and pyruvyl-Coenzyme A from lactic acid by *Escherichia coli*," *J. Bacteriol.* 90(4):984-988 (1965).

Meinnel et al., "Structural and Biochemical Characterization of the *Escherichia coli* argE Gene Product," *J. Bacteriol.* 174(7):2323-2331 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

Meng and Li, "Cloning, expression and characterization of a thiolase gene from *Clostridium pasteurianum*," *Biotechnol. Lett.* 28(16):1227-1232 (2006).

Menon and Ragsdale, "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzymes and fluxes of pyruvate metabolism," *Botechnol. Bioeng.* 60(5):617-626 (1998).

Merkel and Nichols, "Characterization and sequence of the *Escherichia coli* panBCD gene cluster," *FEMS Microbiol. Lett.* 143(2-3):247-252 (1996).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Metz et al., "Purification of a jojoba embryo fatty acyl-Coenzyme A reductase and expression of its cDNA in high erucic acid rapeseed," *Plant Phys.* 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Miller et al., "Structure of β-lactam synthetase reveals how to synthesize antibiotics instead of asparagine," *Nat. Struct. Biol.* 8(8):684-689 (2001).

Miller et al., "The catalytic cycle of β-lactam synthetase observed by x-ray crystallographic snapshots," *Proc. Natl. Acad. Sci. U.S.A.* 99(23):14752-14757 (2002).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono and Nagasaki, "Occurrence of L-Lysine ε-Dehydrogenase in *Agrobacterium tumefaciens*," *J. Bacteriol.* 150(1):398-401 (1982).

Misono et al., "Properties of L-lysine epsilon-dehydrogenase from *Agrobacterium tumefaciens*," *J. Biochem.* 105(6):1002-1008 (1989).

Miura et al., "Molecular Cloning of the nemA Gene Encoding N-Ethylmaleimide Reductase from *Escherichia coli*," *Biol. Pharm. Bull.* 20(1):110-112 (1997).

Miyazaki et al., "α-Aminoadipate aminotransferase from an extremely thermophilic bacterium, *Thermus thermophilus*," *Microbiology* 150:2327-2334 (2004).

Mizobata et al., "Purification and characterization of a thermostable class II fumarase from *Thermus thermophilus*," *Arch. Biochem. Biophys.* 355(1):49-55 (1998).

Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Momany et al., "Crystallization of diaminopimelate decarboxylase from *Escherichia coli*, a stereo specific D-amino-acid decarboxylase," *Acta. Crystallogr. D. Biol. Crystallogr.* 58(Pt 3):549-552 (2002).

Momany et al., "Crystallographic Structure of PLP-Dependent Ornithine Decarboxylase from Lactobacillus 30a to 3.0 Å Resolution," *J. Mol. Biol.* 252:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moon et al., "Metabolic engineering of *Escherichia coli* for the production of malic acid," *Biochem. Eng. J.* 40(2):312-320 (2008).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris and Jinks-Robertson, "Nucleotide sequence of the LYS2 gene of *Saccharomyces cerevisiae*: homology to Bacillus brevis tyrocidine synthetase 1," *Gene* 98:141-145 (1991).

Morsomme et al., "Single point mutations in various domains of a plant plasma membrane $H^+$-ATPase expressed in *Saccharomyces cerevisiae* increase $H^+$-pumping and permit yeast growth at low pH," *Embo. J.* 15(20):5513-5526 (1996).

Morton et al., "Cloning, sequencing, and expressions of genes encoding enzymes of the autotrophic acetyl-CoA pathway in the acetogen *Clostridium thermoaceticum*," In M. Sebald (ed.), *Genetics and molecular biology of anaerobic bacteria*, Springer Verlag, New York, 389-406 (1992).

Morton et al., "The primary structure of the subunits of carbon monoxide dehydrogenase/acetyl-CoA synthase from *Clostridium thermoaceticum*," *J. Biol. Chem.* 266(35):23824-23828 (1991).

Moskowitz et al., "Metabolism of poly-β-hydroxybutyrate. II. Enzymatic synthesis of D-(-)-β-hydroxybutyryl Coenzyme A by an enoyl hydrase from rhodospirillum rubrum," *Biochemistry* 8:2748-2755 (1969).

Moszer, "The complete genome of *Bacillus subtilis*: from sequence annotation to data management and analysis," *FEBS Lett.* 430:28-36 (1998).

Mouttaki et al., "Cyclohexane Carboxylate and Benzoate Formation from Crotonate in *Syntrophus aciditrophicus*," *Appl. Environl. Microbiol.* 73(3):930-938 (2007).

Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Müh et al., "Mössbauer study of 4-hydroxybutyryl-CoA dehydratase probing the role of an iron-sulfur cluster in an overall non-redox reaction," *Eur. J. Biochem.* 248:380-384 (1997).

Mukhopadhyay and Purwantini, "Pyruvate carboxylase from *Mycobacterium smegmatis*: stabilization, rapid purification, moleculare and biochemical characterization and regulation of the cellular level," *Biochim. Biophys. Acta.* 1475(3):191-206 (2000).

Muller and Buckel, "Activation of (R)-2-hydroxyglutaryl-CoA dehydratase from *Acidaminococcus fermentans*," *Eur. J. Biochem.* 230(2):698-704 (1995).

Muller et al., "Nucleotide exchange and excisiion technology (NExT) DNA shuffling; a robust method for DNA fragmentation and directed evolution," *Nucleic Acids Res.* 33:e117 (2005).

Müller, "Energy Conservation in Acetogenic Bacteria," *Appl. Environ. Microbiol.* 69:6345-6353 (2003).

Murakami et al., "Purification and characterization of two muconate cycloisomerase isozymes from aniline-assimilating Frateuria species ANA-18," *Biosci. Biotechnol. Biochem.* 62:1129-1133 (1998).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Nagasawa et al., "Cloning and Nucleotide Sequence of the Alcohol Acetyltransferase II gene (*ATF2*) from *Saccharomyces cerevisiae* Kyokai No. 7," *Biosci. Biotechnol. Biochem.* 62:1852-1857 (1998).

Nagata et al., "Gene cloning, purification, and characterization of thermostable and halophilic leucine dehydrogenase from a halophilic thermophile, *Bacillus licheniformis* TSN9," *Appl. Microbiol. Biotechnol.* 44:432-438 (1995).

Naggert et al., "Cloning, sequencing, and characterization of *Escherichia coli* thioesterase II," *J. Biol. Chem.* 266(17):11044-11050 (1991).

Nahvi et al., "Genetic Control by a Metabolite Binding mRNA," *Chem. Biol.* 9:1043-1049 (2002).

Naidu and Ragsdale, "Characterization of a three-component vanillate O-demethylase from *Moorella thermoacetica*," *J. Bacteriol.* 183(11):3276-3281 (2001).

Najafpour and Younesi, "Ethanol and acetate synthesis from waste gas using batch culture of *Clostridium ljungdahlii*," *Enzyme Microb. Technol.* 38:223-228 (2006).

Najmudin et al., "Purification, crystallization and preliminary X-ray crystallographic studies on acetolactate decarboxylase," *Acta. Crystallogr. D. Biol. Crystallogr.* 59(Pt. 6):1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

Nakazawa et al., "Studies on monooxygenases. V. Manifestation of amino acid oxidase activity by L-lysine monooxygenase," *J. Biol. Chem.* 247:3439-3444 (1972).

Namba et al., "Coenzyme A- and Nicotinamide Adenine Dinucleotide-dependent Branched Chain α-Keto Acid Dehydrogenase," *J. Biol. Chem.* 244(16):4437-4447 (1969).

Neidhart et al., "Mandelate racemase and muconate lactonizing enzyme are mechanistically distinct and structurally homologous," *Nature* 347:692-694 (1990).

Ness et al., "Synthetic shuffling expands functional protein diversity by allowing amino acids to recombine independently," *Nat. Biotechnol.* 20:1251-1255 (2002).

Nicolaou et al., "The Diels-Alder Reaction in Total Synthesis," *Angew Chemie Int Ed.* 41:1668-1698 (2002).

Niegemann et al., "Molecular organization of the *Escherichia coli* gab cluster: nucleotide sequence of the structural genes gabD and gabP and expression of the GABA permease gene," *Arch.Microbiol* 160:454-460 (1993).

Nimmo, "Kinetic mechanism of *Escherichia coli* isocitrate dehydrogenase and its inhibition by glyoxylate and oxaloacetate," *Biochem. J.* 234(2):317-323 (1986).

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).

Nishizawa et al., "Gene expression and characterization of two 2-oxoacid:ferredoxin oxidoreductases from Aeropyrum pernix K1," *FEBS Lett.* 579:2319-2322 (2005).

Nissen et al., "Expression of a cytoplasmic transhydrogenase in *Saccharomyces cerevisiae* results in formation of 2-oxoglutarate due to depletion of the NADPH pool," *Yeast* 18:19-32 (2001).

Nogales et al., "Characterization of the last step of the aerobic phenylacetic acid degradation pathway," *Microbiology* 153(Pt 2):357-365 (2007).

Noichinda et al., "Subcellular Localization of Alcohol Acetyltransferase in Strawberry Fruit," *Food Sci. Technol. Res.* 5(3):239-242 (1999).

Nölling et al., "Genome sequence and comparative analysis of the solvent-producing bacterium *Clostridium acetobutylicum*," *J. Bacteriol.* 183(16):4823-4838 (2001).

Norton, "The Diels-Alder Diene Synthesis," *Chem. Rev.* 31:319-523 (1942).

Nowicki et al., "Recombinant tyrosine aminotransferase from *Trypanosoma cruzi*: structural characterization and site directed mutagenesis of a broad substrate specificity enzyme," *Biochim. Biophysica Acta* 1546:268-281 (2001).

O'Brien and Gennis, "Studies of the Thiamin Pyrophosphate Binding Site of *Escherichia coli* Pyruvate Oxidase," *J. Biol. Chem.* 255(8):3302-3307 (1980).

O'Brien et al, "Regulation by Lipids of Cofactor Binding to a Peripheral Membrane Enzyme: Binding of Thiamin Pyrophosphate to Pyruvate Oxidase," *Biochemistry* 16(14):3105-3109 (1977).

O'Brien et al., "Chemical, physical and enzymatic comparisons of formyltetrahydrofolate synthetases from thermo- and mesophilic clostridia," *Experientia. Suppl.* 26:249-262 (1976).

O'Brien et al., "Insight into the Mechanism of the $B_{12}$-Independent Glycerol Dehydratase from *Clostridium butyricum*: Preliminary Biochemical and Structural Characterization," *Biochemistry* 43:4635-4645 (2004).

Ofman et al., "2-Methyl-3-hydroxybutyryl-CoA dehydrogenase deficiency is caused by mutations in the HADH2 gene," *Am. J. Hum. Genet.* 72:1300-1307 (2003).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by Pseudomonas. Purification and Properties of a Deacetylase-Thiolstrerase Utilizing 4-Acetamidobutyryl CoA and Related Compounds," *J. Biol. Chem.* 256(14):7642-7651 (1981).

Okino et al., "An effieicient succinic acid production process in a metabolically engineered *Corynebacterium glutamicum* strain," *Appl. Microbiol. Biotechnol.* 81(3):459-464 (2008).

Oku and Kaneda, "Biosynthesis of branched-chain fatty acids in *Bacillus subtilis*. A decarboxylase is essential for branched-chain fatty acid synthetase," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism," *Enzyme Protein* 47:136-148 (1993).

Olivera et al., "Molecular characterization of the phenylacetic acid catabolic pathway in *Pseudomonas putida* U: the phenylacetyl-CoA catabolon," *Proc. Natl. Acad. Sci. U.S.A.* 95(11):6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from *Bacillus subtilis*," *Microbiology* 140:1023-1025 (1994).

Orencio-Trejo et al., "Metabolic regluation analysis of an ethanologenic *Escherichia coli* strain based on RT-PCR and enzymatic activities," *Biotechnol. Biofuels* 1:8 (2008).

Ostermeier et al., "A Combinatorial approach to hybrid enzymes independent of DNA homology," *Nat. Biotechnol.* 17:1205-1209 (1999).

Ostermeier et al., "Combinatorial protein engineering by incremental truncation," *Proc. Natl. Acad. Sci. U.S.A.* 96:3562-3567 (1999).

O'Sullivan et al., "Purification and characterisation of acetolactate decarboxylase from *Leuconostoc lactis* NCW1," *FEMS Microbiol. Lett* 194(2):245-249 (2001).

Otten and Quax, "Directed evolution:selecting today's biocatalysts," *Biomol. Eng.* 22:1-9 (2005).

Overkamp et al., "Functional analysis of structural genes for $NAD^+$-dependent formate dehydrogenase in *Saccharomyces cerevisiae*," *Yeast* 19:509-520 (2002).

Overkamp et al., "In vivo analysis of the mechanism for oxidation of cytosolic NADH by *Saccharomyces cerevisiae* mitochondria," *J. Bacteriol.* 182:2823-2830 (2000).

Padovani and Banerjee, "Assembly and protection of the radical enzyme, methylmalonyl-CoA mutase, by its chaperone," *Biochem.* 45(30):9300-9306 (2006).

Paik and Kim, "Enzymic syntehsis of ε-N-Acetyl-L-Lysine," *Arch. Biochem. Biophys.* 108:221-229 (1964).

Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).

Parales and Harwood, "Characterization of the Genes Encoding β-Ketoadipate: Succinyl-Coenzyme A Transferase in *Pseudomonas putida*," *J. Bacteriol.* 174(14):4657-4666 (1992).

Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).

Park et al., "Metabolic engineering of *Escherichia coli* for the production of L-valine based on transcriptome analysis and in silico gene knockout simulation," *Proc. Natl. Acad. Sci. U.S.A.* 104(19):7797-7802 (2007).

Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).

Park et al., "Utilization of Electrically Reduced Neutral Red by *Actinobacillus succinogenes*: Physiological Function of Neutral Red in Membrane-Driven Fumarate Reduction and Energy Conservation," *J. Bacteriol* 181(8):2403-2410 (1999).

Parkin et al., "Rapid and efficient electrocatalytic $CO_2$/CO interconversions by Carboxydothermus hydrogenoformans CO dehydrogenase I on an electrode," *J. Am. Chem. Soc.* 129(34):10328-10329 (2007).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).

Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).

Patel et al., "β-ketoadipate enol-lactone hydrolases I and II from *Acinetobacter calcoaceticus*," *J. Biol. Chem.* 250:6567-6577 (1975).

Patil et al., "Use of genome-scale microbial models for metabolic engineering," *Curr. Opin. Biotechnol.* 15(1):64-69 (2004).

Patnaik et al., "Genome shuffling of *Lactobacillus* for improved acid tolerance," *Nat. Biotechnol.* 20:707-712 (2002).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier and Harwood, "2-Ketocyclohexanecarboxyl Coenzyme A Hydrolase, the Ring cleavage Enzyme Required for Anaerobic Benzoate Degradation of *Rhodopseudomonas palustris*," *J. Bacteriol.* 180(9):2330-2336 (1998).

Peoples and Sinskey, "Fine structural analysis of the *Zoogloea ramigera* phbA-phbB locus encoding β-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino acid sequence of alcohol dehydrogenase from the thermophilic bacterium *Thermoanaerobium brockii*," *Biochemistry* 28(16):6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe.* 3:259-270 (1997).

Perez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior et al., "Reactivity of lactones and GHB formation," *J. Org. Chem.* 70:420-426 (2005).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta* 421(2):334-347 (1976).

Pfanner and Geissler, "Versatility of the mitochondrial protein import machinery," *Nat. Rev. Mol. Cell. Biol.* 2(5):339-349 (2001).

Pfluger et al., "Lysine-2,3-Aminomutase and β-Lysine Acetyltransferase Genes of Methanogenic Archaea Are Salt Induced and Are Essential for the Biosynthesis of $N^ε$-Acetyl-β-Lysine and Growth at High Salinity," *Appl. Environ. Microbiol.* 69(10):6047-6055 (2003).

Phalip et al., "Purification and properties of the α-acetolactate decarboxylase from *Lactococcus lactis* subsp. Lactis NCDO 2118," *FEBS Lett.* 351(1):95-99 (1994).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400, 402, 404, 406, 408 (2000).

Pierce et al., "The Complete Genome Sequence of *Moorella thermoacetia* (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in *Bacillus sphericus*," *Biochem. J.* 287:685-690 (1992).

Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).

Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Pollard et al., "Purification, characterisation and reaction mechanisms of monofunctional 2-hydroxypentadienoic acid hydratase from *Escherichia coli*," *Eur. J. Biochem. FEBS* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from Pseudomonas sp. strain CF600," *J. Bacteriol.* 175(2):377-385 (1993).

Price et al"Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Pronk et al., "Pyruvate metabolism in *Saccharomyces cerevisiae*," *Yeast* 12:1607-1633 (1996).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant NAD(H)-dependent glutamate dehydrogenase activity in transgenic tobacco via alteration of β subunit levels," *Planta* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Qiu et al., "Metabolic engineering of Aeromonas hydrophila for the enhanced production of poly(3-hydroxybutyrate-co-3-hydroxyhexanoate)," *Appl. Microbiol. Biotechnol.* 69(5):537-542 (2006).

Qu et al., "Inhibition of human ornthine decarboxylase activity by enantiomers of difluoromethylornithine," *Biochem. J.* 375:465-470 (2003).

Quail and Guest, "Purification, characterization and mode of action of pdhR, the transcriptional repressor of the PdhR-aceEF-Ipd operon of *Escherichia coli*," *Mol. Microbiol.* 15(3):519-529 (1995).

Rado and Hoch, "Phosphotransacetylase from *Bacillus subtilis*: purification and physiological studies," *Biochim. Biophys. Acta* 321:114-125 (1973).

Ragsdale et al., "Acetogenesis and the Wood-Ljungdahl pathway of $CO_2$ fixation," *Biochimica. Biophysica. Acta* 1784(12):1873-1898 (2008).

Ragsdale, "Enzymology of the wood-Ljungdahl pathway of acetogenesis," *Ann. NY Acad Sci.* 1125:129-136 (2008).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Rajpal et al., "A general method for greatly improving the affinity of antibodies by using combinatorial libraries," *Proc. Natl. Acad. Sci. U.S.A.* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J Biochem.* 149:401-404 (1985).

Rangarajan et al., "Structure of [NiFe] hydrogenase maturation protein HypE from *Escherichia coli* and its interaction with HypF," *J. Bacteriol.* 190(4):1447-1458 (2008).

Rasmussen, L.J., et al. "Carbon Metabolism Regulates Expression of the *pfl* (Pyruvate-Formate-Lyase) Gene in *Escherichia coli*," *J. Bacteriol.* 173(20):6390-6397 (1991).

Rathinasabapathi, "Propionate, a source of β-alanine, is an inhibitor of β-alanine methylation in Limonium latifoilium Plunbaginaces," *J. Plant Physiol.* 159:671-674 (2002).

Ratnatilleke et al., "Cloning and sequencing of the Coenzyme $B_{12}$-binding domain of isobutyryl-CoA mutase from *Streptomyces cinnamonensis*, reconstitution of mutase activity, and characterization of the recombinant enzyme produced in *Escherichia coli*," *J. Biol. Chem.* 274(44):31679-31685 (1999).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin $B_{12}$) biosynthetic genes: functional studies in *S. typhimurium* and *Escherichia coli*," *J. Bacteriol.* 178(3):753-767 (1996).

Ravagnani et al., "Spo0A directly controls the switch from acid to solvent production in solvent-forming clostridia," *Mol. Microbiol.* 37(5):1172-1185 (2000).

Raybuck et al., "Kinetic characterization of the carbon monoxide-acetyl-CoA (carbonyl group) exchange activity of the acetyl-CoA synthesizing CO dehydrogenase from *Clostridium thermoaceticum*," *Biochemistry* 27(20):7698-7702 (1988).

Raynaud et al., "Molecular characterization of the 1,3-propanediol (1,3-PD) operon of *Clostridium butyricum*," *Proc. Natl. Acad. Sci. U.S.A.* 100:5010-5015 (2003).

Rea et al., "Structure and Mechanism of HpcH: A Metal Ion Dependent Class II Aldolase from the Homoprotocatechuate Degradation Pathway of *Escherichia coli*," *J. Mol. Biol.* 373:866-876 (2007).

Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).

Reda et al., "Reversible interconversion of carbon dioxide and formate by an electroactive enzyme," *Proc. Natl. Acad. Sci. U.S.A.* 105:10654-10658 (2008).

Reetz and Carballeira, "Iterative saturation mutagenesis (ISM) for rapid directed evolution of functional enzymes," *Nat. Protoc.* 2:891-903 (2007).

Reetz et al., "Creation of Enantioselective Biocatalysts for Organic Chemistry by in Vitro Evolution," *Angew. Chem. Int. Ed. Engl.* 36:2830-2832 (1997).

Reetz et al., "Directed Evolution of an Enantioselective Enzyme through Combinatorial Multiple-Cassette Mutagenesis, " *Angew. Chem. Int. Ed. Engl.* 40:3589-3591 (2001).

Reetz et al., "Expanding the Range of Substrate Acceptance Enzymes: Cominatorial Active-Site Saturation Test," *Angew. Chem. Int. Ed.* 117:4264-4268 (2005).

Reetz et al., "Iterative saturation mutagenesis on the basis of B factors as a strategy for incresing protein thermostability," *Angew. Chem. Int. Ed.* 45:7745-7751 (2006).

Regev-Rudzki et al., "Yeast Aconitase in Two Locations and Two Metabolic Pathways: Seeing Small Amounts Is Believing," *Mol. Biol. Cell* 16:4163-4171 (2005).

Reidhaar-Olson and Sauer, "Combinatorial cassette mutagenesis as a probe of the informational content of protein sequences," *Science* 241:53-57 (1988).

Reidhaar-Olson et al., "Random mutagenesis of protein sequences using oligonucleotide cassettes," *Methods Enzymmol.* 208:564-586 (1991).

Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).

Reitzer et al., "Crystallization and preliminary X-ray analysis of recombinant glutamate mutase and of the isolated component S from *Clostridium cochlearium*," *Acta. Crystallogr. D. Biol. Crystallogr.* 54(Pt 5):1039-1042 (1998).

Repetto and Tzagoloff, "Structure and Regulation of KGD1, the Structural Gene for Yeast α-Ketoglutarate Dehydrogenase," *Mol. Cell. Biol.* 9(6):2695-2705 (1989).

Reshetnikov, et al., "Characterization of the ectoine biosynthesis genes of haloalkalotolerant obligate methanotroph 'Methylomicrobium alcaliphilum 20Z'," *Arch. Microbiol.* 184:286-297 (2006).

Resnekov et al., "Organization and regulation of the *Bacillus subtilis* odhAB operon, which encodes two of the subenzymes of the 2-oxoglutarate dehydrogenase complex," *Mol. Gen. Genet.* 234:285-296 (1992).

Rhodes et al., "Production of fumaric acid by *Rhizopus arrhuzus*," *Appl. Microbiol.* 7:74-80 (1959).

Rhodes et al., "Production of Fumaric Acid in 20-Liter Fermentors," *Appl. Microbiol.* 10(1):9-15 (1962).

Rigden et al., "A cofactor-dependent phosphoglycerate mutase homolog from *Bacillus stearothermophilus* is actually a broad specificity phosphatase," *Protein Sci.* 10:1835-1846 (2001).

Ringer et al., "Monoterpene double-bond reductases of the (−)-menthol biosynthetic pathway: isolation and characterization of cDNAs encoding (−)-isopiperitenone reductase and (+)-pulegone reductase of peppermint," *Arch. Biochem. Biophys.* 418(1):80-92 (2003).

Ringquist et al., "Translation initiation in *Escherichia coli*: sequences within the ribosome-binding site," *Mol. Microbiol.* 6(9):1219-1229 (1992).

Riondet et al., "Measurement of the intracellular pH in *Escherichia coli* with the internally conjugated fluorescent probe 5- (and 6-)carboxyfluorescein succinimidyl ester." *Biotechnol. Tech.* 11:735-738 (1997).

Rioux et al., "Two outer membrane transport systems for vitamin $B_{12}$ in *Salmonella typhimurium*," *J. Bacteriol.* 171:2986-2993 (1989).

Rioux et al., "Vitamin $B_{12}$ transport in *Escherichia coli* K12 does not require the btuE gene of the btuCED operon," *Mol. Gen. Genet.* 217:301-308 (1989).

Riviere et al., "Acetyl:succinate CoA-transferase in procyclic *Trypanosoma brucei*. Gene identification and role in carbohydrate metabolism." *J. Biol. Chem.* 279:45337-45346 (2004).

Roa Engel et al., "Fumaric acid production by fermentation," *Appl. Microbiol. Biotechnol.* 78(3):379-389 (2008).

Roberts et al, "The Role of Enoyl-CoA Hydratase in the Metabolism of Isoleucine by *Pseudomonas putida*," *Arch. Microbiol.* 117:99-108 (1978).

Roberts et al., "Acetyl-Coenzyme A synthesis from methyltetrahydrofolate, CO, and Coenzyme A by enzymes purified from *Clostridium thermoaceticum*: attainment of in vivo rates and identification of rate-limiting steps," *J. Bacteriol.* 174(14):4667-4676 (1992).

Roberts et al., "Cloning and expression of the gene cluster encoding key proteins involved in acetyl-CoA synthesis in *Clostridium thermoaceticum*: CO dehydrogenase, the corrinoid/Fe-S protein, and methyltransferase," *Proc. Natl. Acad. Sci. U.S.A.* 86(1):32-36 (1989).

Robinson et al., "Studies on Rat Brain Acyl-Coenzyme A Hydrolase (Short Chain)," *Biochem. Biophys. Res. Commun.* 71(4):959-965 (1976).

Roca et al., "Metabolic engineering of ammonium assimilation in xylose-fermenting *Saccharomyces cerevisiae* improves ethanol production," *Appl. Environ. Microbiol.* 69:4732-4736 (2003).

Rodriguez et al., "Characterization of the p-Coumaric Acid Decarboxylase from *Lactobacillus plantarium* CECT $748^T$," *J. Agric. Food Chem.* 56:3068-3072 (2008).

Roffia et al., "Byproduct Identification in the Terepthalic Acid Production Process and Possible Mechanisms of their Formation," *Ind. Eng. Chem. Prod. Res. Dev.* 23:629-634 (1984).

Rohdich et al., "Enoate reductases of Clostridia. Cloning, sequencing, and expression," *J. Biol. Chem.* 276(8):5779-5787 (2001).

Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).

Romero et al., "Partial purification and characterization and nitrogen regulation of the lysine ε-aminotransferase of *Streptomyces clavuligers*," *J. Ind. Microbiol. Biotechnol.* 18:241-246 (1997).

Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).

Rose and Weaver, "The role of the allosteric B site in the fumarase reaction," *Proc. Natl. Acad. Sci. U.S.A.* 101(10):3393-3397 (2004).

Rose et al., "Enzymatic phosphorylation of acetate," *J. Biol. Chem.* 211(2):737-756 (1954).

Rosenberg, "A Comparison of Lipid Patterns in Photosynthesizing and Nonphotosynthesizing Cells of *Euglena gracilis*," *Biochem.* 2:1148-1154 (1963).

Roszak et al., "The Structure and Mechanism of the Type II Dehydroquinase from *Streptomyces coelicolor*," *Structure* 10:493-503 (2002).

Roth et al., "Characterization of the cobalamin (vitamin $B_{12}$) biosynthetic genes of *Salmonella typhimurium*," *J. Bacteriol.* 175:3303-3316 (1993).

Rother and Metcalf, "Anaerobic growth of *Methanosarcina acetivorans* C2A on carbon monoxide: an unusual way of life for a methanogenic archaeon," *Proc. Natl. Acad. Sci. U.S.A.* 101(48):16929-16934 (2004).

Rother et al., "Genetic and proteomic analyses of CO utilization by *Methanosarcina acetivorans*," *Arch. Microbiol.* 188(5):463-472 (2007).

Rous, "On the occurrence of enzymes of ketone-body metabolism in human adipose tissue," *Biochem. Biophys. Res. Commun.* 69(1):74-78 (1976).

Roux and Walsh, "p-aminobenzoate synthesis in *Escherichia coli*: kinetic and mechanistic characterization of the amidotransferase PabA," *Biochemistry* 31:6904-6910 (1992).

Roux and Walsh, "p-Aminobenzoate synthesis in *Escherichia coli*: mutational analysis of three conserved amino acid residues of the amidotransferase PabA," *Biochemistry* 32:3763-3768 (1993).

Roy and Dawes, "Cloning and Characterization of the gene Encoding Lipoamide Dehydrogenase in *Saccharomyces cerevisiae*," *J. Gen. Microbiol.* 133:925-933 (1987).

Roymoulik et al., "Rearrangement of L-2-hydroxyglutarate to L-threo-3-methylmalate catalyzed by adenosylcobalamin-dependent glutamate mutase," *Biochem.* 39(33):10340-10346 (2000).

Rozell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).

Rudman and Meister, "Transamination in *Escherichia coli*," *J. Biol. Chem.* 200(2):591-604 (1953).

Ruldeekulthamrong et al., "Molecular characterization of lysine 6-dehydrogenase from *Achromobacter denitrificans*," *BMB Reports* 790-795 (2008).

Sabo et al., "Purification and physical properties of inducible *Escherichia coli* lysine decarboxylase," *Biochemistry* 13:622-670 (1974).

Sadowski, "The Flp recombinase of the 2-μm plasmid of *Saccharomyces cerevisiae*," *Prog. Nucleic Acid Res. Mol. Biol.* 51:53-91 (1995).

Saegesser et al., "Stability of broad host range cloning vectors in the phototrophic bacterium *Rhodospirillum rubrum*," *FEMS Microbiol. Lett.* 95:7-11 (1992).

Saito and Doi, "Microbial synthesis and properties of poly(3-hydroxybutyrate-co-4-hydroxybutyrate) in *Comamonas acidovorans*," *Int. J Biol Macromol.* 16:99-104 (1994).

Sakai et al, "Acetate and Ethanol Production from $H_2$ and $CO_2$ by Morrella sp. Using a Repeated Batch Culture," *J. Biosci. Bioeng.* 99:252-258 (2005).

Sakanyan et al., "A re-examination of the pathway for ornithine biosynthesis in a thermophilic and two mesophilic Bacillus species," *J. Gen. Microbiol.* 138:125-130 (1992).

Sakurada et al., "Acetylpolyamine Amidohydrolase from *Mycoplana ramosa*: Gene Cloning and Characterization of the Metal-Substituted Enzyme," *J. Bacteriol.* 178(19):5781-5786 (1996).

Salmon et al., "Global gene expression profiling in *Escherichia coli* K12. Effects of oxygen availability and ArcA," *J. Biol. Chem.* 280(15):15084-15096 (2005).

Saltzgaber-Muller et al., "Nuclear genes coding the yeast mitochondrial adenosine triphosphatase complex. Isolation of ATP2 coding the $F_1$-ATPase $\beta$ subunit," *J. Bio. Chem.* 258(19):11465-11470 (1983).

Samanta and Harwood, "Use of *Rhodopseudomonas palustris* genome sequence to identify a single amino acid that contributes to the activity of Coenzyme A ligase with chlorinated substrates," *Mol. Microbiol.* 55(4):1151-1159 (2005).

Samsonova et al., "Molecular cloning and characterization of *Escherichia coli* K12 ygjG gene," *BMC Microbiol.* 3:2 (2003).

Samuelov et al., "Whey fermentation by *Anaerobiospirillum succiniciproducens* for production of a succinate-based animal feed additive," *Appl. Environ. Microbiol.* 65(5):2260-2263 (1999).

San et al., "Metabolic Engineering through Cofactor Manipulation and its Effects on Metabolic Flux Redistribution in *Escherichia coli*," *Metab Eng.* 4(2):182-192 (2002).

Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).

Sanchez et al., "Novel pathway engineering design of the anaerobic central metabolic pathway in *Escherichia coli* to increase succinate yield and productivity," *Metab. Eng.* 7(3):229-239 (2005).

Sanchez et al., "Batch culture characterization and metabolic flux analysis of succinate-producing *Escherichia coli* strains," *Metab Eng.* 8(3):209-226 (2006).

Sanchez et al., "Effect of different levels of NADH availability on metabolic fluxes of *Escherichia coli* chemostat cultures in defined medium," *J. Biotechnol.* 117(4):395-405 (2005).

Sankaranarayanan et al., "Preliminary x-ray crystallographic analysis of ornithine acetyltransferase (Rv1653) from *Mycobacterium tuberculosis*," *Acta. Crystallogr. Sect. F. Struct. Biol. Cryst. Commun.* 65(Pt 2):173-176 (2009).

Sanyal et al., "Biosynthehsis of pimeloyl-CoA, a biotin precursor in *Escherichia coli*, follows a modified fatty acid synthesis pathway: $^{13}$C-labeling studies," *J. Am. Chem. Soc.* 116:2637-2638 (1994).

Sariaslani, "Development of a Combined biological and Chemical Process for Production of Industrial aromatics from Renewable Resources," *Annu. Rev. Microbiol.* 61:51-69 (2007).

Sass et al., "Folding of fumarase during mitochondrial import determines its dual targeting in yeast," *J. Biol. Chem.* 278(46):45109-45116 (2003).

Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).

Sauer and Thauer, "Methanol:Coenzyme M methyltransferase from *Methanosarcina barkeri*. Identification of the active-site histidine in the corrinoid-harboring subunit MtaC by site-directed mutagenesis," *Eur. J. Biochem.* 253(3):698-705 (1998).

Sauer et al., "Methanol:Coenzyme M methyltransferase from *Methanosarcina barkeri*. Purification, properties and encoding genes of the corrinoid protein MT1," *Eur. J. Biochem.* 243(3):670-677 (1997).

Sauer, "Diels-Alder Reactions II: The Reaction Mechanism," *Angew. Chem. Int. Ed.* 6:16-33 (1967).

Sauvageot et al., "Characterisation of the diol dehydratase pdu operon of *Lactobacillus collinoides*," *FEMS Microbiol. Lett.* 209:69-74 (2002).

Sawers and Boxer, "Purification and properties of membrane-bound hydrogenase isoenzyme 1 from anaerobically grown *Escherichia coli* K12," *Eur. J. Biochem.* 156(2):265-275 (1986).

Sawers et al., "Characterization and physiological roles of membrane-bound hydrogenase isoenzymes from *Salmonella typhimurium*," *J. Bacteriol.* 168(1):398-404 (1986).

Sawers et al., "Differential expression of hydrogenase isoenzymes in *Escherichia coli* K-12: evidence for a third isoenzyme," *J. Bacteriol.* 164(3):1324-1331 (1985).

Sawers, "The hydrogenases and formate dehydrogenases of *Escherichia coli*," *Antonie Van Leeuwenhoek* 66(1-3):57-88 (1994).

Saz and Weil, "The mechanism of the formation of α-methylbutyrate from carbohydrate by *Ascaris lumbricoides* muscle," *J. Biol. Chem.* 235:914-918 (1960).

Schadt et al., "2-Amino-2-deoxyisochorismate is a key intermediate in *Bacillus subtilis* p-aminobenzoic acid biosynthesis," *J. Am. Chem. Soc.* 131:3481-3483 (2009).

Scher and Jakoby, "Maleate isomerase," *J. Biol. Chem.* 244:1878-1882 (1969).

Scherf and Buckel, "Purification and properties of 4-hydroxybutyrate Coenzyme A transferase from *Clostridium aminobutyricum*," *Appl. Environ. Microbiol.* 57(9):2699-2702 (1991).

Scherf and Buckel, "Purification and properties of an iron-sulfur and FAD-containing 4-hydroxybutyryl-CoA dehadratase/vinylacetyl-CoA $\Delta^3$—$\Delta^2$-isomerase from *Clostridium aminobutricum*," *Eur. J. Biochem.* 215:421-429 (1993).

Scherf et al, "Succinate-ethanol fermentation in *Clostridium kluyveri*: purification and characterisation of 4-hydroxybutyryl-CoA dehydratase/vinylacetyl-CoA $\Delta^3$—$\Delta^2$-isomerase," *Arch. Microbiol.* 161(3):239-245 (1994).

Schilling et al., "Genome-Scale Metabolic Model of *Helicobacter pylori* 26695," *J. Bacteriol.* 184:4582-4593 (2002).

Schilling et al., "Combining Pathway Analysis with Flux Balance Analysis for the Comprehensive Study of Metabolic Systems," *Biotechnol. Bioeng.* 71(4):286-306 (2000/2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schilling et al., "Toward Metabolic Phenomics: Analysis of Genomic Data Using Flux Balances," *Biotechnol. Prog.* 15(3):288-295 (1999).

Schmid et al., "Plasmid-mediated uptake and metabolism of sucrose by *Escherichia coli* K-12," *J. Bacteriol.* 151(1):68-76 (1982).

Schmitzberger et al., "Structural constraints on protein self-processing in L-aspartate-α-decarboxylase," *EMBO J.* 22:6193-6204 (2003).

Schneider and Betz, "Waxmonoester Fermentation in *Euglenagracilis* T Factors Favoring the Synthesis of Odd-Numbered Fatty-Acids and Alcohols," *Planta.* 166:67-73 (1985).

Schneider et al., "The *Escherichia coli* gabDTPC operon: specific γ-aminobutyrate catabolism and nonspecific induction," *J. Bacteriol.* 184:6976-6986 (2002).

Schnell et al., "Anaerobic degradation of aniline and dihydroxybenzenes by newly isolated sulfate-reducing bacteria and description of *Desulfobacterium anilini*," *Arch. Microbiol.* 152:556-563 (1989).

Schousboe et al., "Purification and Characterization of the 4-Aminobutyrate-2-Ketoglurate Transminase from Mouse Brain," *Biochem.* 2(15):2868-2873 (1973).

Schrock et al., "Preparation and Reactivity of Several Alkylidene Complexes of the Type W(CHR')(N-2, 6-$C_6H_3$-i-$Pr_2$)$(OR)_2$ and Related Tungstacyclobutane complexes. Controlling Metathesis Activity through the Choice of Alkoxide Ligand," *J. Am. Chem. Soc.* 110:1423-1435 (1988).

Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).

Schurmann and Sprenger, "Fructose-6-phosphate aldolase is a novel class I aldolase from *Escherichia coli* and is related to a novel group of bacterial transaldolases," *J. Biol. Chem.* 276(14): p. 11055-11061 (2001).

Schwarzer et al., "Nonribosomal peptides: from genes to products," *Nat. Prod. Rep.* 20:275-287 (2003).

Schweiger and Buckel, "On the dehydration of (R)-lactate in the fermentation of alanine to propionat by *Clostridium propionicum*," *FEBS Lett.* 171:79-84 (1984).

Schweiger et al., "Purification of 2-hydroxyglutaryl-CoA dehydratase from *Acidaminococcus fermentans*. An iron-sulfur protein," *Eur. J. Biochem.* 169(2):441-448 (1987).

Scott and Jakoby, "Soluble γ-Aminobutyric-Glutamic Transaminase from *Pseudomonas fluorescens*," *J. Biol. Chem.* 234:932-936 (1959).

Scott, A.I., "Discovering nature's diverse pathways to vitamin $B_{12}$: a 35-year odyssey," *J. Org. Chem.* 68:2529-2539 (2003).

Seedorf et al., "The genome of *Clostridium kluyveri*, a strict anaerobe with unique metabolic features," *Proc. Natl. Acad. Sci. U.S.A.* 105(6):2128-2133 (2008).

Seffernick et al., "Melamine deaminase and Atrazine chlorohydrolase: 98 percent identical but functionally different," *J. Bacteriol.* 183 (8):2405-2410 (2001).

Segre et al., "Analysis of optimality in natural and perturbed metabolic networks," *Proc. Natl. Acad. Sci. U.S.A.* 99:15112-15117 (2002).

Seibert et al., "Characterization of a gene cluster encoding the maleylacetate reductase from *Ralstonia eutropha* 335T, and enzyme recruited for growth with 4-fluorobenzoate," *Microbiology* 150:463-472 (2004).

Seibert et al., "Characterization of the maleylacteate reductase MacA of *Rhodococcus opacus* 1CP and evidence for the presence of an isofunctional enzyme," *J. Bacteriol.* 180:3503-3508 (1998).

Seibert et al., "Purification and characterization of maleylacetate reductase from *Alcaligenes eutrophys* JMP134(pJP4)," *J. Bacteriol.* 175:6745-6754 (1993).

Selifonova et al., "Rapid evolution of novel traits in microorganisms," *Appl Environ Microbiol.* 67:3645-3649 (2001).

Selmer et al., "Propionate CoA-transferase from *Clostridium propionicum*. Cloning of gene identification of glutamate 324 at the active site," *Eur. J. Biochem.* 269:372-380 (2002).

Seltzer, "Purification and properties of maleylacetone cis-trans isomerase from *Vibrio* 01," *J. Biol. Chem.* 248:215-222 (1973).

Sen et al., "Developments in directed evolution for improving enzyme functions," *Appl. Biochem. Biotechnol.* 143:212-223 (2007).

Sennett et al., "Transmembrane transport of cobalamin in prokaryotic and eukaryotic cells," *Ann. Rev. Biochem.* 50:1053-1086 (1981).

Seravalli et al., "Evidence that NiNi acetyl-CoA synthase is active and that the CuNi enzyme is not," *Biochemistry* 43(13):3944-3955 (2004).

Seravalli et al., "Mechanism of transfer of the methyl group from (6S)-methyltetrahydrofolate to the corrinoid/iron-sulfur protein catalyzed by the methyltransferase from *Clostridium thermoaceticum*: a key step in the Wood-Ljungdahl pathway of acetyl-CoA synthesis," *Biochemistry* 38(18):5728-5735 (1999).

Seyfried et al., "Cloning, Sequencing, and Overexpression of the Genes Encoding Coenzyme $B_{12}$-Dependent Glycerol Dehydratase of *Citrobacter freundii*," *J. Bacteriol.* 178(19):5793-5796 (1996).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen regulation and the glycolysis pathway in *Eschericiha coli* under microaerobic growth conditions," *Biotechnol. Bioeng.* 92(2):147-159 (2005).

Shames et al., "Interaction of Aspartate and Aspartate-derived Antimetabolites with the Enzymes of the Threonine Biosynthetic Pathway of *Escherichia coli*," *J. Biol. Chem.* 258(24):15331-15339 (1984).

Shanley et al., "Cloning and expression of *Acinetobacter calcoaceticus* catBCDE genes in *Pseudomonas putida* and *Escherichia coli*," *J. Bacteriol.* 165:557-563 (1986).

Shao et al., "Random-priming in vitro recombination: an effective tool for directed evolution," *Nucleic Acids Res.* 26:681-683 (1998).

Sharma et al., "Menaquinone (Vitamin $K_2$) Biosynthesis: Nucleotide Sequence and Expression of themenB Gene from *Escherichia coli*," *J. Bacteriol.* 174(15): 5057-5062 (1992).

Sheppard et al., "Purification and Properties of NADH-Dependent 5,10-Methylenetetrahydrofolate Reductase (MetF) from *Escherichia coli*," *J. Bacteriol.* 181(3):718-725 (1999).

Shi et al., "The Structure of l-Aspartate Ammonia-Lyase from *Escherichia coli*," *Biochemistry* 36:9136-9144 (1997).

Shiba et al., "Engineering of the pyruate dehydrogenase bypass in *Saccharomyces cerevisiae* for high-level production of isoprenoids," *Metab. Eng.* 9:160-168 (2007).

Shibata et al., "Purification, characterization, and immunological properties of fumarase from *Euglena gracilis* var. bacillaris," *J. Bacteriol.* 164(2):762-768 (1985).

Shigeoka and Nakano, "Characterization and molecular properties of 2-oxoglutarate decarboxylase from *Euglena gracilis*," *Arch. Biochem. Biophys.* 288:22-28 (1991).

Shigeoka and Nakano, "The effect of thiamin on the activation of thiamin pyrophosphate-dependent 2-oxoglutarate decarboxylase in *Euglena gracilis*," *Biochem. J.* 292 (Pt 2):463-467 (1993).

Shigeoka et al., "Effect of L-glutamate on 2-oxoglutarate decarboxylase in *Euglena gracilis*," *Biochem. J.* 282 ( Pt 2):319-323 (1992).

Shimaoka et al, "Effects of edd and pgi Disruptions on Inosine Accumulation in *Escherichia coli*," *Biosci. Boitechnol. Biochem.* 69(7):1248-1255 (2005).

Shimoda et al., "Asymmetric Transformation of Enones with *Synechococcus* sp. PCC 7943," *Bulletin of the Chemical Society of Japan* 77(12):2269-2272 (2004).

Shimomura et al., "3-hydroxyisobutyryl-CoA hydrolase," *Methods Enzymol.* 324:229-240 (2000).

Shimomura et al., "Purification and partial characterization of 3-hydroxyisobutyryl—Coenzyme A hydrolase of rat liver," *J. Biol. Chem.* 269(19):14248-14253 (1994).

Shimoyama et al., "MmcBC in *Pelotomaculum thermopropionicum* represents a novel group of prokaryotic fumarases," *FEMS Microbiol Lett.* 270(2):207-213 (2007).

Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).

Shlomi et al., "Regulatory on/off minimization of metabolic flux changes after genetic perturbations," *Proc. Natl. Acad. Sci. U.S.A.* 102:7695-7700 (2005).

Shukla et al., "Production of D(−)-lactate from sucrose and molasses," *Biotechnol. Lett.* 26(9):689-693 (2004).

Shuler and Kargi, Operating Considerations for Bioreactors for Suspension and Immobilized Cultures, in *Bioprocess Engineering: Basic Concepts*, Prentice Hall, Inc., Upper Saddle River, NJ., p. 245-247 (2002).

Sibilli et al., "Two regions of the bifunctional protein aspartokinase I-homoserine dehydrogenase I are connected by a short hinge," *J. Biol. Chem.* 256 (20):10228-10230 (1981).

Sieber et al., "Libraries of hybrid proteins from distantly related sequences," *Nat. Biotechnol.* 19:456-460 (2001).

Siegert et al., "Exchanging the substrate specificities of pyruvate decarboxylase from *Zymomonas mobilis* and benzoylformate decarboxylase from *Pseudomonas putida*," *Protein. Eng. Des. Sel.* 18:345-357 (2005).

Siew et al., "Localization and characteristics of rat liver mitochondrial aldehyde dehydrogenases," *Arch. Biochem. Biophys.* 176(2):638-649 (1976).

Sikorski and Heiter, "A system of shuttle vectors and yeast host strains designed for efficient manipulation of DNA in *Saccharomyces cerevisiae*," *Genetics* 122(1):19-27 (1989).

Simanshu et al., "Structure and function of enzymes involved in the anaerobic degradation of L-threonine to propionate," *J. Biosci.* 32(6):1195-1206 (2007).

Siminov et al., "Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Simon et al., "Chiral Compounds Synthesized by Biocatalytic Reductions," *Angew. Chem. Int. Ed. Engl.* 24:539-553 (1985).

Sinclair et al., "Purification and characterization of the branched chain α-ketoacid dehydrogenase complex from *Saccharomyces cerevisiae*," *Biochem. Mol. Biol. Int.* 31(5):911-922 (1993).

Sipma et al., "Microbial CO conversions with applications in synthesis gas purification and bio-desulfurization," *Crit. Rev. Biotechnol.* 26:41-65 (2006).

Sivaraman et al., "Codon choice in genes depends on flanking sequence information—implications for theoretical reverse translation," *Nucleic Acids Res.* 36(3):e16 (2008).

Sjöström et al., "Purification and characterisation of a plasminogen-binding protein from *Haemophilus influenzae*. Sequence determination reveals identity with aspartase," *Biochim. Biophys. Acta* 1324(2):182-190 (1997).

Skarstedt and Silverstein, "*Escherichia coli* acetate kinase mechanism studied by net initial rate, equilibrium, and independent isotopic exchange kinetics," *J. Biol. Chem.* 251:6775-6783 (1976).

Slater et al., "Multiple β-ketothiolases mediate poly(β-hydroxyalkanoate) copolymer synthesis in *Ralstonia eutropha*," *J. Bacteriol.* 180(8):1979-1987 (1998).

Sloane et al., "Studies on the metabolism of p-aminobenzoic acid by *Mycobacterium smegmatis*," *J Biol. Chem.* 193:453-458 (1951).

Slock et al., "An apparent *Bacillus subtilis* folic acid biosynthetic operon containing pab, an amphibolic *trpG* gene, a third gene required for synthesis of para-aminobenzoic acid, and the dihydropteroate synthase gene," *J. Bacteriol.* 172:7211-7226 (1990).

Smit et al., "Identification, cloning and characterization of *Lactococcus lactis* branched-chain α-keto acid decarboxylase involved in flavor formation," *Appl. Environ. Microbiol.* 71:303-311 (2005).

Smith and Gray, "Catalysis of the oxidation of 1,4-cyclohexadiene to benzene by electroactive binuclear rhodium complexes," *Catalysis Lett.* 6:195-199 (1990).

Smith and Kaplan, "Purification, properties and kinetic mechanism of Coenzyme A—linked aldehyde dehydrogenase from *Clostridium kluyveri*," *Arch. Biochem. Biophys.* 203:663-675 (1980).

Smith et al., "Purification and characteristics of a γ-glutamyl kinase involved in *Escherichia coli* proline biosynthesis," *J. Bacteriol.* 157:545-551 (1984).

Smith et al., "Fumarate metabolism and the microaerophily of *Campylobacter* species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Actin polymerization induced by calspectin, a calmodulin-binding spectrin-like protein," *FEBS Lett* 148(2):221-225 (1982).

Soda and Misono, "L-Lysine:α-ketoglutarate aminotransferase. II. Purification, crystallization, and properties," *J. Bacteriol.* 7:4110-4119 (1968).

Söhling and Gottschalk, "Molecular analysis of the anaerobic succinate degradation pathway in *Clostridium kluyveri*," *J. Bacteriol.* 178:871-880 (1996).

Söhling and Gottschalk, "Purification and characterization of a Coenzyme-A-dependent succinate-semialdehyde dehydrogenase from *Clostridium kluyveri*," *Eur. J. Biochem.* 212:121-127 (1993).

Soini et al., "High cell density media for *Escherichia coli* are generally designed for aerobic cultivations—consequences for large-scale bioprocesses and shake flask cultures," *Microb. Cell. Fact.* 7:26 (2008).

Sokatch et al., "Purification of a Branched-Chain Keto Acid Dehydrogenase from *Pseudomonas putida*," *J. Bacteriol.* 148(2):647-652 (1981).

Somerville, "The Billion-Ton Biofuels Vision," *Science* 312(5778):1277 (2006).

Sone et al., "Nucleotide sequence and expression of the *Enterobacter aerogenes* α-acetolactate decarboxylase gene in brewer's yeast, " *Appl. Environ. Microbiol.* 54:38-42 (1988) .

Song et al, "Effects of dissolved $CO_2$ levels on the growth of *Mannheimia succinicproducens* and succinic acid production," *Biotechnol. Bioeng.* 98(6):1296-1304 (2007).

Song et al., "Construction of recombinant *Escherichia coli* strains producing poly (4-hydroxybutyric acid) homopolyester from glucose," *Wei Sheng Wu Xue.Bao.* 45:382-386 (2005).

Song et al., "Ultrasound-mediated DNA transfer for bacteria," *Nucl. Acids Res.* 35:e129 (2007).

Song et al., "Recovery of succinic acid produced by fermentation of a metabolically engineered *Mannheimia succiniciproducens* strain," *J. Biotechnol.* 132:445-452 (2007).

Song et al., "Structure, function, and mechanism of the phenylacetate pathway hot dog-fold thioesterase PaaI," *J. Biol. Chem.* 281(16):11028-11038 (2006).

Soucaille et al., "Butanol tolerance and autobacteriocin production by *Clostridium acetobutylicum*," *Curr. Microbiol.* 14:295-299 (1987).

Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek and Frerman, "Purification and properties of *Escherichia coli* Coenzyme A-transferase," *Arch. Biochem. Biophys.* 171(1):14-26 (1975).

St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).

Stadtman, "The enzyme synthesis of β-alanyl Coenzyme A," *J. Plant Chem. Soc.* 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of *Salmonella enerica* on ethanolamine requires phosphotransacetylase (EutD) activity, and acetate recapture requires acetyl-CoA synthetase (Acs) and phosphotransacetylase (Pta) activities," *Microbiology* 151:3793-3801 (2005).

Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005).

Starnes et al., "Threonine-sensitive aspartokinase-homoserine dehydrogenase complex, amino acid composition, molecular weight, and subunit composition of the complex," *Biochemistry* 11:677-687 (1973).

Steen et al., "Metabolic engineering of *Saccharomyces cerevisiae* for the production of n-butanol," *Microb. Cell Fact.* 7:36 (2008).

Steffan and McAlister-Henn, "Isolation and characterization of the yeast gene encoding the MDH3 isozyme of malate dehydrogenase," *J. Biol. Chem.* 267:24708-24715 (1992).

Steinbacher et al., "Enoate reductase family," in Flavins and Flavoproteins, Proceedings of the Fourteenth International Symposium, St. John's College, University of Cambridge, UK, Jul. 14-18 2002, Chapman et al., pp. 941-949, Rudolf Weber, Agency for Scientific Publications Berlin.

Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem.* 141:555-564 (1984).

Steiner and Sauer, "Long-term continuous evolution of acetate resistant *Acetobacter aceti*," *Biotechnol. Bioeng.* 84:40-44 (2003).

Stemmer, "DNA shuffling by random fragmentation and reassembly: in vitro recombination for molecular evolution," *Proc. Natl. Acad. Sci. U.S.A.* 91:10747-10751 (1994).

Stemmer, "Rapid evolution of a protein in vitro by DNA shuffling," *Nature* 370:389-391 (1994).

Stim-Herndon et al., "Characterization of an acetyl-CoA C-acetyltransferase (thiolase) gene from *Clostridium acetobutylicum* ATCC 824," *Gene* 154(1):81-85 (1995).

Stirling and Perry, "Purification and Properties of a Nicotinamide Adenine Dinucleotide-Linked Cyclohexanol Dehydrogenase from a cocardia Species," *Curr. Microbiol.* 4:37-40 (1980).

Stokell et al., "Probing the roles of key residues in the unique regulatory NADH binding site of type II citrate synthase of *Escherichia coli*," *J. Biol. Chem.* 278:35435-35443 (2003).

Stols and Donnelly, "Production of succinic acid through overexpression of $NAD^+$-dependent malic enzyme in an *Escherichia coli* mutant," *Appl. Environ. Microbiol.* 63(7):2695-2701 (1997).

Stols et al., "Expression of *Ascaris suum* malic enzyme in a mutant *Escherichia coli* allows production of succinic acid from glucose," *Appl. Biochem. Biotechnol.* 63-65: 153-158 (1997).

Stols et al., "New vectors for co-expression of proteins: Structure of *Bacillus subtilis* ScoAB obtained by High-throughput protocols," *Protein Expr. Purif.* 53:396-403 (2007).

Stoyan et al., "Cloning, sequencing and overexpression of the leucine dehydrogenase gene from *Bacillus cereus*," *J. Biotechnol.* 54:77-80 (1997).

Straathof et al., "Feasibility of acrylic acid production by fermentation," *Appl. Microbiol. Biotechnol.* 67:727-734 (2005).

Strauss and Fuchs, "Enzymes of a novel autotrophic $CO_2$ fixation pathway in the phototrophic bacterium *Chloroflexus aurantiacus*, the 3-hydroxypropionate cycle," *Eur. J. Biochem.* 215:633-643 (1993).

Streit and Entcheva, "Biotin in microbes, the genes involved in its biosynthesis, its biochemical role and perspectives for biotechnological production," *Appl. Microbiol. Biotechnol.* 61:21-31 (2003).

Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," *Gene* 166:73-76 (1995).

Stryer, *Biochemistry*. 3rd Ed. New York: W.H. Freeman and Company, pp. 374-376 (1988).

Suarez de Mata et al., "Propionyl-CoA condensing enzyme from Ascaris muscle mitochondria. I. Isolation and characterization of multiple forms," *Arch. Biochem. Biophys.* 285(1):158-165 (1991).

Suarez de Mata et al., "Propionyl-CoA condensing enzyme from Ascaris muscle mitochondria. II. Coenzyme A modulation," *Arch. Biochem. Biophys.* 285:166-171 (1991).

Suda et al., "Purification and properties of α-ketoadipate reductase, a newly discovered enzyme from human placenta," *Arch. Biochem. Biophys.* 176(2):610-620 (1976).

Suda et al., "Subcellular localization and tissue distribution of α-ketoadipate reduction and oxidation in the rat," *Biochem. Biophys. Res. Commun.* 77(2):586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E.coli* alcohol dehydrogenase YqhD: evidence of a covalently modified NADP Coenzyme," *J. Mol. Biol.* 342(2):489-502 (2004).

Suthers et al., "Metabolic flux elucidation for large-scale models using $^{13}C$ labeled isotopes," *Metab. Eng.* 9:387-405 (2007).

Suzuki et al., "Acetylputrescine deacetylase from *Micrococcus luteus* K-11," *Biochim. Biophys. Acta* 882:140-142 (1986).

Suzuki et al., "GriC and GriD Constitute a carboxylic acid reductase involved in grixazone biosynthesis in *Streptomyces griseus*," *J. Antibiot.* 60(6):380-387 (2007).

Suzuki et al., "Properties and metabolic role of mesaconate hydratase of an aerobic bacterium," *J. Biochem.* 81:1917-1925 (1977).

Suzuki, "Phospotransacetylase of *Escherichia coli* B., activation by pyruvate and inhibition by NADH and certain nucleotides," *Biochem. Biophys. Acta* 191:559-569 (1969).

Svensson et al., "Characterization and isolation of enzymes that hydrolyze short-chain acyl-CoA in rat-liver mitochondria," *Eur. J. Biochem.* 238(2):526-531 (1996).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. U.S.A.* 101(2):446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).

Switzer, "Glutamate mutase," In Dolphin, D. ed., *Vitamin $B_{12}$* (vol. 2: *Biochemistry and Medicine)*, Wiley-Interscience: New York, p. 289-305 (1982).

Tae-Kang et al., "Purification and characterization of a cyclohexanol dehydrogenase from *Rhodococcus* sp. TK6," *J. Microbiol. Biotechnol.* 12:39-45 (2002).

Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).

Takacs et al., "Formate hydrogenlyase in the hyperthermophilic archaeon, *Thermococcus litoralis*," *BMC Microbiol.* 8:88 (2008).

Takagi et al, "Purification, crystallization, and molecular properties of aspartase from *Pseudomonas fluorescens*," *J. Biochem.* 96(2):545-552 (1984).

Takagi et al., "Isolation of a versatile *Serratia marcescens* mutant as a host and molecular cloning of the aspartase gene," *J. Bacteriol.* 161:1-6 (1985).

Takagi et al., "Cloning and nucleotide sequence of the aspartase gene of *Pseudomonas fluorescens*," *J. Biochem.* 100(3):697-705 (1986).

Takahashi and Yamada, "Metabolic pathways for cytoxic and end product formation from glutamate- and aspartate-containing peptides by *Porphyromonas gingivalis*," *J. Bacteriol.* 182:4704-4710 (2000).

Takahashi-Abbe et al., "Biochemical and functional properties of a pyruvate formate-lyase (PFL)-activating system in *Streptococcus mutans*," *Oral Microbiol. Immunol.* 18:293-297 (2003).

Takanashi et al., "Characterization of a novel 3-hydroxybutyrate dehydrogenase from *Ralstonia pickettii* T1," *Antonie van Leeuwnhoek* 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).

Takatsuka et al., "Identification of the amino acid residues conferring substrate specificity upon *Selenomonas ruminantium* lysine decarboxylase," *Bioxci. Biotechnol. Biochem.* 63:1843-1846 (1999).

Takeo, "Existence and Properties of Two Malic Enzymes in *Escherichia coli* Especially of NAD-linked Enzyme," *J. Biochem.* 66:379-387 (1969).

Takigawa et al., "Probabilistic path ranking based on adjacent pairwise coexpression for metabolic transcripts analysis," *Bioinform.* 24(2):250-257 (2008).

Tallant and Krzycki, "Coenzyme M methylase activity of the 480-kilodalton corrinoid protein from *Methanosarcina barkeri*," *J. Bacteriol.* 178(5):1295-1301 (1996).

Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).

Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).

Tamaki et al., "Purification, properties, and sequencing of aminoisobutyrate aminotransferases from rat liver," *Methods Enzymol.* 324:376-389 (2000).

Tanaka et al., "Cloning and characterization of a human orthologue of testis-specific succinyl CoA: 3-oxo acid CoA transferase (Scot-t) cDNA," *Mol. Hum. Reprod.* 8:16-23 (2002).

Tanaka et al., "Lysine decarboxylase of *Vibrio parahaemolyticus*: kinetics of transcription and role in acid resistance," *J. Appl. Microbiol.* 104:1283-1293 (2008).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable $NADP^+$-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanizawa et al., "The primary structure of thermostable D-amino acid aminotransferase from a thermophilic *Bacillus* species and its correlation with L-amino acid aminotransferases," *J. Biol. Chem.* 264(5):2450-2454 (1989).

Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).

Tardif et al., "Electrotransformation studies in *Clostridium cellulolyticum*," *J. Ind. Microbiol. Biotechnol.* 27(5):271-274 (2001).

Taylor and Fotheringham, "Nucleotide sequence of the *Bacillus licheniformis* ATCC 10716 dat gene and comparison of the predicted amino acid sequence with those of other bacterial species," *Biochim. Biophys. Acta* 1350(1):38-40 (1997).

Tebbe et al., "Titanium-Catalyzed Olefin Metathesis," *J. Am. Chem. Soc.* 101(17):5074-5075 (1979).

Teipel et al., "The substrate specificity of fumarase," *J. Biol. Chem.* 243:5684-5694 (1968).

ter Schure et al., "Pyruvate decarboxylase catalyzes decarboxylation of branched-chain 2-oxo acids but is not essential for fusel alcohol production by *Saccharomyces cerevisiae*," *Appl. Environ. Microbiol.* 64:1303-1307 (1998).

Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).

Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).

Thauer, "Microbiology. A Fifth Pathway of Carbon Fixation," *Science* 318:1732-1733 (2007).

Thomas et al., "Bimetallic nanocatalysts for the conversion of muconic acid to adipic acid," *Chem. Commun.* 21:1126-1127 (2003).

Thornton et al., "Primary structure of the monomer of the 12S subunit of transcarboxylase as deduced from DNA and characterizatio nof the product expressed in *Escherichia coli*," *J. Bacteriol.* 175:5301-5308 (1993).

Thykaer et al., "Metabolic network analysis of an adipoyl-7-ADCA-producing strain of *Penicillium chrysogenum*: elucidation of adipate degradation," *Metab. Eng.* 4(2):151-158 (2002).

Tian et al., "Variant tricarboxylic acid cycle in *Mycobacterium tuberculosis*: identification of $\alpha$-ketoglutarate decarboxylase," *Proc. Natl. Acad. Sci. U.S.A.* 102:10670-10675 (2005).

Tischer et al., "Purification and Some Properties of a Hitherto-Unknown Enzyme Reducing the Carbon-Carbon Double Bond of $\alpha,\beta$-Unsaturated Carboxylate Anions," *Eur. J. Biochem.* 97(1):103-112 (1979).

Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1744-1777 (1998).

Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).

Tobin et al., "Localization of the Lysine $\epsilon$-Aminotransferase (lat) and $\delta$-AminoadipyI)-L-Cysteinyl-D-Valine Synthetase (pcbAB) Genes from *Streptomyces clavuligerus* and Production of Lysine $\epsilon$-Aminotransferase Activity in *Escherichia coli*," *J. Bacteriol.* 173(19):6223-6229 (1991).

Tolentino et al., "A pH-regulated promoter for the expression of recombinant proteins in *Escherichia coli*," *Biotechnol. Lett.* 14:157-162. (1992).

Tomas et al., "Overexpression of groESL in *Clostridium acetobutylicum* Results in Increased Solvent Production and Tolerance, Prolonged Metabolism, and Changes in the Cell's Transcriptional Program," *Appl. Environ. Microbiol.* 69:4951-4965 (2003).

Toraya et al., "Substrate Specificity of Coenzyme $B_{12}$-Dependent Diol Dehydrase: Glycerol as Both a Good Substrate and a Potent Inactivator," *Biochem. Biophys. Res. Commun.* 69:475-480 (1976).

Toth et al., "The ald Gene, Encoding a Coenzyme A-Acylating Aldehyde Dehydrogenase, Distinguishes *Clostridium beijerinckii* and Two Other Solvent-Producing Clostridia from *Clostridium acetobutylicum*," *App. Environ. Microbiol.* 65(11):4973-4980 (1999).

Tretter and Adam-Vizi, "Alpha-ketoglutarate dehydrogenase: a target and generator of oxidative stress," *Philos. Trans. R. Soc. B* 360:2335-2345 (2006).

Trower et al., "Isolation and Characterization of a Cyclohexane-Metabolizing *Xanthobacter* sp.," *Appl. Environ. Microbiol.* 49(5):1282-1289 (1985).

Truscott et al., "Mechanisms of protein import into mitochondria," *Curr. Biol.* 13(8):R326-R337 (2003).

Tsao et al., "Production of multifunctional organic acids from renewable resources," *Adv. Biochem. Eng. Biotechnol.* 65:243-280 (1999).

Tseng et al., "Metabolic Engineering of *Escherichia coli* for Enhanced Production of (R)- and (S)-3-Hydroxybutyrate," *App. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tsujimoto et al., "$_L$-Lysine biosynthetic pathway of *Methylophilus methylotrophus* and construction of an $_L$-Lysine producer," *J. Biotechnol.* 124:327-337 (2006).

Tucci and Martin, "A novel prokaryotic trans-2-enoyl-CoA reductase from the spirochete *Treponema denticola*," *FEBS Lett.* 581(8):1561-1566 (2007).

Tutino et al., "Expression of *Sulfolobus solfataricus* trpE and trpG genes in *E. coli*," *Biochem. Biophys. Res. Commun.* 230:306-310 (1997).

Twarog and Wolfe, "Role of butyryl phosphate in the energy metabolism of *Clostridium tetanomorphum*," *J. Bacteriol.* 86:112-117 (1963).

Tyurin et al., "Electrotransformation of *Clostridum acetobutylicum* ATCC 824 using high-voltage radio frequency modulated square pulses," *J. Appl. Microbiol.* 88(2):220-227 (2000).

Tyurin et al., "Electrotransformation of *Clostridium thermocellum*," *Appl. Environ. Microbiol.* 70(2):883-890 (2004).

Tzagoloff and Dieckmann, "PET genes of *Saccharomyces cerevisiae*," *Microbiol. Rev.* 54(3):211-225 (1990).

Uchiyama et al., "Identification of the 4-Hydroxycinnamate Decarboxylase (PAD) Gene of *Klebsiella oxytoca*," *Biosci. Biotechnol. Biochem.* 72: 116-123 (2008).

Ulaganathan et al., "Structure of *Staphylococcus aureus*1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).

Umbarger and Brown, "Threonine deamination in *Escherichia coli*. II. Evidence fro two L-threonine deaminases," *J. Bacteriol.* 73(1):105-112 (1957).

Underwood et al., "Genetic Changes to Optimize Carbon Partitioning between Ethanol and Biosynthesis in Ethanologenic *Escherichia coli*," *App. Environ. Microbiol.* 68(12):6263-6272 (2002).

Urbance et al., "Evaluation of succinic acid continuous and repeat-batch biofilm fermentation by *Actinobacillus succinogenes* using plastic composite support bioreactors," *Appl. Microbiol. Biotechnol.* 65(6):664-670 (2004).

Uttaro and Opperdoes, "Purification and characterisation of a novel isopropanol dehydrogenase from *Phytomonas* sp.," *Mol. Biochem. Parasitol.* 85:213-219 (1997).

Vadali et al., "Enhanced Isoamyl Acetate Production upon Manipulation of the Acetyl-CoA node in *Escherichia coli*," *Biotech. Prog.* 20:692-697 (2004).

Vadali et al., "Production of isoamyl acetate in ackA-pta and/or *ldh* mutants of *E. coli* with overexpression of yeast ATF2," *Appl. Microbiol. Biotechnol.* 63:698-704 (2004).

Vadali et al., "Cofactor engineering of intercellular CoA/acetyl-CoA and its effect on metabolic flux redistribution in *Escherichia coli*," *Metab Eng.* 6(2): 133-139 (2004).

Valdes-Hevia and Gancedo, "Isolation and characterization of the gene encoding phosphoenolpyruvate carboxykinase from *Saccharomyces cerevisiae*," *FEBS Lett.* 258:313-316 (1989).

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227(1-2):43-60 (1995).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230(3):683-693 (1985).

Van Beilen et al., "Cloning of Baeyer-Villiger monooxygenases from comamonas, Xantherobacter and Rhodococcus using polymerase chain reaction with highly degenerate primers," *Environ. Microbiol.* 5(3):174-182 (2003).

van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

Van Der Westhuizen, et al., "Autolytic Activity and Butanol tolerance of *Clostridium acetobutylicum*," *Appl. Environ. Microbiol.* 44:1277-1281 (1982).

van Grinsven et al., "Acetate:succinate CoA-transferase in the hydrogenosomes of *Trichomonas vaginalis*: identification and characterization," *J. Biol. Chem.* 283:1411-1418 (2008).

van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).

van Maris et al., "Directed evolution of pyruvate decarboxylase-negative *Saccharomyces cerevisiae*, yielding a C2-independent, glucose-tolerant, and pyruvate-hyperproducing yeast," *Appl. Environ. Microbiol.* 7:159-166 (2004).

Van Mullem et al., "Construction of a set of *Saccharomyces cerevisiae* vectors designed for recombinational cloning," *Yeast* 20(8):739-746 (2003).

Vanderwinkel et al., "Growth of *Escherichia coli* on fatty acids: requirement for Coenzyme A transferase activity," *Biochem. Biophys. Res. Commun.* 33(6):902-908 (1968).

Vanrolleghem et al., "Validation of a Metabolic Network for *Saccharomyces cerevisiae* Using Mixed Substrate Studies," *Biotechnol. Prog.* 12(4):434-448 (1996).

Varadarajan and Miller, "Catalytic Upgrading of Fermentation-Derived Organic Acids," *Biotechnol. Prog.* 15:845-854 (1999).

Vardar-Schara et al., "Metabolically engineered bacteria for producing hydrogen via fermentation," *Microbio. Biotechnol.* 1:107-125 (2008).

Varma and Palsson, "Stoichiometric Flux Balance Models Quantitatively Predice Growth and Metabolic By-Product Secretion in Wild-Type *Escherichia coli* W3110," *Appl. Env. Microbiol.* 60(10):3724-3731 (1994).

Varma and Palsson, "Metabolic Flux Balancing: Basic Concepts, Scientific and Practical Use," *Biotechnology* 12:994-998 (1994).

Varma et al., "Biochemical Production Capabilities of *Escherichia coli*," *Biotechnol. Bioenq.* 42:59-73 (1993).

Varma et al., "Stoichiometric Interpretation of *Escherichia coli* Glucose Catabolism under Various Oxygenation Rates," *Appl. Environ. Microbiol.* 59:2465-2473 (1993).

Vazquez et al., "Phosphtransbutyrylase expression in *Bacillus megaterium*," *Curr. Microbiol.* 42:345-349 (2001).

Vega et al., "The Biological Production of Ethanol from Synthesis Gas," *Appl. Biochem. Biotechnol.* 20/21:781-797 (1989).

Vellanki et al., "Expression of hepatitis B surface antigen in *Saccharomyces cerevisiae* utilizing glyceraldehyde-3-phosphate dehydrogenase promoter of *Pichia pastoris*," *Biotechnol. Lett.* 29(2):313-318 (2007).

Vemuri et al. "Succinate production in dual-phase *Escherichia coli* fermentations depends on the time of transition from aerobic to anaerobic conditions," *J. Ind. Microbiol. Biotechnol.* 28:325-332 (2002).

Vemuri et al., "Effects of growth mode and pyruvate carboxylase on succinic acid production by metabolically engineered strains of *Escherichia coli*," *Appl. Environ. Microbiol.* 68(4):1715-1727 (2002).

Venkitasubramanian et al. *Biocatalysis in the Pharmaceutical and Biotechnology Industires*, ed. R.N. Patel, Chapter 15, pp. 425-440, CRC Press LLC, Boca Raton, FL 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Verhaert et al., "Enzyme kinetics in reversed micelles. 2. Behaviour of enoate reductase," *Eur. J. Biochem.* 187:73-79 (1990).

Vernal et al., "Cloning and heterologous expression of a broad specificity aminotransferase of *Leishmania mexicana* promastigotes," *FEMS Microbiol. Lett.* 229:217-222 (2003).

Vernal et al., "Isolation partial characterization of a broad specificity aminotransferase from *Leishmania mexicana* promastigotes," *Mol. Biochem. Parasitol.* 96:83-92 (1998).

Vey et al., "Structural basis for glycyl radical formation by pyruvate formate-lyase activating enzyme," *Proc. Natl. Acad. Sci. U.S.A.* 105:16137-16141 (2008).

Vijay et al., "Diels-Alder reactions between cyclic five-membered dienes and acetylene," *J. Mol. Struc.* 589-590:291-299 (2002).

Viola, "L-Aspartase: New Tricks From an Old Enzyme," *Adv. Enzymol. Relat. Areas. Mol. Biol.* 74:295-341 (2000).

Voellmy and Leisinger, "Role of 4-Aminobutyrate Aminotransferase in the Arginine Metabolism of *Pseudomonas aeruginosa*," *J. Bacteriol.* 128(3):722-729 (1976).

Voets et al., "Reduced intracellular ionic strength as the initial trigger for activation of endothelial volume-regulated anion channels," *Proc. Natl. Acad. Sci. U.S.A.* 96:5298-5303 (1999).

Volkert, et al., "The Δ(argF-lacZ)205(U169) Deletion Greatly Enhances Resistance to Hydrogen Peroxide in Stationary-Phase *Escherichia coli*," *J. Bact.* 176(3):1297-1302 (1994).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27:e18 (1999).

Vrijbloed et al., "Insertional inactivation of methylmalonyl Coenzyme A (CoA) mutase and isobutyryl-CoA mutase genes in *Streptomyces cinnamonensis*: influence on polyketide antibiotic biosynthesis," *J. Bacteriol.* 181(18):5600-5605 (1999).

Wakil et al., "Studies on the fatty acid oxidizing system of animal tissues. VI. β-Hydroxyacyl Coenzyme A dehydrogenase," *J. Biol. Chem.* 207(2):631-638 (1954).

Walker et al., "Yeast pyruvate carboxylase: identification of two genes encoding isoenzymes," *Biochem. Biophys. Res. Commun.* 176:1210-1217 (2007).

Walter et al., "Molecular characterization of two *Clostridium acetobutylicum* ATCC 824 butanol dehydrogenase isozyme genes," *J. Bacteriol.* 174(22):7149-7158 (1992).

Walter et al., "Sequence and arrangement of two genes of the butyrate-synthesis pathway of *Clostridium acetobutylicum* ATCC 824," *Gene* 134(1):107-111 (1993).

Wang and Barker, "Purification and Properties of L-citramalate hydrolase," *J. Biol. Chem.* 244(10):2516-2526 (1969).

Wang and Seah, "Determination of the metal ion dependence and substrate specificty of a hydratase involve din the degradation pathway of biphenyl/chlorobiphenyl," *FEBS. J.* 272: 966-974 (2005).

Wang et al, "Molecular cloning and functional identification of a novel phenylacetyl-CoA ligase gene from *Penicillium chrysogenum*," *Biochem. Biopyhs. Res. Commun.* 360(2):453-458 (2007).

Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).

Wang et al., "Bioconversion of fumaric acid to succinic acid by recombinant *E. coli*," *App. Biochem. Biotechnol.* 70-72: 919-928 (1998).

Wang et al., "Cloning, Sequencing, and Expression of the Pyruvate Carboxylase Gene in *Lactococcus lactis* subsp. *lactis* C2," *App. Environ. Microbiol.* 66(3):1223-1227 (2000).

Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).

Wang et al., "Genome-scale in silico aided metabolic analysis and flux comparisons of *Escherichia coli* to improve succinate production," *Appl. Microbiol. Biotechnol.* 73(4):887-894 (2006).

Wang et al., "Screening microorganisms for utilization of furfural and possible intermediates in its degradative pathway," *Biotechnol. Lett.* 16(9):977-982 (1994).

Wang et al., "Site-directed mutagenesis of the phosphorylatable serine (Ser$^8$) in $C_4$ phosphoenolpyruvate carboxylase from sorghum. The effect of negative charge at position 8," *J. Biol. Chem.* 267:16759-16762. (1992).

Wanner and Tressl, "Purification and characterization of two enone reductases from *Saccharomyces cerevisia*," *Eur. J. Biochem.* 255(1):271-278 (1998).

Ward et al., "Molecular analysis of the rele of two aromatic aminotransferases and a broad-specificity aminotransferase in the aromatic amino acid metabolism of *Pyococcus furiosus*," *Archaea* 1:133-141 (2002).

Weaver, "Structure of free fumarase C from *Escherichia coli*," *Acta. Crystallogr. D. Biol. Crystallogr.* 61(Pt 10):1395-1401 (2005).

Weber and Falbe, "Oxo Synthesis Technology," *Ind. Eng. Chem. Res.* 62:33-37 (1970).

Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).

Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).

Wengrovius et al., "Tungsten-Oxo Alkylidene Complexes as Olefin Metathesis Catalysts and the Crystal Structure of $W(O)(CHCMe_3)(PEt_3)Cl_2^1$," *J. Am. Chem. Soc.* 102:4515-4516 (1980).

Westin et al., "The identification of a succinyl-CoA thioesterase suggests a novel pathway for succinate production in peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbiol.* 7:1917-1926 (2006).

Whalen and Berg, "Analysis of an avtA::Mu d1(Ap lac) Mutant: Metabolic Role of Transaminase C," *J. Bacteriol.* 150(2):739-746 (1982).

Whalen and Berg, "Gratuitous repression of avtA in *Escherichia coli* and *Salmonella typhimurium*," *J. Bacteriol.* 158(2):571-574 (1984).

Whelan et al., "Nylon 6 (PA6)," *Kunststof en Rubber*, Wyt en Zonen Uitgevers. Rotterdam, NL. 39(3):38-39 (1986).

Whisstock et al., "Prediction of protein function from protein sequence and structure," *Q. Rev. Biophysics.* 36(3):307-340 (2003).

White et al., "Long-chain alcohol production by yeasts," *7th Int. Symp. Yeasts* S465-S470 (1989).

White et al., "The structural biology of type II fatty acid biosynthesis," *Ann. Rev. Biochem.* 74:791-831 (2005).

Whitehead and Rabinowitz, "Cloning and expression in *Escherichia coli* of the gene for 10-formyltetrahydrofolate synthetase from *Clostridium acidi-urici* ("*Clostridium acidiurici*")," *J. Bacteriol.* 167:205-209 (1986).

Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme $C_1$-Tetrahydrofolate Synthase from *Saccharomyces cerevisiae*," *J. Bacteriol.* 170(7):3255-3261 (1988).

Wiesenborn et al., "Coenzyme A Transferase from *Clostridium acetobutylicum* ATCC 824 and Its Role in the Uptake of Acids," *Appl. Environ. Microbiol.* 55(2):323-329 (1989).

Wiesenborn et al., "Phosphotransbutyrylase from *Clostridium acetobutylicum* ATCC 824 and its role in acidogenesis," *Appl. Environ. Microbiol.* 55:317-322 (1989).

Wilkie and Warren, "Recombinant expression, purification, and characterization of three isoenzymes of aspartate aminotransferase from *Arabidopsis thaliana*," *Protein. Expr. Purif.* 12:381-389 (1998).

Wilks et al., "A specific, Highly Active Malate Dehydrogenase by Redesign of a Lactate Dehydrogenase Framework," *Science* 242:1541-1544 (1988).

Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).

Wilks et al., "Designs for a Broad Substrate Specificity Keto Acid Dehydrogenase," *Biochemistry* 29:8587-8591 (1990).

Willke and Vorlop, "Biotechnological production of itaconic acid," *Appl. Microbiol. Biotechnol.* 56(3-4):289-295 (2001).

Willke and Vorlop, "Industrial bioconversion of renewable resources as an alternative to conventional chemistry," *Appl. Microbiol. Biotechnol.* 66(2):131-142 (2004).

Winkler et al., "A new type of a multifunctional β-oxidation enzyme in euglena," *Plant Physiol.* 131(2):753-762 (2003).

Winzeler et al., "Functional Characterization of *S. cerevisiae* Genome by Gene Deletion and Parallel Analysis," *Science* 285:901-906 (1999).

Winzer et al., "Differential regulation of two thiolase genes from *Clostridium acetobutylicum* DSM 792," *J. Mol. Microbiol. Biotechnol.* 2(4):531-541 (2000).

Witkowski et al., "Conversion of β-ketoacyl synthase to a Malonyl Decarboxylase by replacement of the active cysteine with glutamine," *Biochemistry* 38:11643-11650 (1999).

Wittich and Walter, "Putrescine *N*-acetyltransferase in *Onchocerca volvulus* and *Ascaris suum*, an enzyme which is involved in polyamine degradation and release of *N*-acetylputrescine," *Mol. Biochem. Parasitol.* 38:13-17 (1990).

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wong et al., "Molecular Properties of Pyruvate Formate-Lyase Activating Enzyme," *Biochemistry* 32:14102-14110 (1993).

Wong et al., "Sequence saturation mutagenesis (SeSaM): a novel method for directed evolution," *Nucleic Acids Res* 32:e26 (2004).

Wong et al., "Sequence saturation mutagenesis with tunable mutation frequencies," *Anal. Biochem.* 341:187-189 (2005).

Wong et al., "Transversion-enriched sequence saturation mutagenesis (SeSaM-Tv$^+$): a random mutagenesis method with consecutive nucleotide exchanges that complements the bias of error-prone PCR," *Biotechnol. J.* 3:74-82 (2008).

Wood, "Life with CO or $CO_2$ and $H_2$ as a source of carbon and energy," *Fed. Amer. Societies Experi. Biol. J.* 5:156-163 (1991).

Woods, "Two biochemically distinct classes of fumarase in *Escherichia coli*," *Biochim. Biophys. Acta* 954(1):14-26 (1988).

Wu and Woodard, "New insights into the evolutionary links relating to the 3-deoxy-D-arabino-heptulosonate 7-phosphate synthase subfamilies," *J. Biol. Chem.* 281:4042-4048 (2006).

Wu et al., "Microbial synthesis of cis-cis-muconic acid by *Sphingobacterium* sp. GcG generated from effluent of a styrene monomer (SM) production plant," *Enzyme Microbial Tech.* 35:598-604 (2004).

Wu et al., "*Thermotoga maritima* 3-deoxy-D-arabino-heptulosonate 7-phosphate (DAHP) synthase: the ancestral eubacterial DAHP synthase?" *J. Biol. Chem.* 278:27525-27531 (2003).

Wu et al., "Life in hot carbon monoxide: the complete genome sequence of *Carboxydothermus hydrogenoformans* Z-2901," *PLoS Genet.* 1(5):e65 (2005).

Wylie et al., "Nematode.net: a tool for navigating sequences from parasitic and free-living nematodes," *Nucleic Acids Res.* 32:D423-D426 (2004).

Wynn et al., "Chaperonins GroEL and GroES promote assembly of heterotetramers ($\alpha_2\beta_2$) of mammalian mitochondrial branched-chain α-keto acid decarboxylase in *Escherichia coli*," *J. Biol. Chem.* 267:12400-12403 (1992).

Wynn et al., "Cloning and expression in *Escherichia coli* of mature E1 β subunit of bovine mitochondrial branched-chain α-keto acid dehydrogenase complex. Mapping of the E1 β-binding region on E2," *J. Biol. Chem.* 267:1881-1887 (1992).

Yabutani et al., "Analysis of β-ketothiolase and acetoacetyl-CoA reductase genes of a methylotrophic bacterium, *Paracoccus denitrificans*, and their expression in *Escherichia coli*," *FEMS Microbiol. Lett.* 133:85-90 (1995).

Yagi et al., "Aspartate: 2-oxoglutarate aminotransferase from bakers' yeast: crystallization and characterization," *J. Biochem.* 92(1):35-43 (1982).

Yagi et al., "Crystallization and properties of aspartate aminotransferase from *Escherichia coli* B," *FEBS Lett.* 100(1):81-84 (1979).

Yagi et al., "Glutamate-aspartate transaminase from microorganisms," *Methods. Enzymol.* 113:83-89 (1985).

Yamamoto et al., "Carboxylation reaction catalyzed by 2-oxoglutarate:ferredoxin oxidoreductases from *Hydrogenobacter thermophilus*," *Extremophiles* 14:79-85 (2010).

Yamamoto et al., "Purification and Properties of NADP-dependent Formate Dehydrogenase from *Clostridium thermoaceticum*, a tungsten-Selenium-Iron Protein," *J. Biol. Chem.* 258(3):1826-1832 (1983).

Yamano et al., "Construction of a brewer's yeast having α-acetolactate decarboxylase gene from *Acetobacter aceti* ssp. *xylinum* integrated in the genome," *J. Biotechnol.* 32:173-178 (1994).

Yan and Chen, "Coenzyme A-acylating aldehyde dehydrogenase from *Clostridium beijerinckii* NRRL B592," *Appl. Environ. Microbiol.* 56:2591-2599 (1990).

Yang et al., "Aspartate Dehydrogenase, a Novel Enzyme Identified from Structural and Functional Studies of TM1643," *J. Biol. Chem.* 278(10):8804-8808 (2003).

Yang et al., "Effect of inactivation of *nuo* and *ackA-pta* on redistribution of metabolic fluxes in *Escherichia coli*," *Biotechnol Bioeng.* 65(3):291-297 (1999).

Yang et al., "Effect of Variation of *Klebsiella pneumoniae* Acetolactate Synthase Expression on Metabolic Flux Redistribution in *Escherichia coli*," *Biotechnol. Bioeng.* 69(2)150-159 (2000).

Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).

Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).

Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).

Yang et al., "Nucleotide sequence of the promoter and fadB gene of the fadBA operon and primary structure of the multifunctional fatty acid oxidation protein from *Escherichia coli*," *Biochem.* 30(27):6788-6795 (1991).

Yang et al., "Redistribution of Metabolic Fluxes in *Escherichia coli* with Fermentative Lactate Dehydrogenase Overexpression and Deletion," *Metab. Eng.* 1:141-152 (1999).

Yang et al., "The effects of feed and intracellular pyruvate levels on the redistribution of metabolic fluxes in *Escherichia coli*," *Metab Eng.* 3(2):115-123 (2001).

Yang, "Location of the fadBA operon on the physical map of *Escherichia coli*," *J. Bacteriol.* 173(23):7405-7406 (1991).

Yanisch-Perron et al., "Improved M13 phage cloning vectors and host strains: nucleotide sequences of the M13mp18 and pUC19 vectors," *Gene* 33:103-119 (1985).

Yano et al., "Directed evolution of an aspartate aminotransferase with new substrate specificities," *Proc. Natl. Acad. Sci U.S.A.* 95:5511-5515 (1998).

Yarlett et al., "*Trichomonas vaginalis*: characterization of ornithine decarboxylase," *Biochem. J.* 293(Pt2):487-493 (1993).

Yeh and Ornston, Evolutionarily Homologous $\alpha_2\beta_2$ Oligomeric Structures in β-Ketoadipate Succinyl-CoA Transferases from *Acinetobacter calcoaceticus* and *Pseudomonas putida*, *J. Biol. Chem.* 256(4):1565-1569 (1981).

Ylianttila et al., "Crystal Structure of Yeast Peroxisomal Multifunctional Enzyme: Structural Basis for Substrate Specificity of (3R)-hydroxyacyl-CoA Dehydrogenase Units," *J. Mol. Biol.* 258:1286-1295 (2006).

Ylianttila et al., "Site-directed mutagenesis to enable and improve crystallizability of *Candida tropicalis* (3R)-hydroxyacyl-CoA dehydrogenase," *Biochem. Biophys. Res. Commun.* 324:25-30 (2004).

Yoshida et al., "The Structures of L-Rhamnose Isomerase from *Pseudomonas stutzeri* in Complexes with L-Rhamnose and D-Allose Provide Insights into Broad Substrate Specificity," *J. Mol. Biol.* 365:1505-1516 (2007).

Yoshimoto, et al., "Isolation and Characterization of the *ATF2* Gene Encoding Alcohol Acetyltransferase II in the Bottom Fermenting Yeast *Saccharomyces pastorianus*," *Yeast* 15:409-417 (1999).

Yoshioka and Hashimoto, "Ester formation by Alcohol Acetyltransferase from Brewers' Yeast," *Agric. Biol. Chem.* 45:2183-2190 (1981).

Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).

Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).

Yun et al., "ω-Amino acid:pyruvate transaminase from Alcaligenes denitrificans Y2k-2: a new catalyst for kinetic resolution of β-amino acids and amines," *Appl. Environ. Microbiol.* 70(4):2529-2534 (2004).

Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).

Zeiher and Randall, "Identification and characterization of Mitochondrial Acetyl-Coenzyme A Hydrolase from *Pisum sativum* L. Seedlings," *Plant. Physiol.* 94:20-27 (1990).

Zeikus et al., "Biotechnology of succinic acid production and markets for derived industrial products," *Appl. Microbiol. Biotechnol.* 51:545-552 (1999).

Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the Coenzyme $B_{12}$-dependent isobutyryl-CoA mutase from *Streptomyces cinnamonensis*," *J. Biol. Chem.* 273(11):6508-6517 (1998).

Zhang et al., "2-Oxoacid:Ferredoxin Oxidoreductase from the thermoacidophilic *Archaeon, sulfolobus* sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," *Proc. Natl. Acad. Sci. U.S.A.* 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fayy acids and marcrolide antibiotic production," *Microbiol.* 145 (Pt 9):2323-2334 (1999).

Zhang et al., "Isolation and properties of a levo-lactonase from *Fusarium proliferatum* ECU2002: A robust biocatalyst for production of chiral lactones," *Appl. Microbiol. Biotechnol.* 75:1087-1094 (2007).

Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by *Rhizopus oryzae* using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by *Rhizopus oryzae* ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from *Moorella thermoacetica*," *Acta. Crystallogr. Sect. F. Struct. Biol. Cryst. Commun.* 61(Pt 5):537-540 (2005).

Zhu and Sadowski, "Cleavage-dependent ligation by the FLP recombinase. Characterization of a mutant FLP protein with an alteration in a catalytic amino acid," *J. Biol. Chem.* 270(39):23044-23054 (1995).

Zhuang et al., "The YbgC protein encoded by the ybgC gene of the tol-pal gene cluster of *Haemophilus influenzae* catalyzes acyl-Coenzyme A thioester hydrolysis," *FEBS Lett.* 516(1-3):161-163 (2002).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/~FwAsma:1:BASIC (printed Feb. 17, 2010).

Two pages from URL: web.archive.org/web/20080302001450/http://www.verenium.com/Pages./Technology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

Ferreira-Torres et al., "Microscale process evaluation of recombinant biocatalyst libraries: application to Baeyer-Villiger monooxygenase catalysed lactone synthesis," *Bioprocess Biosyst. Eng.* 28(2):83-93 (2005).

Locher et al., "Crystal structure of the *Acidaminococcus fermentans* 2-hydroxyglutaryl-CoA dehydratase component A," *J. Mol. Biol.* 307(1):297-308 (2001).

Niu et al., "Benzene-free synthesis of adipic acid," *Biotechnol. Prog.* 18:201-211 (2002).

Reed et al., "An expanded genome-scale model of *Escherichia coli* K-12 (iJR904 GSM/GPR)," *Genome. Biol.* 4(9):R54 (2003).

Database Reaxys [Online] Elsevier Properties SA; RX-ID Nos. 715357 and 5957085; Volmar: Comptes Rendus Hebdomadaires Des Seances De L'Academie Des Sciences, vol. 181; (1925); p. 467 (document printed Apr. 11, 2011).

Tsuji et al., "Purification and Properties of 4-Aminobenzoate Hydroxylase, a New Monooxygenase from *Agaricus bisporus*," *J. Biol. Chem.* 261(28):13203-13209 (1986).

Nichols et al., "*para*-Aminobenzoate Synthesis from Chorismate Occurs in Two Steps," *J. Biol. Chem.* 264(15):8597-8601 (1989).

Dosselaere et al., "A Metabolic Node in Action: Chorismate-Utilizing Enzymes in Microorganisms," *Crit. Rev. Microbiol.* 27(2):75-131 (2001).

Nicolaou et al., "Total Synthesis of Abyssomicin C, Atrop-abyssomicin C, and Abyssomicin D: Implications for Natural Origins of Atrop-abyssomicin C," *J. Am. Chem. Soc.* 129(2):429-440 (2007).

Bister et al., "Abyssomicin C-A polycyclic antibiotic from a marine *Verrucosispora* strain as an inhibitor of the p-aminobenzoic acid/tetrahydrofolate biosynthesis pathway," *Angew Chem. Int. Ed. Engl.* 43(19):2574-2576 (2004).

Feist et al., "Modeling methanogenesis with a genome-scale metabolic reconstruction of *Methanosarcina barkeri*," *Mol. Syst. Biol.* 2:2006.0004 (2006).

One page from URL: <www.dtu.dk/English/Service/Phonebook.aspx?lg=showcommon&id=193466> Containing 182 page document: Patil, Ph.D. Thesis, "Systems Biology of Metabolic Networks: Uncovering Regulatory and stoichiometric Principles," 2006. (Printed from the Internet Jun. 8, 2011).

Tweedy et al., "Metabolism of 3-(p-bromophenyl)-1-methoxy-1-methylurea (metobromuron) by selected soil microorganisms," *J. Agric. Food Chem.* 18(5):851-853 (1970).

Peres et al., "Biodegradation of nitrobenzene by its simultaneous reduction into aniline and mineralization of the aniline formed," *Appl. Microbiol. Biotechnol.* 49(3):343-349 (1998).

White, "Biosynthesis of methanopterin," *Biochemistry* 35(11):3447-3456 (1996).

Genbank Accession No. AAA24013.1 GI:146451 (Apr. 26, 1993).
Genbank Accession No. AAA24929.1 GI:148711 (Apr. 26, 1993).
Genbank Accession No. AAA58352.1 GI:177198 (Dec. 31, 1994).
Genbank Accession No. AAC24332.1 GI:3253200 (Feb. 2, 2005).
Genbank Accession No. AAC37147.1 GI:141776 (Jun. 27, 2003).
Genbank Accession No. AAC38322.1 GI:3046397 (Mar. 29, 1999).
Genbank Accession No. AAC73823.1 GI:1786949 (Sep. 26, 2007).
Genbank Accession No. AAC76268.1 GI:1789632 (Sep. 26, 2007).
Genbank Accession No. AAD22035.1 GI:4530443 (Apr. 6, 2000).
Genbank Accession No. AAL02407.1 GI:17736947 (May 9, 2007).
Genbank Accession No. AAN67000.1 GI:24982839 (Jan. 10, 2006).
Genbank Accession No. AAN69545.1 GI:24985644 (Jan. 10, 2006).
Genbank Accession No. AAZ94428.1 GI:74026644 (Sep. 5, 2005).
Genbank Accession No. ABC88407.1 GI:86278275 (Aug. 18, 2006).
Genbank Accession No. ABF82233.1 GI:106636093 (Aug. 2, 2007).
Genbank Accession No. ABF82234.1 GI:106636094 (Aug. 2, 2007).
Genbank Accession No. ABF82235.1 GI:106636095 (Aug. 2, 2007).
Genbank Accession No. ABF82237.1 GI:106636097 (Aug. 2, 2007).
Genbank Accession No. ABJ15177.1 GI:115589162 (Nov. 14, 2006).
Genbank Accession No. ACA54153.1 GI:169405742 (Mar. 5, 2008).
Genbank Accession No. BAB39707.1 GI:13429872 (Feb. 26, 2004).
Genbank Accession No. BAB85476.1 GI:18857901 (Mar. 18, 2005).
Genbank Accession No. CAA15502.1 GI:3191970 (Feb. 24, 2008).
Genbank Accession No. CAA71086.1 GI:2765041 (Apr. 18, 2005).
Genbank Accession No. CAA76083.1 GI:3402834 (Apr. 18, 2005).
Genbank Accession No. EDK35586.1 GI:146349050 (Feb. 21, 2008).
Genbank Accession No. NP_149242.1 GI:15004782 (Dec. 4, 2007).
Genbank Accession No. NP_349314.1 GI:15895965 (Dec. 4, 2007).
Genbank Accession No. NP_349315.1 GI:15895966 (Dec. 4, 2007).
Genbank Accession No. NP_349316.1 GI:15895967 (Dec. 4, 2007).
Genbank Accession No. NP_349317.1 GI:15895968 (Dec. 4, 2007).
Genbank Accession No. NP_349318.1 GI:15895969 (Dec. 4, 2007).
Genbank Accession No. NP_349476.1 GI:15896127 (Dec. 4, 2007).
Genbank Accession No. NP_349675.1 GI:15896326 (Dec. 4, 2007).
Genbank Accession No. NP_349676.1 GI:15896327 (Dec. 4, 2007).
Genbank Accession No. NP_353966.1 GI:15888285 (Nov. 28, 2007).
Genbank Accession No. NP_414986.1; GI:16128437 (Dec. 20, 2007).
Genbank Accession No. NP_415027.1; GI:16128478 (Dec. 20, 2007).
Genbank Accession No. NP_415129.1; GI:16128580 (Dec. 20, 2007).
Genbank Accession No. NP_415256.1; GI:16128703 (Dec. 20, 2007).
Genbank Accession No. NP_415264.1; GI:16128711 (Dec. 20, 2007).
Genbank Accession No. NP_415705.1; GI:16129150 (Dec. 20, 2007).
Genbank Accession No. NP_415898.1; GI:16129341 (Dec. 20, 2007).
Genbank Accession No. NP_415905.1; GI:16129348 (Dec. 20, 2007).
Genbank Accession No. NP_415911.1; GI:16129354 (Dec. 20, 2007).
Genbank Accession No. NP_415912.1; GI:16129355 (Dec. 20, 2007).
Genbank Accession No. NP_415913.1; GI:16129356 (Dec. 20, 2007).
Genbank Accession No. NP_415914.1; GI:16129357 (Dec. 20, 2007).
Genbank Accession No. NP_415915.1; GI:16129358 (Dec. 20, 2007).
Genbank Accession No. NP_416728.1; GI:16130161 (Dec. 20, 2007).
Genbank Accession No. NP_416843.1; GI:16130274 (Dec. 20, 2007).
Genbank Accession No. NP_416844.1; GI:16130275 (Dec. 20, 2007).
Genbank Accession No. NP_417148.1; GI:16130576 (Dec. 20, 2007).
Genbank Accession No. NP_417321.2; GI:90111494 (Dec. 20, 2007).
Genbank Accession No. NP_417388.1; GI:16130814 (Dec. 20, 2007).

Genbank Accession No. NP_417552.1; GI:16130976 (Dec. 20, 2007).
Genbank Accession No. NP_418288.1; GI:16131692 (Dec. 20, 2007).
Genbank Accession No. NP_564034.1 GI:18394525 (Apr. 20, 2007).
Genbank Accession No. NP_570112.2; GI:51036669 (Feb. 10, 2008).
Genbank Accession No. NP_603113.1 GI:19703551 (Dec. 2, 2007).
Genbank Accession No. NP_603114.1 GI:19703552 (Dec. 2, 2007).
Genbank Accession No. NP_603115.1 GI:19703553 (Dec. 2, 2007).
Genbank Accession No. NP_630775.1 GI:21224996 (Jan. 22, 2008).
Genbank Accession No. NP_630776.1; GI:21224997 (Jan. 22, 2008).
Genbank Accession No. NP_745425.1 GI:26990000 (Nov. 30, 2007).
Genbank Accession No. NP_745426.1 GI:26990001 (Nov. 30, 2007).
Genbank Accession No. NP_745427.1 GI:26990002 (Nov. 30, 2007).
Genbank Accession No. NP_746082.1 GI:26990657 (Nov. 30, 2007).
Genbank Accession No. NP_766549.2; GI:37202121 (Feb. 10, 2008).
Genbank Accession No. NP_971211.1 GI:42526113 (Dec. 3, 2007).
Genbank Accession No. NP_999428.1; GI:47523600 (Jan. 30, 2008).
Genbank Accession No. P00926.3; GI:2507445 (Feb. 5, 2008).
Genbank Accession No. P11568.2; GI:2506909 (Jan. 15, 2008).
Genbank Accession No. P11569.2; GI:123112 (Feb. 5, 2008).
Genbank Accession No. P11570.2; GI:123113 (Feb. 5, 2008).
Genbank Accession No. P13397.2 GI:129000 (Oct. 2, 2007).
Genbank Accession No. P14407.2; GI:33112655 (Feb. 5, 2008).
Genbank Accession No. P25516.3; GI:166215073 (Feb. 5, 2008).
Genbank Accession No. P38942.2; GI:1705614 (Feb. 5, 2008).
Genbank Accession No. P38942.3; GI:172046066 (Nov. 25, 2008).
Genbank Accession No. P38946.1; GI:729048 (Feb. 5, 2008).
Genbank Accession No. P38947.1; GI:730847 (Feb. 5, 2008).
Genbank Accession No. P38947.2 GI:172046062 (Nov. 4, 2008).
Genbank Accession No. P43885.1; GI:1173427 (Feb. 5, 2008).
Genbank Accession No. Q59111.3; GI:3122155 (Feb. 5, 2008).
Genbank Accession No. Q59112.3; GI:3122156 (Feb. 5, 2008).
Genbank Accession No. Q5EU90.1 GI:62287512 (Jul. 24, 2007).
Genbank Accession No. Q97111.1; GI:20137415 (Feb. 5, 2008).
Genbank Accession No. YP_001335140.1; GI:152970031 (Dec. 4, 2007).
Genbank Accession No. YP_001479310.1; GI:157371321 (Dec. 10, 2007).
Genbank Accession No. YP_026272.1; GI:49176430 (Dec. 20, 2007).
Genbank Accession No. YP_046368.1 GI:50084858 (Nov. 29, 2007).
Genbank Accession No. YP_047869.1 GI:50086359 (Nov. 29, 2007).
Genbank Accession No. YP_257332.1 GI:70733692 (Dec. 3, 2007).
Genbank Accession No. YP_725182.1; GI:113866693 (Dec. 8, 2007).
Genbank Accession No. YP_725941.1; GI:113867452 (Dec. 8, 2007).
Genbank Accession No. YP_949627.1; GI:119961013 (Dec. 6, 2007).
Genbank Accession No. ZP_03731125.1 GI:225177592 (Mar. 17, 2009).
Genbank Accession No. ZP_03731126.1 GI:225177593 (Mar. 17, 2009).
Genbank Accession No. ZP_03731127.1 GI:225177594 (Mar. 17, 2009).

* cited by examiner

US 8,062,871 B2

MICROORGANISMS FOR THE PRODUCTION OF ADIPIC ACID AND OTHER COMPOUNDS

This application is a continuation of U.S. application Ser. No. 12/875,084, filed Sep. 2, 2010, which is a continuation of U.S. application Ser. No. 12/413,355, filed Mar. 27, 2009, now U.S. Pat. No. 7,799,545, issued Sep. 21, 2010, which claims the benefit of priority of U.S. Provisional Ser. No. 61/040,059, filed Mar. 27, 2008, each of which the entire contents are incorporated herein by reference.

BACKGROUND OF THE INVENTION

The present invention relates generally to biosynthetic processes, and more specifically to organisms having adipic acid, 6-aminocaproic acid and caprolactam biosynthetic capability.

Adipic acid, a dicarboxylic acid, with molecular weight of 146.14, is a compound of commercial significance. Its major use is to produce nylon 6,6, a linear polyamide made by condensing adipic acid with hexamethylene diamine that is primarily employed for manufacturing different kinds of fibers. Other uses of adipic acid include its use in plasticizers, unsaturated polyesters, and polyester polyols. Additional uses include for production of polyurethane, lubricant components, and as a food ingredient as a flavorant and gelling aid.

Historically, adipic acid was prepared from various fats using oxidation. The current commercial processes for adipic acid synthesis rely on the oxidation of KA oil, a mixture of cyclohexanone, the ketone or K component, and cyclohexanol, the alcohol or A component, or of pure cyclohexanol using an excess of strong nitric acid. There are several variations of this theme which differ in the routes for production of KA or cyclohexanol. For example, phenol is an alternative raw material in KA oil production, and the process for the synthesis of adipic acid from phenol has been described. The other versions of this process tend to use oxidizing agents other than nitric acid, such as hydrogen peroxide, air or oxygen.

Caprolactam is an organic compound which is a lactam of 6-aminohexanoic acid (ε-aminohexanoic acid, aminocaproic acid). It can alternatively be considered cyclic amide of caproic acid. The primary industrial use of caprolactam is as a monomer in the production of nylon-6. Most of the caprolactam is synthesised from cyclohexanone via an oximation process using hydroxylammonium sulfate followed by catalytic rearrangement using the Beckmann rearrangement process step.

Thus, there exists a need for alternative methods for effectively producing commercial quantities of compounds such as adipic acid and carpolactam. The present invention satisfies this need and provides related advantages as well.

SUMMARY OF INVENTION

The invention provides a non-naturally occurring microbial organism having an adipate, 6-aminocaproic acid or caprolactam pathway. The microbial organism contains at least one exogenous nucleic acid encoding an enzyme in the respective adipate, 6-aminocaproic acid or caprolactam pathway. The invention additionally provides a method for producing adipate, 6-aminocaproic acid or caprolactam. The method can include culturing an adipate, 6-aminocaproic acid or caprolactam producing microbial organism, where the microbial organism expresses at least one exogenous nucleic acid encoding an adipate, 6-aminocaproic acid or caprolactam pathway enzyme in a sufficient amount to produce the respective product, under conditions and for a sufficient period of time to produce adipate, 6-aminocaproic acid or caprolactam.

DETAILED DESCRIPTION OF THE INVENTION

Figure 1:
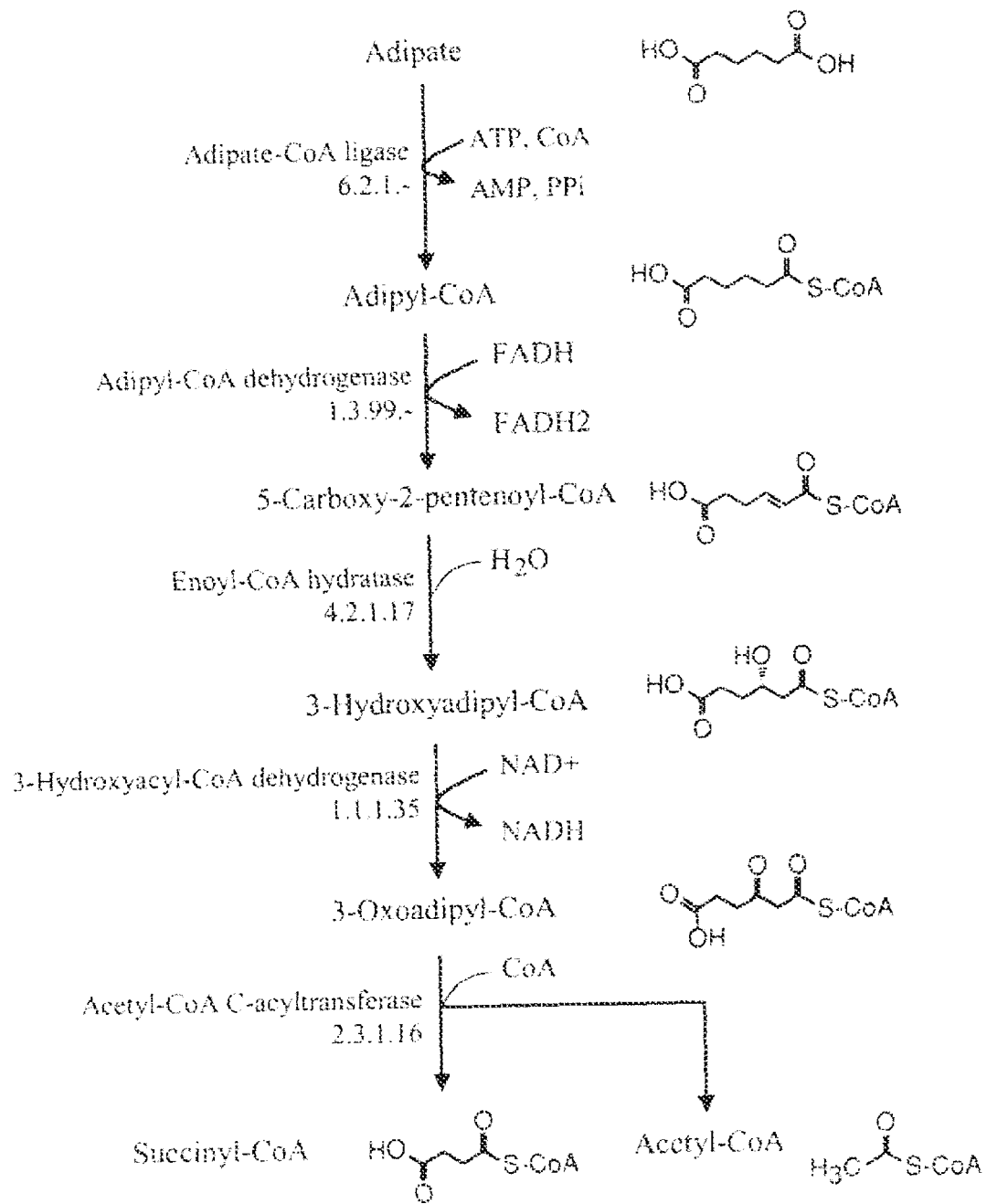
FIG. 1 shows an exemplary pathway for adipate degradation in the peroxisome of *Penicillium chrysogenum*.

The present invention is directed to the design and production of cells and organisms having biosynthetic production capabilities for adipate, 6-aminocaproic acid or caprolactam. The results described herein indicate that metabolic pathways can be designed and recombinantly engineered to achieve the biosynthesis of adipate, 6-aminocaproic acid or caprolactam in *Escherichia coli* and other cells or organisms. Biosynthetic production of adipate, 6-aminocaproic acid and caprolactam can be confirmed by construction of strains having the designed metabolic genotype. These metabolically engineered cells or organisms also can be subjected to adaptive evolution to further augment adipate, 6-aminocaproic acid or caprolactam biosynthesis, including under conditions approaching theoretical maximum growth.

As disclosed herein, a number of metabolic pathways for the production of adipate, 6-aminocaproate, and caprolactam are described. Two routes, the reverse adipate degradation pathway and the 3-oxoadipate pathway, were found to be beneficial with respect to (i) the adipate yields (92% molar yield on glucose), (ii) the lack of oxygen requirement for adipate synthesis, (iii) the associated energetics, and (iv) the theoretical capability to produce adipate as the sole fermentation product. Metabolic pathways for adipate production that pass through α-ketoadipate or lysine are also described but are lower yielding and require aeration for maximum production. A pathway for producing either or both of 6-aminocaproate and caprolactam from adipyl-CoA, a precursor in the reverse degradation pathway, is also disclosed herein.

As disclosed herein, a number of exemplary pathways for biosynthesis of adipate are described. One exemplary pathway involves adipate synthesis via a route that relies on the reversibility of adipate degradation as described in organisms such as *P. chrysogenum* (see Examples I and II). A second exemplary pathway entails the formation of 3-oxoadipate followed by its reduction, dehydration and again reduction to form adipate (see Examples III and IV). The adipate yield using either of these two pathways is 0.92 moles per mole glucose consumed. The uptake of oxygen is not required for attaining these theoretical maximum yields, and the energetics under anaerobic conditions are favorable for growth and product secretion. A method for producing adipate from glucose-derived cis,cis-muconic acid was described previously (Frost et al., U.S. Pat. No. 5,487,987, issued Jan. 30, 1996) (see Example V). Advantages of the embodiments disclosed herein over this previously described method are discussed. Metabolic pathways for adipate production that pass through α-ketoadipate (Example VI) or lysine (Example VII) precursors are lower yielding and require aeration for maximum production. A pathway for producing either or both of 6-aminocaproate and caprolactam from adipyl-CoA, a precursor in the reverse degradation pathway, is described (see Example VIII and IX). Additional pathways for producing adipate are described in Examples X and XI. Exemplary genes and enzymes required for constructing microbes with these capabilities are described as well as methods for cloning and transformation, monitoring product formation, and using the engineered microorganisms for production.

As disclosed herein, six different pathways for adipic acid synthesis using glucose/sucrose as a carbon substrate are described. For all maximum yield calculations, the missing reactions in a given pathway were added to the *E. coli* stoichiometric network in SimPheny that is similar to the one described previously (Reed et al., *Genome Biol.* 4:R54 (2003)). Adipate is a charged molecule under physiological conditions and was assumed to require energy in the form of a proton-based symport system to be secreted out of the network. Such a transport system is thermodynamically feasible if the fermentations are carried out at neutral or near-neutral pH. Low pH adipic acid formation would require an ATP-dependant export mechanism, for example, the ABC system as opposed to proton symport. The reactions in the pathways and methods of implementation of these pathways are described in Examples I-XI.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within an adipate, 6-aminocaproic acid or caprolactam biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, "adipate," having the chemical formula —OOC—$(CH_2)_4$—COO— (see FIG. 2) (IUPAC name hexanedioate), is the ionized form of adipic acid (IUPAC name hexanedioic acid), and it is understood that adipate and adipic acid can be used interchangeably throughout to refer to the compound in any of its neutral or ionized forms, including any salt forms thereof. It is understood by those skilled understand that the specific form will depend on the pH.

As used herein, "6-aminocaproate," having the chemical formula —OOC—$(CH_2)_5$—$NH_2$ (see FIG. 8), is the ionized form of 6-aminocaproic acid (IUPAC name 6-aminohexanoic acid), and it is understood that 6-aminocaproate and 6-aminocaproic acid can be used interchangeably throughout to refer to the compound in any of its neutral or ionized forms, including any salt forms thereof. It is understood by those skilled understand that the specific form will depend on the pH.

Figure 8:
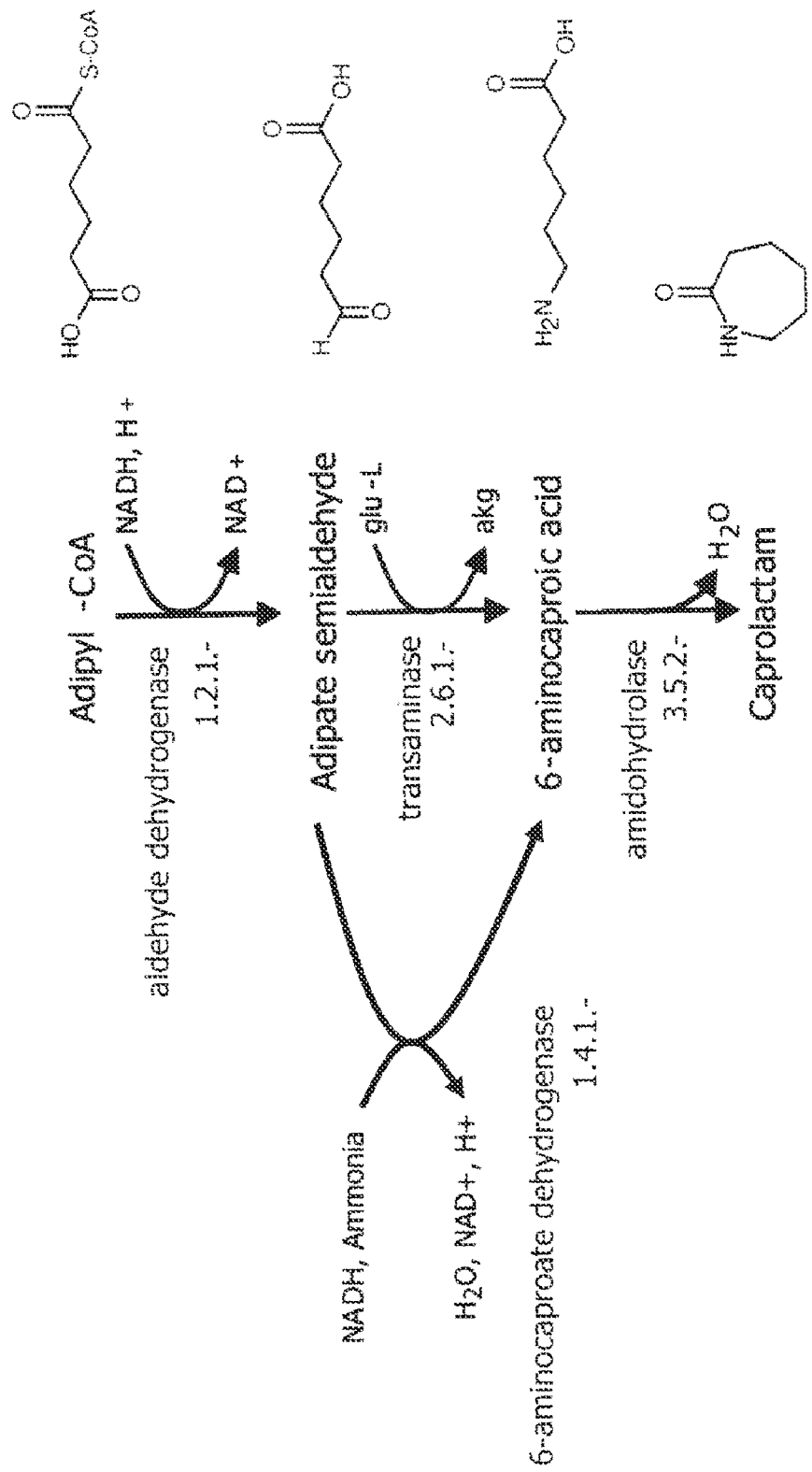
FIG. 8 shows an exemplary caprolactam synthesis pathway using adipyl-CoA as a starting point.

As used herein, "caprolactam" (IUPAC name azepan-2-one) is a lactam of 6-aminohexanoic acid (see FIG. 8).

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having adipate, 6-aminocaproic acid or caprolactam biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

The invention provides non-naturally occurring microbial organisms capable of producing adipate, 6-aminocaproic acid or caprolactam. For example, an adipate pathway can be a reverse adipate degradation pathway (see Examples I and II). In one embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In addition, an adipate pathway can be through a 3-oxoadipate pathway (see Examples III and IV). In another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising succinyl-CoA:acetyl-CoA acyl transferase, 3-oxoadipyl-CoA transferase, 3-oxoadipate reductase, 3-hydroxyadipate dehydratase, and 2-enoate reductase.

In still another embodiment, the invention provides a non-naturally occurring microbial organism having a 6-aminocaproic acid pathway comprising at least one exogenous nucleic acid encoding a 6-aminocaproic acid pathway enzyme expressed in a sufficient amount to produce 6-aminocaproic acid, the 6-aminocaproic acid pathway comprising CoA-dependent aldehyde dehydrogenase and transaminase (see Examples VIII and IX). Alternatively, 6-aminocaproate dehydrogenase can be used to convert adipate semialdehyde to form 6-aminocaproate (see FIG. 8). In a further embodiment, the invention provides a non-naturally occurring microbial organism having a caprolactam pathway comprising at least one exogenous nucleic acid encoding a caprolactam pathway enzyme expressed in a sufficient amount to produce caprolactam, the caprolactam pathway comprising CoA-dependent aldehyde dehydrogenase, transaminase or 6-aminocaproate dehydrogenase, and amidohydrolase (see Examples VIII and IX).

As disclosed herein, a 6-aminocaproic acid or caprolactam producing microbial organism of the invention can produce 6-aminocaproic acid and/or caprolactam from an adipyl-CoA precursor (see FIG. 8 and Examples VIII and IX). Therefore, it is understood that a 6-aminocaproic acid or caprolactam producing microbial organism can further include a pathway to produce adipyl-CoA. For example an adipyl-CoA pathway can include the enzymes of FIG. 2 that utilize succinyl-CoA and acetyl-CoA as precursors through the production of adipyl-CoA, that is, lacking an enzyme for the final step of converting adipyl-CoA to adipate. Thus, one exemplary adipyl-CoA pathway can include succinyl-CoA:acetyl-CoA acyl transferase, 3-hydroxyacyl-CoA dehydrogenase, 3-hydroxyadipyl-CoA dehydratase and 5-carboxy-2-pentenoyl-CoA reductase.

In addition, as shown in FIG. 1, an adipate degradation pathway includes the step of converting adipate to adipyl-CoA by an adipate CoA ligase. Therefore, an adipyl-CoA pathway can be an adipate pathway that further includes an enzyme activity that converts adipate to adipyl-CoA, including, for example, adipate-CoA ligase activity as in the first step of FIG. 1 or any of the enzymes in the final step of FIG. 2 carried out in the reverse direction, for example, any of adipyl-CoA synthetase (also referred to as adipate Co-A ligase), phosphotransadipylase/adipate kinase, adipyl-CoA:acetyl-CoA transferase or adipyl-CoA hydrolase. An enzyme having adipate to adipyl-CoA activity can be an endogenous activity or can be provided as an exogenous nucleic acid encoding the enzyme, as disclosed herein. Thus, it is understood that any adipate pathway can be utilized with an adipate to adipyl-CoA enzymatic activity to generate an adipyl-CoA pathway. Such a pathway can be included in a 6-aminocaproic acid or caprolactam producing microbial organism to provide an adipyl-CoA precursor for 6-aminocaproic acid and/or caprolactam production.

Figure 6:
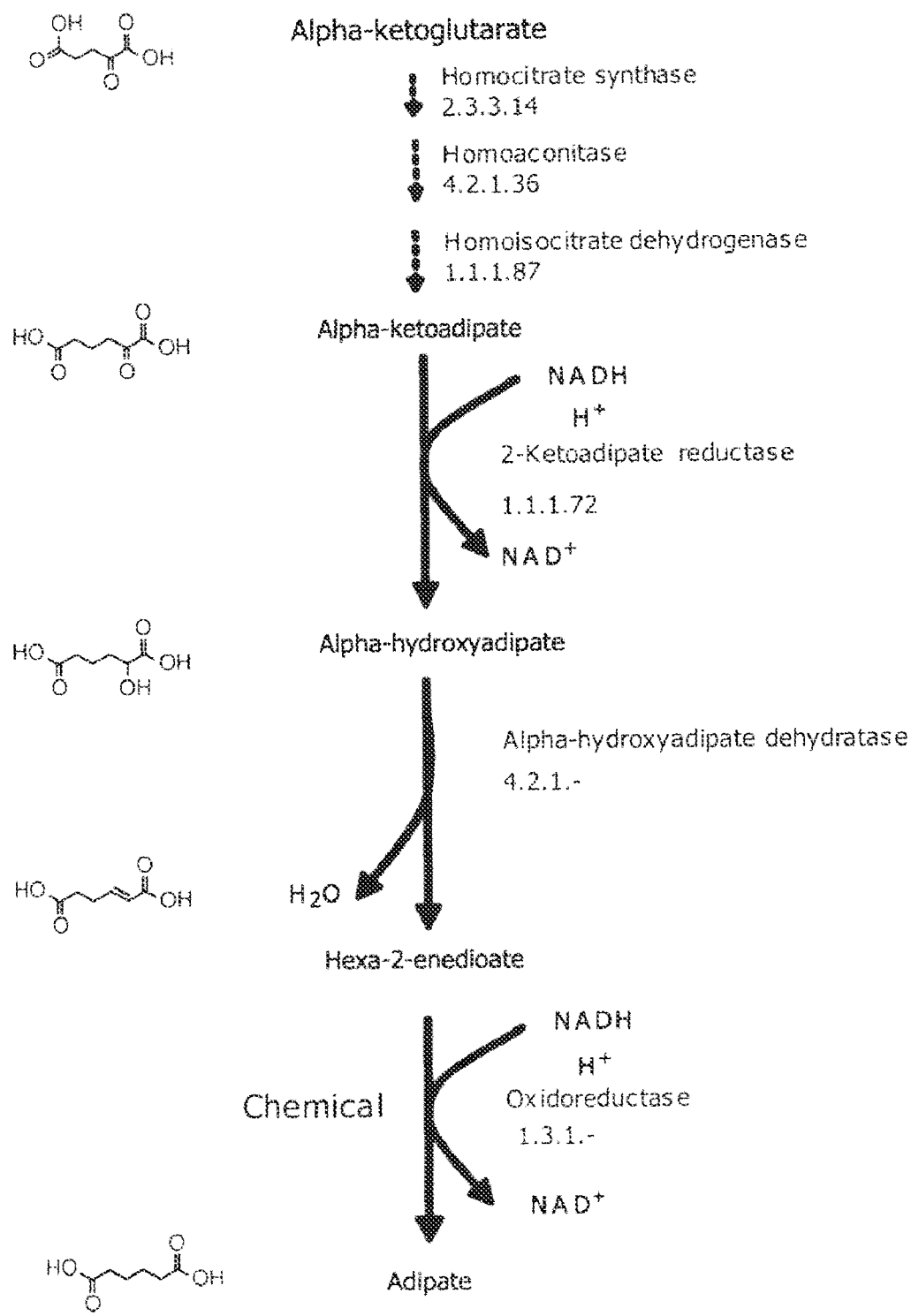
FIG. 6 shows an exemplary pathway for adipate synthesis via alpha-ketoadipate using alpha-ketoglutarate as a starting point.

An additional exemplary adipate pathway utilizes alpha-ketoadipate as a precursor (see FIG. 6 and Example VI). In yet another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising homocitrate synthase, homoaconitase, homoisocitrate dehydrogenase, 2-ketoadipate reductase, alpha-hydroxyadipate dehydratase and oxidoreductase. A further exemplary adipate pathway utilizes a lysine dedgradation pathway (see FIG. 7 and Example VII). Another embodiment of the invention provides a non-naturally occurring microbial organism having an adipate pathway comprising at least one exogenous nucleic acid encoding an adipate pathway enzyme expressed in a sufficient amount to produce adipate, the adipate pathway comprising carbon nitrogen lyase, oxidoreductase, transaminase and oxidoreductase.

Figure 9:
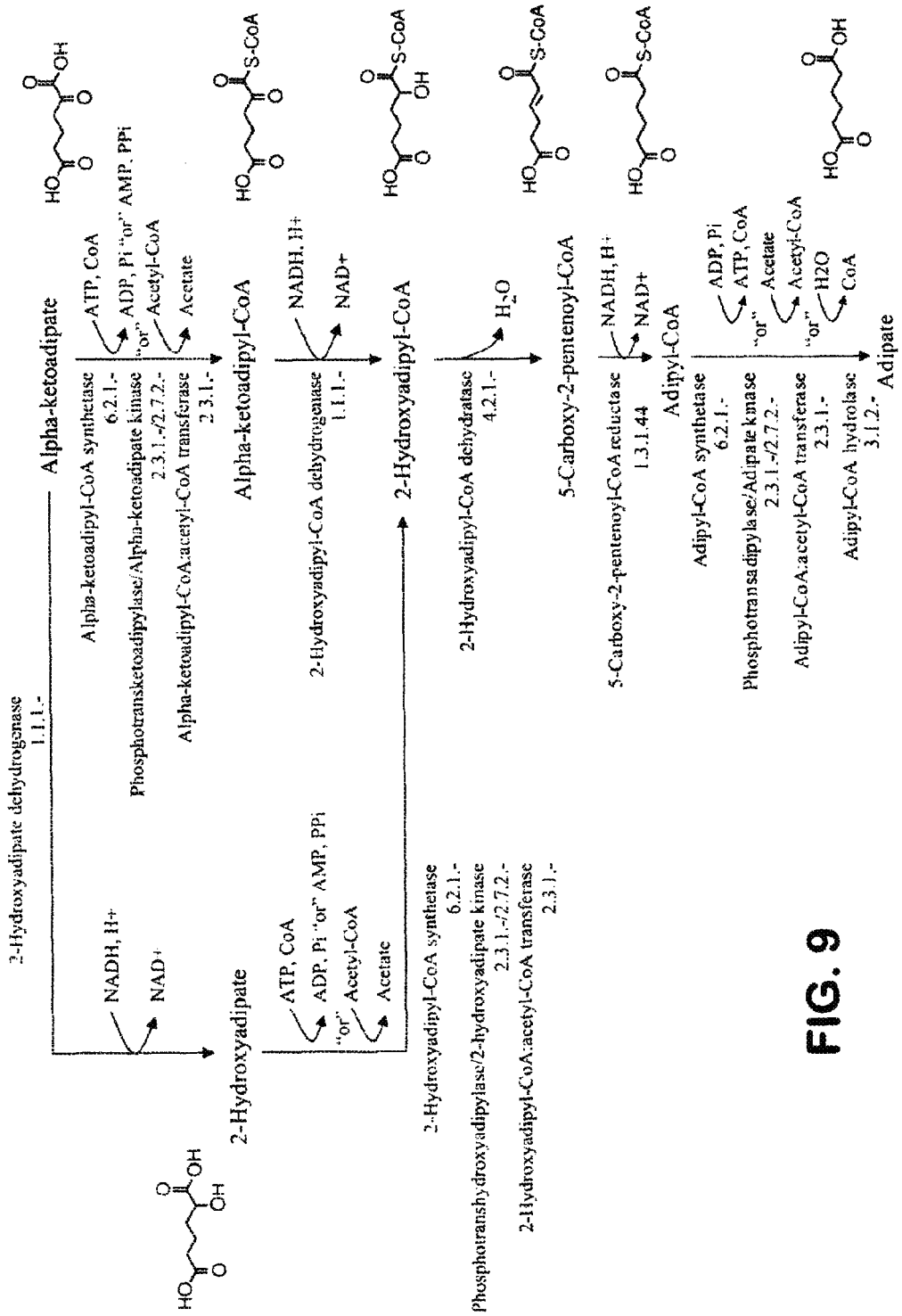
FIG. 9 shows exemplary adipate synthesis pathways using alpha-ketoadipate as a starting point.

Yet another exemplary adipate pathway utilizes alpha-ketoadipate as a precursor (see FIG. 9 and Examples X and XI). Thus, the invention additionally provides a non-naturally occurring microbial organism having an adipate pathway comprising at least one exogenous nucleic acid encoding an adipate pathway enzyme expressed in a sufficient amount to produce adipate, the adipate pathway comprising alpha-ketoadipyl-CoA synthetase, phosphotransketoadipylase/alpha-ketoadipate kinase or alpha-ketoadipyl-CoA:acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase. In still another embodiment, the invention provides a non-naturally occurring microbial organism having an adipate pathway comprising at least one exogenous nucleic acid encoding an adipate pathway enzyme expressed in a sufficient amount to produce adipate, the adipate pathway comprising 2-hydroxyadipate dehydrogenase; 2-hydroxyadipyl-CoA synthetase, phosphotranshydroxyadipylase/2-hydroxyadipate kinase or 2-hydroxyadipyl-CoA: acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA: acetyl-CoA transferase or adipyl-CoA hydrolase.

In an additional embodiment, the invention provides a non-naturally occurring microbial organism having an adipate, 6-aminocaproic acid or caprolactam pathway, wherein the non-naturally occurring microbial organism comprises at least one exogenous nucleic acid encoding a polypeptide that converts a substrate to a product, as disclosed herein. Thus, the invention provides a non-naturally occurring microbial organism containing at least one exogenous nucleic acid encoding a polypeptide, where the polypeptide is an enzyme or protein that converts the substrates and products of an adipate, 6-aminocaproic acid or caprolactam pathway, such as that shown in FIGS. 2, 3, 8 and 9.

Figure 2:
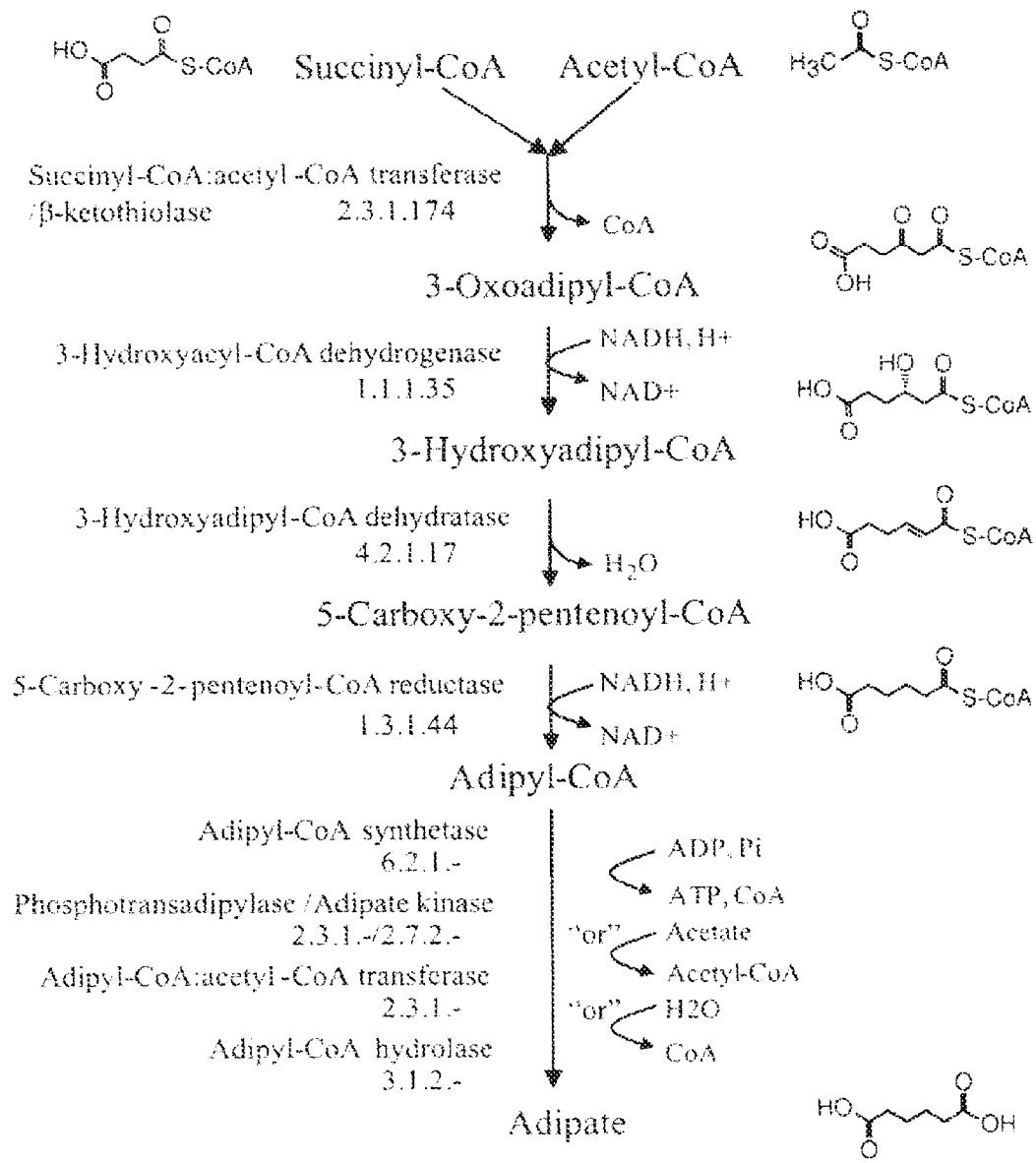
FIG. 2 shows an exemplary pathway for adipate formation via a reverse degradation pathway. Several options are provided for the final conversion of adipyl-CoA to adipate.

In one embodiment, the invention provides a non-naturally occurring microbial organism having an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-hydroxyadipyl-CoA; 3-hydroxyadipyl-CoA to 5-carboxy-2-pentenoyl-CoA; 5-carboxy-2-pentenoyl-CoA to adipyl-CoA; adipyl-CoA to adipate (see FIG. 2). In another embodiment, the invention provides a non-naturally occurring microbial organism having an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-oxoadipate; 3-oxoadipate to 3-hydroxyadipate; 3-hydroxyadipate to hexa-2-enedioate; hexa-2-enedioate to adipate (see FIG. 3).

In an additional embodiment, the invention provides a non-naturally occurring microbial organism having a 6-aminocaproic acid pathway, wherein the microbial organism contains at least one exogenous nucleic acid encoding a polypeptide that converts a substrate to a product selected from adipyl-CoA to adipate semialdehyde; and adipate semialdehyde to 6-aminocaproate (see FIG. 8). In still another embodiment, the invention provides a non-naturally occurring microbial organism having a caprolactam pathway, wherein the microbial organism contains at least one exogenous nucleic acid encoding a polypeptide that converts a substrate to a product selected from adipyl-CoA to adipate semialdehyde; adipate semialdehyde to 6-aminocaproate; and 6-aminocaproate to caprolactam.

In still another embodiment, the invention provides a non-naturally occurring microbial organism having an adipate pathway, wherein the microbial organism contains at least one exogenous nucleic acid encoding a polypeptide that converts a substrate to a product selected from alpha-ketoadipate to alpha-ketoadipyl-CoA; alpha-ketoadipyl-CoA to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (see FIG. 9). Additionally, the invention provides a non-naturally occurring microbial organism having an adipate pathway, wherein the microbial organism contains at least one exogenous nucleic acid encoding a polypeptide that converts a substrate to a product selected from alpha-ketoadipate to 2-hydroxyadipate; 2-hydroxyadipate to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (FIG. 9).

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The non-naturally occurring microbial organisms of the invention can be produced by introducing expressible nucleic acids encoding one or more of the enzymes participating in one or more adipate, 6-aminocaproic acid or caprolactam biosynthetic pathways. Depending on the host microbial organism chosen for biosynthesis, nucleic acids for some or all of a particular adipate, 6-aminocaproic acid or caprolactam biosynthetic pathway can be expressed. For example, if a chosen host is deficient in one or more enzymes for a desired biosynthetic pathway, then expressible nucleic acids for the deficient enzyme(s) are introduced into the host for subsequent exogenous expression. Alternatively, if the chosen host exhibits endogenous expression of some pathway genes, but is deficient in others, then an encoding nucleic acid is needed for the deficient enzyme(s) to achieve adipate, 6-aminocaproic acid or caprolactam biosynthesis. Thus, a non-naturally occurring microbial organism of the invention can be produced by introducing exogenous enzyme activities to obtain a desired biosynthetic pathway or a desired biosynthetic pathway can be obtained by introducing one or more exogenous enzyme activities that, together with one or more endogenous enzymes, produces a desired product such as adipate, 6-aminocaproic acid or caprolactam.

Depending on the adipate, 6-aminocaproic acid or caprolactam biosynthetic pathway constituents of a selected host microbial organism, the non-naturally occurring microbial organisms of the invention will include at least one exogenously expressed adipate, 6-aminocaproic acid or caprolactam pathway-encoding nucleic acid and up to all encoding nucleic acids for one or more adipate, 6-aminocaproic acid or caprolactam biosynthetic pathways. For example, adipate, 6-aminocaproic acid or caprolactam biosynthesis can be established in a host deficient in a pathway enzyme through exogenous expression of the corresponding encoding nucleic acid. In a host deficient in all enzymes of a adipate, 6-aminocaproic acid or caprolactam pathway, exogenous expression of all enzyme in the pathway can be included, although it is understood that all enzymes of a pathway can be expressed even if the host contains at least one of the pathway enzymes.

For example, exogenous expression of all enzymes in a pathway for production of adipate can be included in a host organism, such as succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In particular, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase. Alternatively, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and phosphotransadipylase/adipate kinase. In addition, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA:acetyl-CoA transferase. Further, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA hydrolase.

In the case of a 6-aminocaproic acid producing microbial organism, exogenous expression of all enzymes in a pathway for production of 6-aminocaproic acid can be included in a host organism, such as CoA-dependent aldehyde dehydrogenase and transaminase or CoA-dependent aldehyde dehydrogenase and 6-aminocaproate dehydrogenase. For a caprolactam producing microbial organism, exogenous expression of all enzymes in a pathway for production of caprolactam can be included in a host organism, such as CoA-dependent aldehyde dehydrogenase, transaminase or 6-aminocaproate dehydrogenase, and amidohydrolase.

Given the teachings and guidance provided herein, those skilled in the art will understand that the number of encoding nucleic acids to introduce in an expressible form will, at least, parallel the adipate, 6-aminocaproic acid or caprolactam pathway deficiencies of the selected host microbial organism. Therefore, a non-naturally occurring microbial organism of the invention can have one, two, three, four, or five, up to all nucleic acids encoding the above enzymes constituting a adipate, 6-aminocaproic acid or caprolactam biosynthetic pathway. In some embodiments, the non-naturally occurring microbial organisms also can include other genetic modifications that facilitate or optimize adipate, 6-aminocaproic acid or caprolactam biosynthesis or that confer other useful functions onto the host microbial organism. One such other functionality can include, for example, augmentation of the synthesis of one or more of the adipate, 6-aminocaproic acid or caprolactam pathway precursors such as succinyl-CoA and/or acetyl-CoA in the case of adipate synthesis, or adipyl-CoA in the case of 6-aminocaproic acid or caprolactam synthesis, including the adipate pathway enzymes disclosed herein.

In some embodiments, a non-naturally occurring microbial organism of the invention is generated from a host that contains the enzymatic capability to synthesize adipate, 6-aminocaproic acid or caprolactam. In this specific embodiment it can be useful to increase the synthesis or accumulation of an adipate, 6-aminocaproic acid or caprolactam pathway product to, for example, drive adipate, 6-aminocaproic acid or caprolactam pathway reactions toward adipate, 6-aminocaproic acid or caprolactam production. Increased synthesis or accumulation can be accomplished by, for example, overexpression of nucleic acids encoding one or more of the above-described adipate, 6-aminocaproic acid or caprolactam pathway enzymes. Over expression of the adipate, 6-aminocaproic acid or caprolactam pathway enzyme or enzymes can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing adipate, 6-aminocaproic acid or caprolactam, through overexpression of one, two, three, four, five, that is, up to all nucleic acids encoding adipate, 6-aminocaproic acid or caprolactam biosynthetic pathway enzymes. In addition, a non-naturally occurring organism can be generated by mutagenesis of an endogenous gene that results in an increase in activity of an enzyme in the adipate, 6-aminocaproic acid or caprolactam biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an adipate, 6-aminocaproic acid or caprolactam biosynthetic pathway onto the microbial organism. Alternatively, encoding nucleic acids can be introduced to produce an intermediate microbial organism having the biosynthetic capability to catalyze some of the required reactions to confer adipate, 6-aminocaproic acid or caprolactam biosynthetic capability. For example, a non-naturally occurring microbial organism having an adipate, 6-aminocaproic acid or caprolactam biosynthetic pathway can comprise at least two exogenous nucleic acids encoding desired enzymes. In the case of adipate production, the at least two exogenous nucleic acids can encode the enzymes such as the combination of succinyl-CoA:acetyl-CoA acyl transferase and 3-hydroxyacyl-CoA dehydrogenase, or succinyl-CoA:acetyl-CoA acyl transferase and 3-hydroxyadipyl-CoA dehydratase, or 3-hydroxyadipyl-CoA and 5-carboxy-2-pentenoyl-CoA reductase, or 3-hydroxyacyl-CoA and adipyl-CoA synthetase, and the like. In the case of caprolactam production, the at least two exogenous nucleic acids can encode the enzymes such as the combination of CoA-dependent aldehyde dehydrogenase and transaminase, or CoA-dependent aldehyde dehydrogenase and amidohydrolase, or transaminase and amidohydrolase. Thus, it is understood that any combination of two or more enzymes of a biosynthetic pathway can be included in a non-naturally occurring microbial organism of the invention.

Similarly, it is understood that any combination of three or more enzymes of a biosynthetic pathway can be included in a non-naturally occurring microbial organism of the invention, for example, in the case of adipate production, the combination of enzymes succinyl-CoA:acetyl-CoA acyl transferase, 3-hydroxyacyl-CoA dehydrogenase, and 3-hydroxyadipyl-CoA dehydratase; or succinyl-CoA:acetyl-CoA acyl transferase, 3-hydroxyacyl-CoA dehydrogenase and 5-carboxy-2-pentenoyl-CoA reductase; or succinyl-CoA:acetyl-CoA acyl transferase, 3-hydroxyacyl-CoA dehydrogenase and adipyl-CoA synthetase; or 3-hydroxyacyl-CoA dehydrogenase, 3-hydroxyadipyl-CoA dehydratase and adipyl-CoA:acetyl-CoA transferase, and so forth, as desired, so long as the combination of enzymes of the desired biosynthetic pathway results in production of the corresponding desired product. Similarly, any combination of four or more enzymes of a biosynthetic pathway as disclosed herein can be included in a non-naturally occurring microbial organism of the invention, as desired, so long as the combination of enzymes of the desired biosynthetic pathway results in production of the corresponding desired product.

In addition to the biosynthesis of adipate, 6-aminocaproic acid or caprolactam as described herein, the non-naturally occurring microbial organisms and methods of the invention also can be utilized in various combinations with each other and with other microbial organisms and methods well known in the art to achieve product biosynthesis by other routes. For example, one alternative to produce adipate, 6-aminocaproic acid or caprolactam other than use of the adipate, 6-aminocaproic acid or caprolactam producers is through addition of another microbial organism capable of converting an adipate, 6-aminocaproic acid or caprolactam pathway intermediate to adipate, 6-aminocaproic acid or caprolactam. One such procedure includes, for example, the fermentation of a microbial organism that produces an adipate, 6-aminocaproic acid or caprolactam pathway intermediate. The adipate, 6-aminocaproic acid or caprolactam pathway intermediate can then be used as a substrate for a second microbial organism that converts the adipate, 6-aminocaproic acid or caprolactam pathway intermediate to adipate, 6-aminocaproic acid or caprolactam. The adipate, 6-aminocaproic acid or caprolactam pathway intermediate can be added directly to another culture of the second organism or the original culture of the adipate, 6-aminocaproic acid or caprolactam pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, adipate, 6-aminocaproic acid or caprolactam. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of adipate, 6-aminocaproic acid or caprolactam can be accomplished by constructing a microbial organism that contains biosynthetic pathways for conversion of one pathway intermediate to another pathway intermediate or the product. Alternatively, adipate, 6-aminocaproic acid or caprolactam also can be biosynthetically produced from microbial organisms through co-culture or co-fermentation using two organisms in the same vessel, where the first microbial organism produces a adipate, 6-aminocaproic acid or caprolactam intermediate and the second microbial organism converts the intermediate to adipate, 6-aminocaproic acid or caprolactam.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce adipate, 6-aminocaproic acid or caprolactam.

Sources of encoding nucleic acids for an adipate, 6-aminocaproic acid or caprolactam pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *Pseudomonas knackmussii*, *Pseudomonas putida*, *Pseudomonas fluorescens*, *Klebsiella pneumoniae*, *Serratia proteamaculans*, *Streptomyces* sp. 2065, *Pseudomonas aeruginosa*, *Ralstonia eutropha*, *Clostridium acetobutylicum*, *Euglena gracilis*, *Treponema denticola*, *Clostridium kluyveri*, *Homo sapiens*, *Rattus norvegicus*, *Acinetobacter* sp. ADP1, *Streptomyces coelicolor*, *Eubacterium barkeri*, *Peptostreptococcus asaccharolyticus*, *Clostridium botulinum*, *Clostridium tyrobutyricum*, *Clostridium thermoaceticum* (*Moorella thermoaceticum*), *Acinetobacter calcoaceticus*, *Mus musculus*, *Sus scrofa*, *Flavobacterium* sp, *Arthrobacter aurescens*, *Penicillium chrysogenum*, *Aspergillus niger*, *Aspergillus nidulans*, *Bacillus subtilis*, *Saccharomyces cerevisiae*, *Zymomonas mobilis*, *Mannheimia succiniciproducens*, *Clostridium ljungdahlii*, *Clostridium carboxydivorans*, *Geobacillus stearothermophilus*, *Agrobacterium tumefaciens*, *Achromobacter denitrificans*, *Arabidopsis thaliana*, *Haemophilus influenzae*, *Acidaminococcus fermentans*, *Clostridium* sp. M62/1, *Fusobacterium nucleatum*, as well as other exemplary species disclosed herein or available as source organisms for corresponding genes (see Examples). However, with the complete genome sequence available for now more than 550 species (with more than half of these available on public databases such as the NCBI), including 395 microorganism genomes and a variety of yeast, fungi, plant, and mammalian genomes, the identification of genes encoding the requisite adipate, 6-aminocaproic acid or caprolactam biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of adipate, 6-aminocaproic acid or caprolactam described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative adipate, 6-aminocaproic acid or caprolactam biosynthetic pathway exists in an unrelated species, adipate, 6-aminocaproic acid or caprolactam biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize adipate, 6-aminocaproic acid or caprolactam.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. For example, *E. coli* is a particularly useful host organisms since it is a well characterized microbial organism suitable for genetic engineering. Other particularly useful host organisms include yeast such as *Saccharomyces cerevisiae.*

Methods for constructing and testing the expression levels of a non-naturally occurring adipate-, 6-aminocaproic acid- or caprolactam-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of adipate, 6-aminocaproic acid or caprolactam can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more adipate, 6-aminocaproic acid or caprolactam biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides methods for producing a desired product such as adipate, 6-aminocaproic acid or caprolactam. In one embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In another embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising succinyl-CoA:acetyl-CoA acyl transferase, 3-oxoadipyl-CoA transferase, 3-oxoadipate reductase, 3-hydroxyadipate dehydratase, and 2-enoate reductase.

In yet another embodiment, the invention provides a method for producing 6-aminocaproic acid, comprising culturing a non-naturally occurring microbial organism having a 6-aminocaproic acid pathway, the pathway comprising at least one exogenous nucleic acid encoding a 6-aminocaproic acid pathway enzyme expressed in a sufficient amount to produce 6-aminocaproic acid, under conditions and for a sufficient period of time to produce 6-aminocaproic acid, the 6-aminocaproic acid pathway comprising CoA-dependent aldehyde dehydrogenase and transaminase or 6-aminocaproate dehydrogenase. In a further embodiment, the invention provides a method for producing caprolactam, comprising culturing a non-naturally occurring microbial organism having a caprolactam pathway, the pathway comprising at least one exogenous nucleic acid encoding a caprolactam pathway enzyme expressed in a sufficient amount to produce caprolactam, under conditions and for a sufficient period of time to produce caprolactam, the caprolactam pathway comprising CoA-dependent aldehyde dehydrogenase, transaminase or 6-aminocaproate dehydrogenase, and amidohydrolase.

The invention additionally provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising alpha-ketoadipyl-CoA synthetase, phosphotransketoadipylase/alpha-ketoadipate kinase or alpha-ketoadipyl-CoA: acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

In still another embodiment, the invention provides a method for producing adipate, comprising culturing a non-naturally occurring microbial organism having an adipate pathway, the pathway comprising at least one exogenous nucleic acid encoding an adipate pathway enzyme expressed in a sufficient amount to produce adipate, under conditions and for a sufficient period of time to produce adipate, the adipate pathway comprising 2-hydroxyadipate dehydrogenase; 2-hydroxyadipyl-CoA synthetase, phosphotranshydroxyadipylase/2-hydroxyadipate kinase or 2-hydroxyadipyl-CoA:acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

Suitable purification and/or assays to test for the production of adipate, 6-aminocaproic acid or caprolactam can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme activities from the exogenous DNA sequences can also be assayed using methods well known in the art.

The adipate, 6-aminocaproic acid or caprolactam can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the adipate, 6-aminocaproic acid or caprolactam producers can be cultured for the biosynthetic production of adipate, 6-aminocaproic acid or caprolactam.

For the production of adipate, 6-aminocaproic acid or caprolactam, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of adipate, 6-aminocaproic acid or caprolactam.

In addition to renewable feedstocks such as those exemplified above, the adipate, 6-aminocaproic acid or caprolactam microbial organisms of the invention also can be modified for growth on syngas as its source of carbon. In this specific embodiment, one or more proteins or enzymes are expressed in the adipate, 6-aminocaproic acid or caprolactam producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis, pp.* 3-60 Chapman and Hall, New York, (1994)). This can be summarized by the following equation:

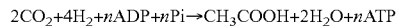

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided herein for introducing a sufficient number of encoding nucleic acids to generate an adipate, 6-aminocaproic acid or caprolactam pathway, those skilled in the art will understand that the same engineering design also can be performed with respect to introducing at least the nucleic acids encoding the Wood-Ljungdahl enzymes absent in the host organism. Therefore, introduction of one or more encoding nucleic acids into the microbial organisms of the invention such that the modified organism contains the complete Wood-Ljungdahl pathway will confer syngas utilization ability.

Given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, adipate, 6-aminocaproic acid or caprolactam and any of the intermediate metabolites in the adipate, 6-aminocaproic acid or caprolactam pathway. All that is required is to engineer in one or more of the required enzyme activities to achieve biosynthesis of the desired compound or intermediate including, for example, inclusion of some or all of the adipate, 6-aminocaproic acid or caprolactam biosynthetic pathways. Accordingly, the invention provides a non-naturally occurring microbial organism that produces and/or secretes adipate, 6-aminocaproic acid or caprolactam when grown on a carbohydrate and produces and/or secretes any of the intermediate metabolites shown in the adipate, 6-aminocaproic acid or caprolactam pathway when grown on a carbohydrate. For example, the adipate producing microbial organisms of the invention can initiate synthesis from an intermediate, for example, 3-oxoadipyl-CoA, 3-hydroxyadipyl-CoA, 5-carboxy-2-pentenoyl-CoA, or adipyl-CoA (see FIG. 2), as desired. In addition, an adipate producing microbial organism can initiate synthesis from an intermediate, for example, 3-oxoadipyl-CoA, 3-oxoadipate, 3-hydroxyadipate, or hexa-2-enedioate (see FIG. 3). The 6-aminocaproic acid producing microbial organism of the invention can initiate synthesis from an intermediate, for example, adipate semialdehyde (see FIG. 8). The caprolactam producing microbial organism of the invention can initiate synthesis from an intermediate, for example, adipate semialdehyde or 6-aminocaproic acid (see FIG. 8), as desired.

The non-naturally occurring microbial organisms of the invention are constructed using methods well known in the art as exemplified herein to exogenously express at least one nucleic acid encoding an adipate, 6-aminocaproic acid or caprolactam pathway enzyme in sufficient amounts to produce adipate, 6-aminocaproic acid or caprolactam. It is understood that the microbial organisms of the invention are cultured under conditions sufficient to produce adipate, 6-aminocaproic acid or caprolactam. Following the teachings and guidance provided herein, the non-naturally occurring microbial organisms of the invention can achieve biosynthesis of adipate, 6-aminocaproic acid or caprolactam resulting in intracellular concentrations between about 0.1-200 mM or more. Generally, the intracellular concentration of adipate, 6-aminocaproic acid or caprolactam is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the adipate, 6-aminocaproic acid or caprolactam producers can synthesize adipate, 6-aminocaproic acid or caprolactam at intracellular concentrations of 5-10 mM or more as well as all other concentrations exemplified herein. It is understood that, even though the above description refers to intracellular concentrations, adipate, 6-aminocaproic acid or caprolactam producing microbial organisms can produce adipate, 6-aminocaproic acid or caprolactam intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of adipate, 6-aminocaproic acid or caprolactam includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of adipate, 6-aminocaproic acid or caprolactam. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of adipate, 6-aminocaproic acid or caprolactam. Generally, and as with non-continuous culture procedures, the continuous and/or near-continuous production of adipate, 6-aminocaproic acid or caprolactam will include culturing a non-naturally occurring adipate, 6-aminocaproic acid or caprolactam producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods.

It is further understood that the time of culturing the microbial organism of the invention is for a sufficient period of time to produce a sufficient amount of product for a desired purpose.

Fermentation procedures are well known in the art. Briefly, fermentation for the biosynthetic production of adipate, 6-aminocaproic acid or caprolactam can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the adipate, 6-aminocaproic acid or caprolactam producers of the invention for continuous production of substantial quantities of adipate, 6-aminocaproic acid or caprolactam, the adipate, 6-aminocaproic acid or caprolactam producers also can be, for example, simultaneously subjected to chemical synthesis procedures to convert the product to other compounds or the product can be separated from the fermentation culture and sequentially subjected to chemical conversion to convert the product to other compounds, if desired. As described herein, an intermediate in the adipate pathway utilizing 3-oxoadipate, hexa-2-enedioate, can be converted to adipate, for example, by chemical hydrogenation over a platinum catalyst (see Example III).

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate, 6-aminocaproic acid or caprolactam.

One computational method for identifying and designing metabolic alterations favoring biosynthesis of a desired product is the OptKnock computational framework, Burgard et al., *Biotechnol. Bioeng.* 84:647-657 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

EXAMPLE I

Reverse Adipate Degradation Pathway

This example describes an exemplary adipate synthesis pathway via a reverse adipate degradation pathway.

Organisms such as *Penicillium chrysogenum* have the ability to naturally degrade adipate (Thykaer et al., *Metab. Eng.* 4:151-158. (2002)). The mechanism is similar to the oxidation of fatty acids (see FIG. 1). The first step in adipate degradation is an ATP-dependent reaction that activates adipate with CoA. The second reaction is catalyzed by a dehydrogenase that forms 5-carboxy-2-pentenoyl-CoA from adipyl-CoA. During peroxisomal adipate degradation, the dehydrogenase enzyme contains FAD, which accepts the electrons and then transfers them directly to oxygen. A catalase enzyme dissipates the $H_2O_2$ formed by the reduction of oxygen. In mitochondrial fatty acid oxidation, the FAD from the dehydrogenase transfers electrons directly to the electron transport chain. A multi-functional fatty acid oxidation protein in eukaryotes such as *S. cerevisiae* and *P. chrysogenum* carries out the following hydratase and dehydrogenase steps. The final step is an acyl transferase that splits 3-oxoadipyl CoA into acetyl-CoA and succinyl-CoA.

A highly efficient pathway for the production of adipate is achieved through genetically altering a microorganism such that similar enzymatic reactions are employed for adipate synthesis from succinyl-CoA and acetyl-CoA (see FIG. 2). Successful implementation of this entails expressing the appropriate genes, tailoring their expression, and altering culture conditions so that high acetyl-CoA, succinyl-CoA, and/or redox (for example, NADH/NAD+) ratios will drive the metabolic flux through this pathway in the direction of adipate synthesis rather than degradation. Strong parallels to butyrate formation in *Clostridia* (Kanehisa and Goto, *Nucl. Acids Res.* 28:27-30 (2000)) support that each step in the adipate synthesis pathway is thermodynamically feasible with reaction directionality governed by the concentrations of the participating metabolites. The final step, which forms adipate from adipyl-CoA, can take place either via a synthetase, phosphotransadipylase/kinase, transferase, or hydrolase mechanism.

The maximum theoretical yields of adipate using this pathway were calculated both in the presence and absence of an external electron acceptor such as oxygen. These calculations show that the pathway can efficiently transform glucose into adipate and $CO_2$ under anaerobic conditions with a 92% molar yield (Table I). The production of adipate using this pathway does not require the uptake of oxygen as NAD+ can be regenerated in the two hydrogenase steps that form 3-hydroxyadipyl-CoA and adipyl-CoA (see FIG. 2). Further, the pathway is favorable energetically as up to 1.55 moles of ATP are formed per mole of glucose consumed at the maximum theoretical yield of adipate assuming either a synthetase, phosphotransadipylase/kinase, or transferase mechanism for the final conversion step. The ATP yield can be further improved to 2.47 moles of ATP produced per mole of glucose if phosphoenolpyruvate carboxykinase (PPCK) is assumed to function in the ATP-generating direction towards oxaloacetate formation. Maximum ATP yield calculations were then performed assuming that the adipyl-CoA to adipate transformation is a hydrolysis step. This reduces the maximum ATP yields at maximum adipate production to 0.85 and 1.77 mole ATP per mole glucose consumed if PPCK is assumed irreversible and reversible, respectively. Nevertheless, these ATP yields are sufficient for cell growth, maintenance, and production.

TABLE 1

The maximum theoretical yields of adipate and the associated ATP yields per mole of glucose using the reverse degradation pathway assuming the final step in the pathway is a synthetase, phosphotransadipylase/kinase, or transferase.

|  | Aerobic | Anaerobic |
| --- | --- | --- |
| Adipate Yield | 0.92 | 0.92 |
| Max ATP yield @ max adipate yield | 1.55 | 1.55 |
| Max ATP yield @ max adipate yield PPCK assumed | 2.47 | 2.47 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) are expressed in a suitable host microorganism. In addition, the microorganisms can have endogenous gene(s) functionally deleted. These modifications allow the production of adipate using renewable feedstock.

Below is described a number of biochemically characterized candidate genes that encode enzymes that catalyze each step of the reverse adipate degradation pathway in a production host. Although described using *E. coli* as a host organism to engineer the pathway, essentially any suitable host organism can be used. Specifically listed are genes that are native to E. coli as well as genes in other organisms that can be applied to catalyze the appropriate transformations when properly cloned and expressed.

Referring to FIG. 2, step 1 involves succinyl CoA:acetyl CoA acyl transferase (β-ketothiolase). The first step in the pathway combines acetyl-CoA and succinyl-CoA to form 3-oxoadipyl-CoA. The gene products encoded by pcaF in *Pseudomonas* strain B13 (Kaschabek et al., *J. Bacteriol.* 184: 207-215 (2002)), phaD in *Pseudomonas putida* U (Olivera et al., *Proc. Natl. Acad. Sci. USA* 95:6419-6424 (1998)), paaE in *Pseudomonas fluorescens* ST (Di Gennaro et al., *Arch. Microbiol.* 188:117-125 (2007)), and paaJ from *E. coli* (Nogales et al., *Microbiol.* 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the first step in adipate synthesis shown in FIG. 2. For example, the ketothiolase phaA from *R. eutropha* combines two molecules of acetyl-CoA to form acetoacetyl-CoA (Sato et al., *J. Biosci. Bioengineer.* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180: 1979-1987 (1998)) in *R. eutropha*. The protein sequences for the above-mentioned gene products are well known in the art and can be accessed in the public databases such as GenBank using the following accession numbers.

| Gene name | GenBank Accession # | Organism |
| --- | --- | --- |
| paaJ | NP_415915.1 | *Escherichia coli* |
| pcaF | AAL02407 | *Pseudomonas knackmussii* (B13) |
| phaD | AAC24332.1 | *Pseudomonas putida* |
| paaE | ABF82237.1 | *Pseudomonas fluorescens* |

These exemplary sequences can be used to identify homologue proteins in GenBank or other databases through sequence similarity searches (for example, BLASTp). The resulting homologue proteins and their corresponding gene sequences provide additional exogenous DNA sequences for transformation into *E. coli* or other suitable host microorganisms to generate production hosts.

For example, orthologs of paaJ from *Escherichia coli* K12 can be found using the following GenBank accession numbers:

| | |
| --- | --- |
| YP_001335140.1 | *Klebsiella pneumoniae* |
| YP_001479310.1 | *Serratia proteamaculans* |
| AAC24332.1 | *Pseudomonas putida* |

Example orthologs of pcaF from *Pseudomonas knackmussii* can be found using the following GenBank accession numbers:

| | |
| --- | --- |
| AAD22035.1 | *Streptomyces* sp. 2065 |
| AAN67000.1 | *Pseudomonas putida* |
| ABJ15177.1 | *Pseudomonas aeruginosa* |

Additional native candidate genes for the ketothiolase step include atoB, which can catalyze the reversible condensation of 2 acetyl-CoA molecules (Sato et al., *J. Biosci. Bioengineer.* 103:38-44 (2007)), and its homolog yqeF. Non-native gene candidates include phaA (Sato et al., supra, 2007) and bktB (Slater et al., *J. Bacteriol.* 180:1979-1987 (1998)) from *R. eutropha*, and the two ketothiolases, thiA and thiB, from *Clostridium acetobutylicum* (Winzer et al., *J. Mol. Microbiol. Biotechnol.* 2:531-541 (2000)). The protein sequences for each of these exemplary gene products can be found using the following GenBank accession numbers:

| | | |
| --- | --- | --- |
| atoB | NP_416728.1 | *Escherichia coli* |
| yqeF | NP_417321.2 | *Escherichia coli* |
| phaA | YP_725941 | *Ralstonia eutropha* |
| bktB | AAC38322.1 | *Ralstonia eutropha* |
| thiA | NP_349476.1 | *Clostridium acetobutylicum* |
| thiB | NP_149242.1 | *Clostridium acetobutylicum* |

Referring to FIG. 2, step 2 involves 3-hydroxyacyl-CoA dehydrogenase. The second step in the pathway involves the reduction of 3-oxoadipyl-CoA to 3-hydroxyadipyl-CoA. The gene products encoded by phaC in *Pseudomonas putida* U (Olivera et al., *Proc. Natl. Acad. Sci. USA* 95:6419-6424 (1998)) and paaC in *Pseudomonas fluorescens* ST (Di Gennaro et al., *Arch. Microbiol.* 188:117-125 (2007)) catalyze the reverse reaction, that is, the oxidation of 3-hydroxyadipyl-CoA to form 3-oxoadipyl-CoA, during the catabolism of phenylacetate or styrene. The reactions catalyzed by such dehydrogenases are reversible and accordingly these genes represent candidates to carry out the second step of adipate synthesis as shown in FIG. 2. A similar transformation is also carried out by the gene product of hbd in *Clostridium acetobutylicum* (Atsumi et al., *Metab. Eng.* (epub Sep. 14, 2007); Boynton et al., *J. Bacteriol.* 178:3015-3024 (1996)). This enzyme converts acetoacetyl-CoA to 3-hydroxybutyryl-CoA. Lastly, given the proximity in *E. coli* of paaH to other genes in the phenylacetate degradation operon (Nogales et al., *Microbiol.* 153:357-365 (2007)) and the fact that paaH mutants cannot grow on phenylacetate (Ismail et al., *Eur. J. Biochem.* 270:3047-3054 (2003)), it is expected that the *E. coli* paaH gene encodes a 3-hydroxyacyl-CoA dehydrogenase. The protein sequences for each of these exemplary gene products can be found using the following GenBank accession numbers:

| | | |
| --- | --- | --- |
| paaH | NP_415913.1 | *Escherichia coli* |
| phaC | NP_745425.1 | *Pseudomonas putida* |
| paaC | ABF82235.1 | *Pseudomonas fluorescens* |
| hbd | NP_349314.1 | *Clostridium acetobutylicum* |

Referring to FIG. 2, step 3 involves 3-hydroxyadipyl-CoA dehydratase. The gene product of crt from *C. acetobutylicum* catalyzes the dehydration of 3-hydroxybutyryl-CoA to crotonyl-CoA (see FIG. 2) (Atsumi et al., supra, 2007; Boynton et al., *J. Bacteriol.* 178:3015-3024 (1996)). Homologs of this gene are strong candidates for carrying out the third step in the adipate synthesis pathway exemplified in FIG. 2. In addition, genes known to catalyze the hydroxylation of double bonds in enoyl-CoA compounds represent additional candidates given the reversibility of such enzymatic transformations. For example, the enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)) and thus represent additional candidates for incorporation into *E. coli*. The deletion of these genes precludes phenylacetate degradation in *P. putida*. The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Biotechnol. Bioeng.* 86:681-686 (2004); Park and Lee, *Appl. Biochem. Biotechnol.* 113-116:335-346 (2004)), and paaG (Ismail et al., supra, 2003; Park and Lee, supra, 2004; Park and Lee, supra, 2004). The protein sequences for each of these exemplary gene products can be found using the following GenBank accession numbers:

| maoC | NP_415905.1 | *Escherichia coli* |
|------|-------------|--------------------|
| paaF | NP_415911.1 | *Escherichia coli* |
| paaG | NP_415912.1 | *Escherichia coli* |
| crt  | NP_349318.1 | *Clostridium acetobutylicum* |
| paaA | NP_745427.1 | *Pseudomonas putida* |
| paaB | NP_745426.1 | *Pseudomonas putida* |
| phaA | ABF82233.1  | *Pseudomonas fluorescens* |
| phaB | ABF82234.1  | *Pseudomonas fluorescens* |

Alternatively, β-oxidation genes are candidates for the first three steps in adipate synthesis. Candidate genes for the proposed adipate synthesis pathway also include the native fatty acid oxidation genes of *E. coli* and their homologs in other organisms. The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al., *Biochem.* 30:6788-6795 (1991); Yang et al., *J. Biol. Chem.* 265:10424-10429 (1990); Yang et al., *J. Biol. Chem.* 266:16255 (1991); Nakahigashi and Inokuchi, *Nucl. Acids Res.* 18: 4937 (1990)). These activities are mechanistically similar to the first three transformations shown in FIG. 2. The fadI and fadJ genes encode similar functions and are naturally expressed only anaerobically (Campbell et al., *Mol. Microbiol.* 47:793-805 (2003)). These gene products naturally operate to degrade short, medium, and long chain fatty-acyl-CoA compounds to acetyl-CoA, rather than to convert succinyl-CoA and acetyl-CoA into 5-carboxy-2-pentenoyl-CoA as proposed in FIG. 2. However, it is well known that the ketoacyl-CoA thiolase, 3-hydroxyacyl-CoA dehydrogenase, and enoyl-CoA hydratase enzymes catalyze reversible transformations. Furthermore, directed evolution and related approaches can be applied to tailor the substrate specificities of the native β-oxidation machinery of *E. coli*. Thus these enzymes or homologues thereof can be applied for adipate production. If the native genes operate to degrade adipate or its precursors in vivo, the appropriate genetic modifications are made to attenuate or eliminate these functions. However, it may not be necessary since a method for producing poly[(R)-3-hydroxybutyrate] in *E. coli* that involves activating fadB, by knocking out a negative regulator, fadR, and co-expressing a non-native ketothiolase, phaA from Ralstonia eutropha, has been described (Sato et al., *J. Biosci. Bioeng.* 103:38-44 (2007)). This work clearly demonstrated that a β-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors. The protein sequences for each of these exemplary gene products can be found using the following GenBank accession numbers:

| fadA | YP_026272.1  | *Escherichia coli* |
|------|--------------|--------------------|
| fadB | NP_418288.1  | *Escherichia coli* |
| fadI | NP_416844.1  | *Escherichia coli* |
| fadJ | NP_416843.1  | *Escherichia coli* |
| fadR | NP_415705.1  | *Escherichia coli* |

Referring to FIG. 2, step 4 involves 5-carboxy-2-pentenoyl-CoA reductase. Whereas the ketothiolase, dehydrogenase, and enoyl-CoA hydratase steps are generally reversible, the enoyl-CoA reductase step is almost always oxidative and irreversible under physiological conditions (Hoffmeister et al., *J. Biol. Chem.* 280:4329-4338 (2005)). FadE catalyzes this likely irreversible transformation in *E. coli* (Campbell and Cronan, *J. Bacteriol.* 184:3759-3764 (2002)). The pathway requires an enzyme that can reduce a 2-enoyl-CoA intermediate, not one such as FadE that will only oxidize an acyl-CoA to a 2-enoyl-CoA compound. Furthermore, although it has been suggested that *E. coli* naturally possesses enzymes for enoyl-CoA reduction (Mizugaki et al., *J. Biochem.* 92:1649-1654 (1982); Nishimaki et al., *J. Biochem.* 95:1315-1321 (1984)), no *E. coli* gene possessing this function has been biochemically characterized.

One candidate gene for the enoyl-CoA reductase step is the gene product of bcd from *C. acetobutylicum* (Atsumi et al., supra, 2007; Boynton et al., *J. Bacteriol.* 178:3015-3024 (1996)), which naturally catalyzes the reduction of crotonyl-CoA to butyryl-CoA, a reaction similar in mechanism to the desired reduction of 5-carboxy-2-pentenoyl-CoA to adipyl-CoA in the adipate synthesis pathway. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli*, resulting in an active enzyme (Hoffmeister et al., supra, 2005). This approach is well known to those skilled in the art of expressing eukarytotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin, *FEBS Lett.* 581:1561-1566 (2007)). The protein sequences for each of these exemplary gene products can be found using the following GenBank accession numbers:

| bcd     | NP_349317.1 | *Clostridium acetobutylicum* |
|---------|-------------|------------------------------|
| etfA    | NP_349315.1 | *Clostridium acetobutylicum* |
| etfB    | NP_349316.1 | *Clostridium acetobutylicum* |
| TER     | Q5EU90.1    | *Euglena gracilis*           |
| TDE0597 | NP_971211.1 | *Treponema denticola*        |

Referring to FIG. 2, step 5 involves adipyl-CoA synthetase (also referred to as adipate-CoA ligase), phosphotransadipylase/adipate kinase, adipyl-CoA:acetyl-CoA transferase, or adipyl-CoA hydrolase. From an energetic standpoint, it is desirable for the final step in the adipate synthesis pathway to be catalyzed by an enzyme or enzyme pair that can conserve the ATP equivalent stored in the thioester bond of adipyl-CoA. The product of the sucC and sucD genes of *E. coli*, or homologs thereof, can potentially catalyze the final transformation shown in FIG. 2 should they exhibit activity on adipyl-CoA. The sucCD genes naturally form a succinyl-CoA synthetase complex that catalyzes the formation of succinyl-CoA from succinate with the concaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA. An enzyme exhibiting adipyl-CoA ligase activity can equivalently carry out the ATP-generating production of adipate from adipyl-CoA, here using AMP and PPi as cofactors, when operating in the opposite physiological direction as depicted in FIG. 1. Exemplary CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395, 147-155 (2005); Wang et al., *Biochem. Biophy. Res. Commun.* 360:453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178:4122-4130 (1996)). The protein sequences for each of these exemplary gene products can be found using the following GenBank accession numbers:

| sucC | NP_415256.1 | *Escherichia coli* |
| sucD | AAC73823.1 | *Escherichia coli* |

Another option, using phosphotransadipylase/adipate kinase, is catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)), or homologs thereof. The ptb gene encodes an enzyme that can convert butyryl-CoA into butyryl-phosphate, which is then converted to butyrate via either of the buk gene products with the concomitant generation of ATP. The analogous set of transformations, that is, conversion of adipyl-CoA to adipyl-phosphate followed by conversion of adipyl-phosphate to adipate, can be carried out by the buk1, buk2, and ptb gene products. The protein sequences for each of these exemplary gene products can be found using the following GenBank accession numbers:

| ptb | NP_349676 | *Clostridium acetobutylicum* |
| buk1 | NP_349675 | *Clostridium acetobutylicum* |
| buk2 | Q97II1 | *Clostridium acetobutylicum* |

Alternatively, an acetyltransferase capable of transferring the CoA group from adipyl-CoA to acetate can be applied. Similar transformations are catalyzed by the gene products of cat1, cat2, and cat3 of *Clostridium* kluyveri which have been shown to exhibit succinyl-CoA, 4-hydroxybutyryl-CoA, and butyryl-CoA acetyltransferase activity, respectively (Sohling and Gottschalk, *J. Bacteriol.* 178:871-880 (1996); Seedorf et al., *Proc. Natl. Acad. Sci. USA* 105:2128-2133 (2008)). The protein sequences for each of these exemplary gene products can be found using the following GenBank accession numbers:

| cat1 | P38946.1 | *Clostridium kluyveri* |
| cat2 | P38942.2 | *Clostridium kluyveri* |
| cat3 | EDK35586.1 | *Clostridium kluyveri* |

Finally, though not as desirable from an energetic standpoint, the conversion of adipyl-CoA to adipate can also be carried out by an acyl-CoA hydrolase or equivalently a thioesterase. The top *E. coli* gene candidate is tesB (Naggert et al., *J. Biol. Chem.* 266:11044-11050 (1991)), which shows high similarity to the human acot8, which is a dicarboxylic acid acetyltransferase with activity on adipyl-CoA (Westin et al., *J. Biol. Chem.* 280:38125-38132 (2005)). This activity has also been characterized in the rat liver (Deana, *Biochem. Int.* 26:767-773 (1992)). The protein sequences for each of these exemplary gene products can be found using the following GenBank accession numbers:

| tesB | NP_414986 | *Escherichia coli* |
| acot8 | CAA15502 | *Homo sapiens* |
| acot8 | NP_570112 | *Rattus norvegicus* |

Other native candidate genes include tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). The protein sequences for each of these exemplary gene products can be found using the following GenBank accession numbers:

| tesA | NP_415027 | *Escherichia coli* |
| ybgC | NP_415264 | *Escherichia coli* |
| paaI | NP_415914 | *Escherichia coli* |
| ybdB | NP_415129 | *Escherichia coli* |

The above description provides an exemplary adipate synthesis pathway by way of a reverse adipate degradation pathway.

EXAMPLE II

Preparation of an Adipate Producing Microbial Organism Having a Reverse Degradation Pathway This example describes the generation of a microbial organism capable of producing adipate using the reverse degradation pathway.

*Escherichia coli* is used as a target organism to engineer a reverse adipate degradation pathway as shown in FIG. 2. *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in the reverse degradation pathway are expressed in *E. coli* using well known molecular biology techniques (see, for example, Sambrook, supra, 2001; Ausubel supra, 1999). In particular, the paaJ (NP_415915.1), paaH (NP_415913.1), and maoC (NP_415905.1) genes encoding the succinyl-CoA:acetyl- CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. The two sets of plasmids are transformed into E. coli strain MG1655 to express the proteins and enzymes required for adipate synthesis via the reverse degradation pathway.

The resulting genetically engineered organism is cultured in glucose-containing medium following procedures well known in the art (see, for example, Sambrook et al., supra, 2001). The expression of reverse degradation pathway genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., Biotechnol. Bioengineer. 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the adipate producer to further increase production.

For large-scale production of adipate, the above reverse degradation pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., Biotechnol. Bioeng. 775-779 (2005)).

This example describes the preparation of an adipate producing microbial organism using a reverse degradation pathway.

EXAMPLE III

Adipate Synthesis Through 3-Oxoadipate

This example describes an exemplary adipate synthesis pathway through 3-oxoadipate.

Figure 3:
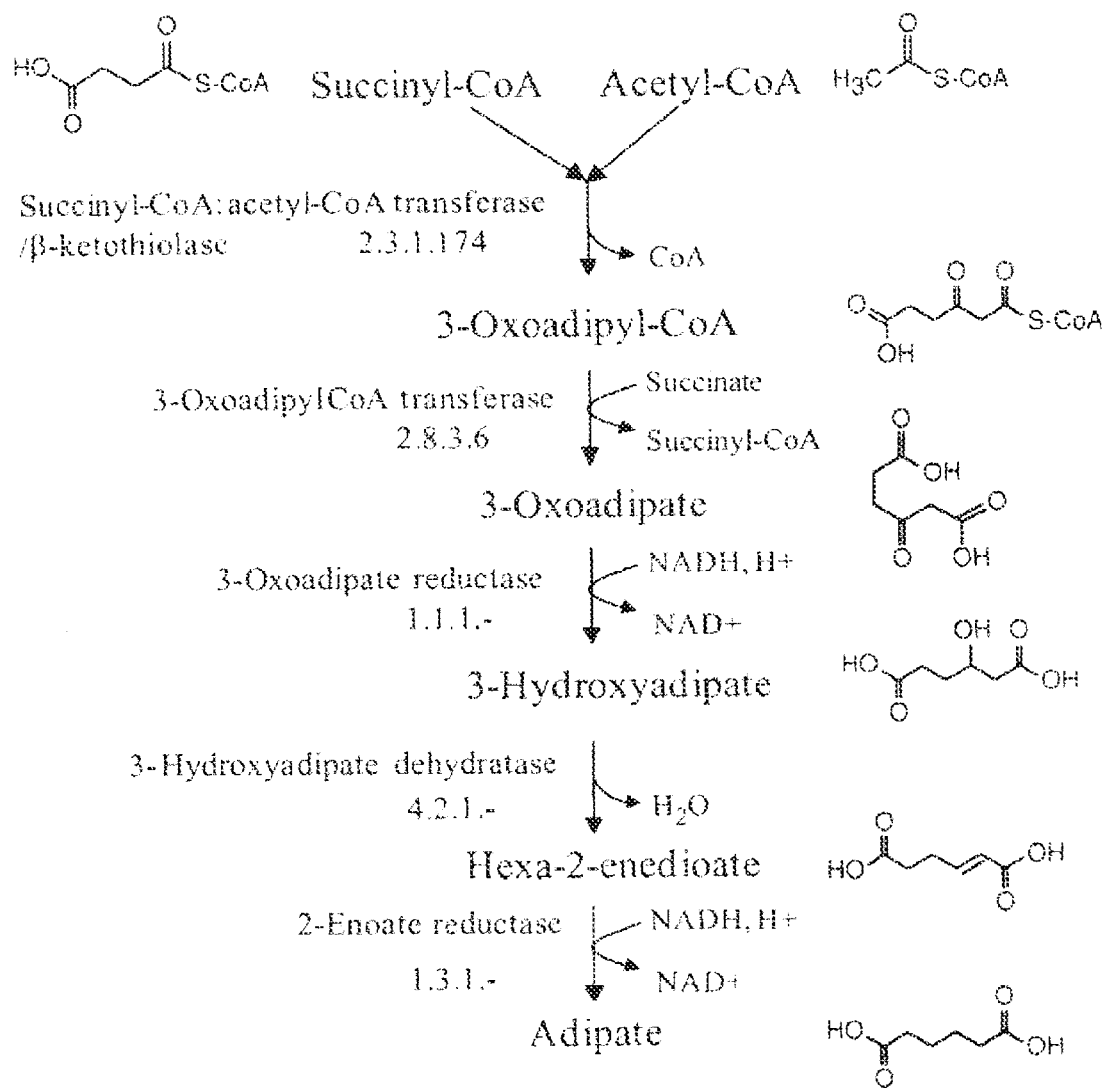
FIG. 3 shows an exemplary pathway for adipate formation via the 3-oxoadipate pathway.

An additional pathway from that described in Examples I and II that uses acetyl-CoA and succinyl-CoA as precursors for adipate formation and passes through the metabolic intermediate, 3-oxoadipate, is shown in FIG. 3. The initial two transformations in this pathway are the two terminal steps of the degradation pathway for aromatic and choloroaromatic compounds operating in the reverse direction (Kaschabek et al., J. Bacteriol. 184:207-215 (2002); Nogales et al., Microbiol. 153:357-365 (2007); Ismail et al., Eur. J. Biochem. 270: 3047-3054 (2003)). Specifically, the first step forms 3-oxoadipyl CoA by the condensation of succinyl- and acetyl-CoA. The second step forms 3-oxoadipate and is reported to be reversible in Pseudomonas sp. Strain B13 (Kaschabek et al., J. Bacteriol. 184:207-215 (2002)).

Figure 4:
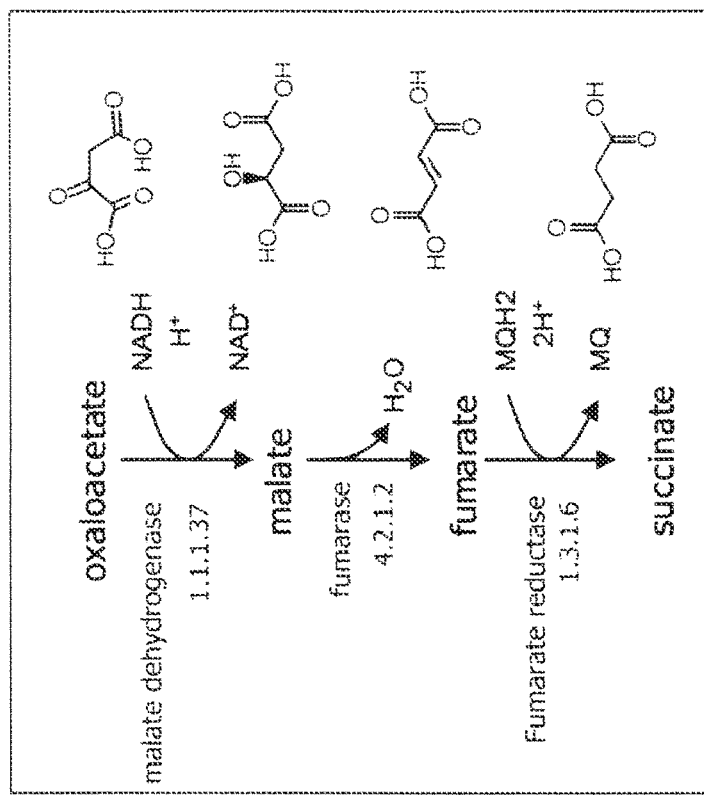
FIG. 4 show the similar enzyme chemistries of the last three steps of the 3-oxoadipate pathway for adipate synthesis and the reductive TCA cycle.
Figure 4:
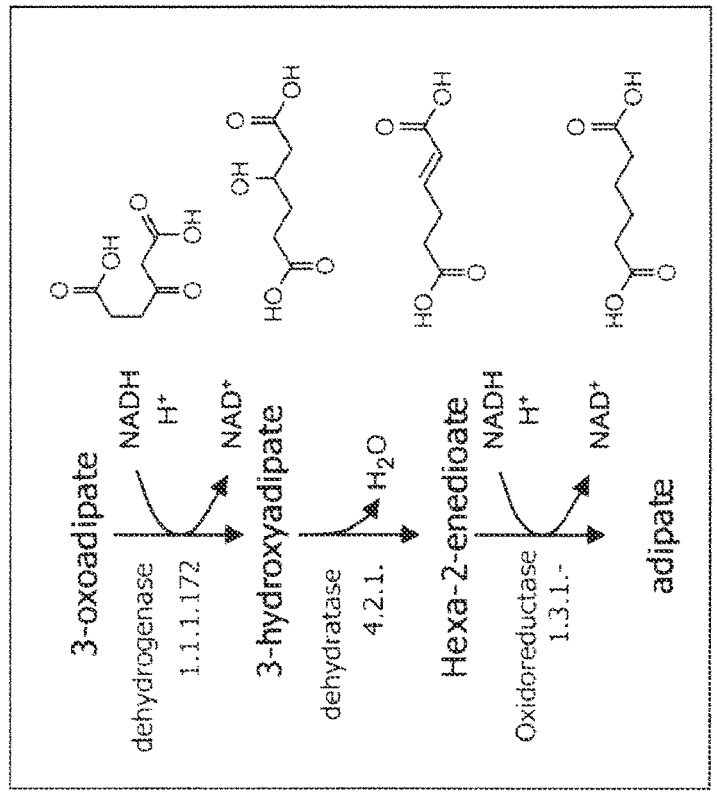

The subsequent steps involve reduction of 3-oxoadipate to 3-hydroxyadipate (conversion of a keto group to hydroxyl group), dehydration of 3-hydroxyadipate to yield hexa-2-enedioate, and reduction of hexa-2-enedioate to form adipate. These steps of the pathway are analogous to the conversion of oxaloacetate into succinate via the reductive TCA cycle (see FIG. 4). This supports the steps in the pathway being thermodynamically favorable subject to the presence of appropriate metabolite concentrations. The final reduction step can be carried out either biochemically or by employing a chemical catalyst to convert hexa-2-enedioate into adipate. Chemical hydrogenation can be performed using Pt catalyst on activated carbon as has been described in (Niu et al., Biotechnol. Prog. 18:201-211 (2002)).

The maximum theoretical yield of adipate using this pathway is 0.92 mole per mole glucose consumed, and oxygen is not required for attaining these yields (see Table 2). The associated energetics are identical to those of the reverse adipate pathway. Theoretically, ATP formation of up to 1.55 moles is observed per mole of glucose utilized through this pathway. The ATP yield improves to approximately 2.47 moles if phosphoenolpyruvate kinase (PPCK) is assumed to operate in the direction of ATP generation. Interestingly, the product yield can be increased further to 1 mole adipate per mole of glucose consumed if chemical hydrogenation is used for the last step and a 100% efficiency of catalysis is assumed. In this scenario, up to 1.95 moles of ATP are formed theoretically without assuming the reverse functionality of PPCK.

TABLE 2

The maximum theoretical yields of adipate and the associated ATP yields per mole of glucose using the 3-oxoadipate pathway.

| | Final step enzymatic | | Final step chemical hydrogenation | |
|---|---|---|---|---|
| | Aerobic | Anaerobic | Aerobic | Anaerobic |
| Adipate Yield | 0.92 | 0.92 | 1.00 | 1.00 |
| Max ATP yield @ max adipate yield | 1.55 | 1.55 | 1.95 | 1.95 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) can be expressed in a host microorganism. In addition, the host microorganism can have endogenous gene(s) functionally deleted. These modifications allow the production of adipate using renewable feedstock.

Described below are a number of biochemically characterized candidate genes capable of encoding enzymes that catalyze each step of the 3-oxoadipate pathway for adipate synthesis. Although this method is described for *E. coli*, one skilled in the art can apply these teachings to any other suitable host organism. Specifically, listed below are genes that are native to *E. coli* as well as genes in other organisms that can be applied to catalyze the appropriate transformations when properly cloned and expressed.

Referring to FIG. 3, step 1 involves succinyl CoA:acetyl CoA acyl transferase (β-ketothiolase). The first step in the pathway combines acetyl-CoA and succinyl-CoA to form 3-oxoadipyl-CoA. The gene products encoded by pcaF in *Pseudomonas* strain B13 (Kaschabek et al., *J. Bacteriol.* 184: 207-215 (2002)), phaD in *Pseudomonas putida* U (Olivera et al., *Proc. Natl. Acad. Sci. USA* 95:6419-6424 (1998)), paaE in *Pseudomonas fluorescens* ST (Di Gennaro et al., *Arch. Microbiol.* 188:117-125 (2007)), and paaJ from *E. coli* (Nogales et al., *Microbiol.* 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the first step in adipate synthesis shown in FIG. 3. For example, the ketothiolase phaA from *R. eutropha* combines two molecules of acetyl-CoA to form acetoacetyl-CoA (Sato et al., *J. Biosci. Bioengineer.* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. The protein sequences for the abovementioned gene products are well known in the art and can be accessed in the public databases such as GenBank using the following accession numbers.

| Gene name | GenBank Accession # | Organism |
|---|---|---|
| paaJ | NP_415915.1 | *Escherichia coli* |
| pcaF | AAL02407 | *Pseudomonas knackmussii* (B13) |

-continued

| Gene name | GenBank Accession # | Organism |
|---|---|---|
| phaD | AAC24332.1 | *Pseudomonas putida* |
| paaE | ABF82237.1 | *Pseudomonas fluorescens* |

These sequences can be used to identify homologue proteins in GenBank or other databases through sequence similarity searches, for example, BLASTp. The resulting homologue proteins and their corresponding gene sequences provide additional exogenous DNA sequences for transformation into *E. coli* or other microorganisms to generate production hosts.

For example, orthologs of paaJ from *Escherichia coli* K12 can be found using the following GenBank accession numbers:

| | |
|---|---|
| YP_001335140.1 | *Klebsiella pneumoniae* |
| YP_001479310.1 | *Serratia proteamaculans* |
| AAC24332.1 | *Pseudomonas putida* |

Example orthologs of pcaF from *Pseudomonas knackmussii* can be found using the following GenBank accession numbers:

| | |
|---|---|
| AAD22035.1 | *Streptomyces* sp. 2065 |
| AAN67000.1 | *Pseudomonas putida* |
| ABJ15177.1 | *Pseudomonas aeruginosa* |

Additional native candidate genes for the ketothiolase step include atoB which can catalyze the reversible condensation of 2 acetyl-CoA molecules (Sato et al., *J. Biosci. Bioengineer.* 103:38-44 (2007)), and its homolog yqeF. Non-native gene candidates include phaA (Sato et al., supra, 2007) and bktB (Slater et al., *J. Bacteriol.* 180:1979-1987 (1998)) from *R. eutropha*, and the two ketothiolases, thiA and thiB, from *Clostridium acetobutylicum* (Winzer et al., *J. Mol. Microbiol. Biotechnol.* 2:531-541 (2000)). The protein sequences for each of these exemplary gene products can be found using the following GenBank accession numbers:

| Gene | Accession | Organism |
|---|---|---|
| atoB | NP_416728.1 | *Escherichia coli* |
| yqeF | NP_417321.2 | *Escherichia coli* |
| phaA | YP_725941 | *Ralstonia eutropha* |
| bktB | AAC38322.1 | *Ralstonia eutropha* |
| thiA | NP_349476.1 | *Clostridium acetobutylicum* |
| thiB | NP_149242.1 | *Clostridium acetobutylicum* |

It is less desirable to use the thiolase-encoding genes fadA and fadB, genes in fatty acid degradation pathway in *E. coli*, in this exemplary pathway. These genes form a complex that encodes for multiple activities, most of which are not desired in this pathway.

Referring to FIG. 3, step 2 involves 3-oxoadipyl-CoA transferase. In this step, 3-oxoadipate is formed by the transfer of the CoA group from 3-oxoadipyl-CoA to succinate. This activity is reported in a two-unit enzyme encoded by pcaI and pcaJ in *Pseudomonas* (Kaschabek et al., *J. Bacteriol.* 184:207-215 (2002)). This enzyme catalyzes a reversible transformation. The protein sequences of exemplary gene products for subunit A of this complex can be found using the following GenBank accession numbers:

| pcaI | AAN69545.1 | *Pseudomonas putida* |
|------|------------|----------------------|
| pcaI | YP_046368.1 | *Acinetobacter* sp. ADP1 |
| pcaI | NP_630776.1 | *Streptomyces coelicolor* |

The protein sequences of exemplary gene products for subunit B of this complex can be found using the following GenBank accession numbers:

| pcaJ | NP_746082.1 | *Pseudomonas putida* |
|------|-------------|----------------------|
| pcaJ | NP_630775.1 | *Streptomyces coelicolor* |
| pcaJ | AAC37147.1 | *Acinetobacter* sp. ADP1 |

Referring to FIG. 3, step 3 involves 3-oxoadipate reductase. *E. coli* has several candidate alcohol dehydrogenases; two that have analogous functions are malate dehydrogenase (mdh) and lactate dehydrogenase (ldhA). While it has not been shown that these two enzymes have broad substrate specificities in *E. coli*, lactate dehydrogenase from Ralstonia eutropha has been shown to demonstrate high activities on substrates of various chain lengths such as lactate, 2-oxobutyrate, 2-oxopentanoate and 2-oxoglutarate (Steinbuchel and Schlegel, *Eur. J. Biochem.* 130:329-334 (1983)). An additional non-native enzyme candidate for this step is the mitochondrial 3-hydroxybutyrate dehydrogenase (bdh) from the human heart which has been cloned and characterized (Marks et al., *J. Biol. Chem.* 267:15459-15463 (1992)). This enzyme is particularly interesting in that it is a dehydrogenase that operates on a 3-hydroxyacid. Given that dehydrogenases are typically reversible, it is expected that this gene product, or a homlog thereof, will be capable of reducing a 3-oxoacid, for example, 3-oxoadipate, to the corresponding 3-hydroxyacid, for example, 3-hydroxyadipate. The protein sequences for each of these exemplary gene products can be found using the following GenBank accession numbers:

| mdh | AAC76268.1 | *Escherichia coli* |
|-----|------------|--------------------|
| ldhA | NP_415898.1 | *Escherichia coli* |
| ldh | YP_725182.1 | *Ralstonia eutropha* |
| bdh | AAA58352.1 | *Homo sapiens* |

Referring to FIG. 3, step 4 involves 3-hydroxyadipate dehydratase. In this reaction, 3-hydroxyadipate is dehydrated to hexa-2-enedioate. Although no direct evidence for this enzymatic transformation has been identified, most dehydratases catalyze the α, β-elimination of water. This involves activation of the α-hydrogen by an electron-withdrawing carbonyl, carboxylate, or CoA-thiol ester group and removal of the hydroxyl group from the β-position (Martins et al., *Proc. Natl. Acad. Sci. USA* 101:15645-15649 (2004); Buckel and Golding, *FEMS Microbiol. Rev.* 22:523-541 (1998)). The protein sequences for exemplary gene products can be found using the following GenBank accession numbers:

| acnA | P25516.3 | *Escherichia coli* |
|------|----------|--------------------|
| fumB | P14407.2 | *Escherichia coli* |
| ilvD | AAA24013.1 | *Escherichia coli* |

Other good candidates for carrying out this function are the serine dehydratases. These enzymes catalyze a very similar transformation in the removal of ammonia from serine as required in this dehydration step. The protein sequence for exemplary gene product can be found using the following GenBank accession number:

| dsdA | P00926 | *Escherichia coli* |
|------|--------|--------------------|

Non-native gene candidates for this transformation have been identified as well. For example, the multi-subunit L-serine dehydratase from *Peptostreptococcus asaccharolyticus* was shown to complement an *E. coli* strain deficient in L-serine dehydratase activity (Hofmeister et al., *J. Bacteriol.* 179:4937-4941 (1997)). Further, a putative 2-(hydroxymethyl)glutarate dehydratase, encoded by the gene hmd in *Eubacterium barkeri* shows similarity to both α- and β-subunits of [4Fe-4S]-containing bacterial serine dehydratases (Alhapel et al., *Proc. Natl. Acad. Sci. USA* 103:12341-12346 (2006)). The protein sequence for exemplary gene product can be found using the following GenBank accession number:

| hmd | ABC88407.1 | *Eubacterium barkeri* |
|-----|------------|------------------------|

Referring to FIG. 3, step 5 involves 2-enoate reductase. The final step in the 3-oxoadipate pathway is reduction of the double bond in hexa-3-enedioate to form adipate. Biochemically, this transformation can be catalyzed by 2-enoate reductase (EC 1.3.1.31) known to catalyze the NADH-dependent reduction of a wide variety of α, β-unsaturated carboxylic acids and aldehydes (Rohdich et al., *J. Biol. Chem.* 276:5779-5787 (2001)). This enzyme is encoded by enr in several species of *Clostridia* (Giesel and Simon, *Arch. Microbiol.* 135:51-57 (1983)) including *C. tyrobutyricum* and *C. thermoaceticum* (now called *Moorella thermoaceticum*) (Rohdich, et al., *J. Biol. Chem.* 276:5779-5787 (2001)). In the recently published genome sequence of *C. kluyveri*, 9 coding sequences for enoate reductases have been reported, out of which one has been characterized (Seedorf et al., *Proc. Natl. Acad. Sci. USA* 105:2128-2133 (2008)). The enr genes from both *C. tyrobutyricum* and *C. thermoaceticum* have been cloned and sequenced and show 59% identity to each other. The former gene is also found to have approximately 75% similarity to the characterized gene in *C. kluyveri* (Giesel and Simon, *Arch. Microbiol.* 135:51-57 (1983)). It has been reported based on these sequence results that enr is very similar to the dienoyl CoA reductase in *E. coli* (fadH) (Rohdich et al., *J. Biol. Chem.* 276:5779-5787 (2001)). Several gene candidates thus exist for catalyzing this last step in the 3-oxoadipate pathway and have been listed below. The *C. thermoaceticum* enr gene has also been expressed in an enzymatically active form in *E. coli* (Rohdich et al., supra, 2001). The protein sequences for exemplary gene products can be found using the following GenBank accession numbers:

| fadH | NP_417552.1 | *Escherichia coli* |
|------|-------------|--------------------|
| enr | ACA54153.1 | *Clostridium botulinum* A3 str |
| enr | CAA71086.1 | *Clostridium tyrobutyricum* |
| enr | CAA76083.1 | *Clostridium kluyveri* |

The above description provides an exemplary adipate synthesis pathway by way of an 3-oxoadipate pathway.

EXAMPLE IV

Preparation of an Adipate Producing Microbial Organism Having a 3-Oxoadipate Pathway This example describes the generation of a microbial organism capable of producing adipate using the 3-oxoadipate pathway.

Escherichia coli is used as a target organism to engineer the 3-oxoadipate pathway as shown in FIG. 3. E. coli provides a good host for generating a non-naturally occurring microorganism capable of producing adipate. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce adipate, nucleic acids encoding the enzymes utilized in the 3-oxoadipate pathway are expressed in E. coli using well known molecular biology techniques (see, for example, Sambrook, supra, 2001; Ausubel supra, 1999). In particular, the paaJ (NP_415915.1), pcaIJ (AAN69545.1 and NP_746082.1), and bdh (AAA58352.1) genes encoding the succinyl-CoA:acetyl-CoA acyl transferase, 3-oxoadipyl-CoA transferase, and 3-oxoadipate reductase activities, respectively, are cloned into the pZE13 vector (Expressys, Ruelzheim, Germany) under the PA1/lacO promoter. In addition, the acnA (P25516.3) and enr (ACA54153.1) genes encoding 3-hydroxyadipate dehydratase and 2-enoate reductase activities, respectively, are cloned into the pZA33 vector (Expressys, Ruelzheim, Germany) under the PA1/lacO promoter. The two sets of plasmids are transformed into E. coli strain MG1655 to express the proteins and enzymes required for adipate synthesis via the 3-oxoadipate pathway.

The resulting genetically engineered organism is cultured in glucose containing medium following procedures well known in the art (see, for example, Sambrook et al., supra, 2001). The expression of the 3-oxoadipate pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., Biotechnol. Bioengineer. 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the adipate producer to further increase production.

For large-scale production of adipate, the 3-oxoadipate pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., Biotechnol. Bioeng. 775-779 (2005)).

This example describes the preparation of an adipate-producing microbial organism containing a 3-oxidoadipate pathway.

EXAMPLE V

Adipate Synthesis Via Cis,Cis-Muconic Acid

This example describes an adipate synthesis pathway previously described (see Niu et al., Biotechnol. Prog. 18(2): p. 201-11. 2002; Frost et al., U.S. Pat. No. 5,487,987, issued Jan. 30, 1996).

Figure 5:
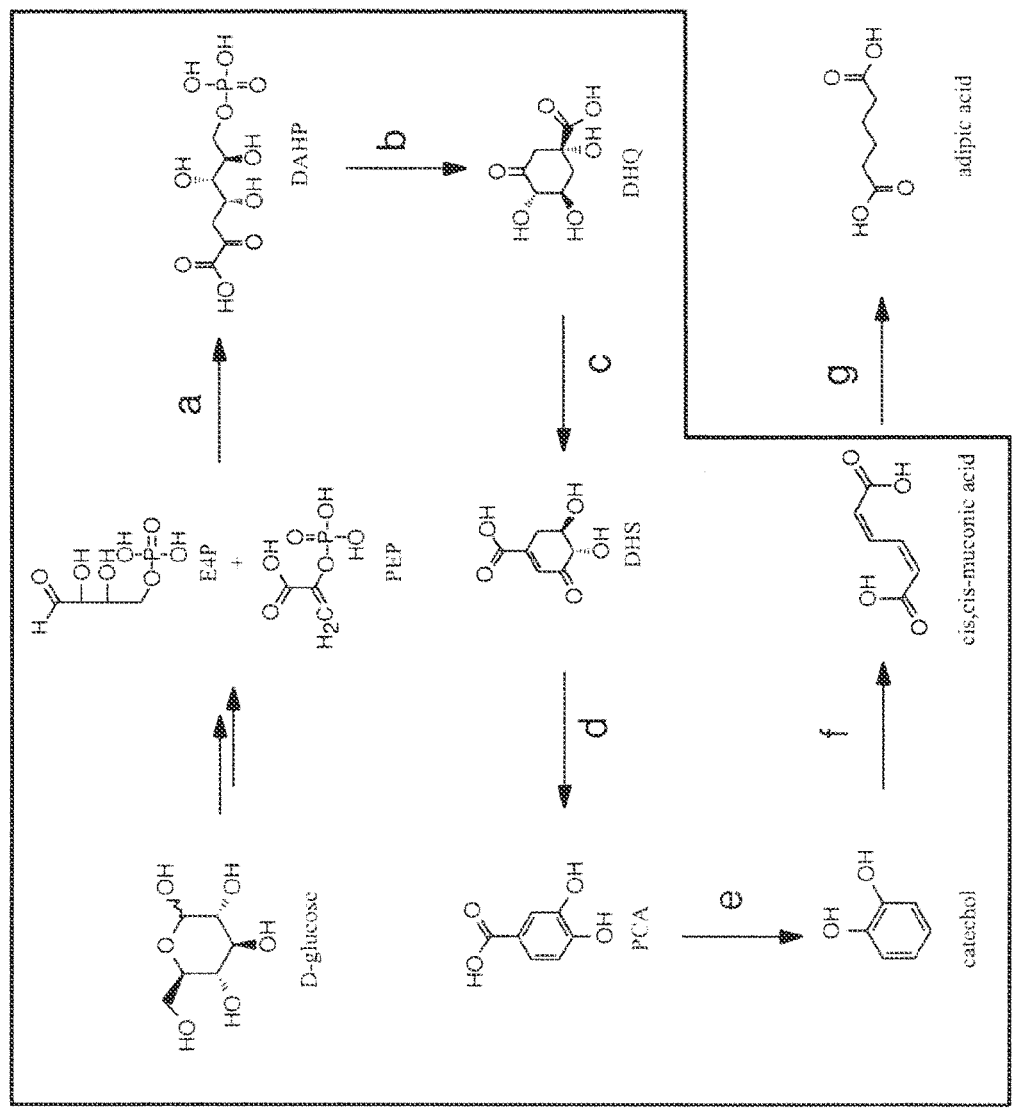
FIG. 5 shows an exemplary pathway for synthesis of adipic acid from glucose via cis,cis-muconic acid. Biosynthetic intermediates (abbreviations): D-erythrose 4-phosphate (E4P), phosphoenolpyruvic acid (PEP), 3-deoxy-D-arabino-heptulosonic acid 7-phosphate (DAHP), 3-dehydroquinic acid (DHQ), 3-dehydroshikimic acid (DHS), protocatechuic acid (PCA). Enzymes (encoding genes) or reaction conditions: (a) DAHP synthase (aroFFBR), (b) 3-dehydroquinate synthase (aroB), (c) 3-dehydroquinate dehydratase (aroD), (d) DHS dehydratase (aroZ), (e) protocatechuate decarboxylase (aroY), (f) catechol 1,2-dioxygenase (catA), (g) 10% Pt/C, $H_2$, 3400 kPa, 25° C. Figure taken from Niu et al., *Biotechnol. Prog.* 18:201-211 (2002)).

Adipate synthesis via a combined biological and chemical conversion process has been previously described. (Niu et al., Biotechnol. Prog. 18:201-211 (2002)) and is shown in FIG. 5. This method is further described in U.S. Pat. No. 5,487,987. Adipate synthesis through this route entails introduction of three heterologous genes into E. coli that can convert dehydroshikimate into cis,cis-muconic acid (Niu et al., supra, 2002). A final chemical hydrogenation step leads to the formation of adipic acid. In this step, the pretreated fermentation broth that contained 150 mM cis,cis-muconate was mixed with 10% platinum (Pt) on activated carbon. The hydrogenation reaction was carried out at 3400 KPa of hydrogen pressure for two and a half hour at 250° C. with stirring. The calculated adipate yields are shown in Table 3 assuming either an enzymatic or chemical catalysis step is utilized to convert cis,cis-muconate into adipate. Under aerobic conditions, an 85% molar yield of adipate can be obtained if a chemical reaction is employed for hydrogenation and a 75% molar yield is obtained if an NADH-based hydrogenase is used.

TABLE 3

The maximum theoretical yields of adipate per mole of glucose using the using the cis,cis-muconic acid pathway.

| | Final step enzymatic | | Final step chemical hydrogenation | |
|---|---|---|---|---|
| | Aerobic | Anaerobic | Aerobic | Anaerobic |
| Adipate Yield | 0.75 | 0.00 | 0.85 | 0.00 |

Although this is an exemplary method, there are disadvantages of this method compared to others, such as those described in Examples I-IV. For example, the first limitation of this method is the lower theoretical yields compared to the reverse adipate degradation and 3-oxoadipate pathways. The second limitation is that the ATP yields of this pathway are negligible. A third limitation of this pathway is that it involves a dioxygenase, necessitating a supply of oxygen to the bioreactor and precluding the option of anaerobic fermentation.

The above description provides an exemplary adipate synthesis pathway by way of a cis,cis-muconic acid pathway

EXAMPLE VI

Adipate Synthesis Via Alpha-Ketoadipate

This example describes an exemplary adipate synthesis pathway via an alpha-ketoadipate pathway.

Alpha-keto adipate is a known intermediate in lysine biosynthesis in *S. cerevisiae*, and this information was used to identify an additional pathway for adipic acid biosynthesis (see FIG. 6). Conversion of alpha-ketoglutarate to alpha-ketoadipate is catalyzed by homocitrate synthase, homoaconitase, and homoisocitrate dehydrogenase as indicated by dashed arrows in FIG. 6. Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977). Subsequent steps involve a dehydratase for the conversion of alpha-hydroxyadipate into hexa-2-enedioate followed by its reduction to adipic acid. This last step can be catalyzed either by an enzyme or can take place through a chemical reaction as described in Example II. Genes encoding the enzymes for the alpha-ketoadipate pathway are identified as described in Examples I-IV.

The adipate yields associated with this pathway are shown in Table 4. Because of the loss of two $CO_2$ molecules during the conversion of acetyl-CoA to adipate, only 67% of the glucose can be converted into adipate. This is reflected in the molar yields for this pathway under aerobic conditions. The yields are further reduced in the absence of oxygen uptake. Also since the maximum ATP yields under anaerobic conditions are negligible, the engineered organism will have to utilize additional substrate to form energy for cell growth and maintenance under such conditions.

TABLE 4

The maximum theoretical yields of adipate and the associated ATP yields per mole of glucose using the using the alpha-ketoadipate pathway.

| | Final step enzymatic | | Final step chemical hydrogenation | |
|---|---|---|---|---|
| | Aerobic | Anaerobic | Aerobic | Anaerobic |
| Adipate Yield | 0.67 | 0.45 | 0.67 | 0.40 |
| Max ATP yield @ max adipate yield | 6.17 | 0.00 | 7.50 | 0.00 |

The above description provides an exemplary adipate synthesis pathway by way of an alpha-ketoadipate pathway.

EXAMPLE VII

Adipate Synthesis Via Lysine Degradation

This example describes an exemplary adipate synthesis pathway via a lysine degradation pathway.

Figure 7:
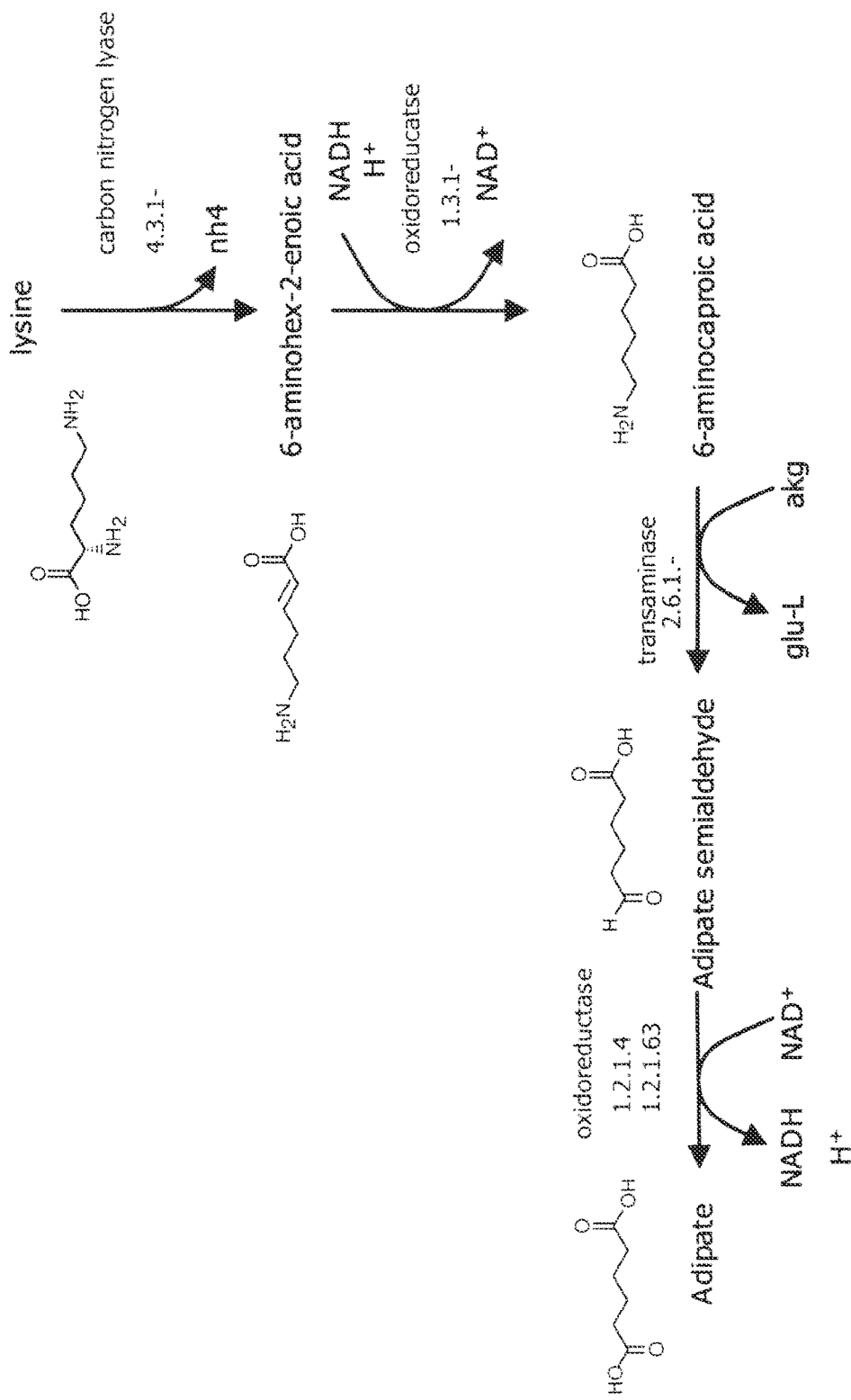
FIG. 7 shows an exemplary pathway for synthesis of adipate using lysine as a starting point.

Two additional pathways for adipate synthesis rely on lysine degradation to form adipate. One pathway starts from alpha-ketoglutarate to form lysine (pathway non-native to *E. coli* and found in *S. cerevisiae*), and the other uses aspartate as a starting point for lysine biosynthesis (pathway native to *E. coli*). FIG. 7 shows adipate formation from lysine. The maximum theoretical yields for adipate, both in the presence and absence of oxygen, using the *E. coli* stoichiometric model are shown in Tables 5 and 6, with alpha-ketoglutarate and aspartate as the respective starting points for lysine. The maximum ATP yields accompanying these theoretical yields were also calculated and are shown in the same tables. These yields are lower in comparison to the other pathways described in Examples I-IV. Genes encoding the enzymes for the alpha-ketoadipate pathway are identified as described in Examples I-IV.

TABLE 5

The maximum theoretical yield of adipate and the accompanying ATP yield per mole of glucose assuming the lysine biosynthesis pathway with alpha-ketoglutarate as a starting point.

| | Aerobic | Anaerobic |
|---|---|---|
| Adipate Yield | 0.40 | 0.20 |
| Max ATP yield @ max adipate yield | 5.60 | 0.00 |

TABLE 6

The maximum theoretical yield of adipate and the accompanying ATP yield per mole of glucose assuming the lysine biosynthesis pathway with aspartate as a starting point.

| | Aerobic | Anaerobic |
|---|---|---|
| Adipate Yield | 0.50 | 0.34 |
| Max ATP yield @ max adipate yield | 0.50 | 0.04 |

The above description provides an exemplary adipate synthesis pathway by way of a lysine degradation pathway.

EXAMPLE VIII

Production of Caprolactam and 6-Aminocaproic Acid Via Adipyl-CoA

This example describes an exemplary caprolactam and/or 6-aminocaproic acid synthesis pathway via an adipyl-CoA pathway.

An exemplary pathway for forming caprolactam and/or 6-aminocaproic acid using adipyl-CoA as the precursor is shown in FIG. 8. The pathway involves a CoA-dependant aldehyde dehydrogenase that can reduce adipyl-CoA to adipate semialdehyde and a transaminase or 6-aminocaproate dehydrogenase that can transform this molecule into 6-aminocaproic acid. The terminal step that converts 6-aminocaproate into caprolactam can be accomplished either via an amidohydrolase or via chemical conversion (Guit and Buijs, U.S. Pat. No. 6,353,100, issued Mar. 7, 2002; Wolters et al., U.S. Pat. No. 5,700,934, issued Dec. 23, 1997; Agterberg et al., U.S. Pat. No. 6,660,857, issued Dec. 9, 2003). The maximum theoretical yield of caprolactam was calculated to be 0.8 mole per mole glucose consumed (see Table 7) assuming that the reverse adipate degradation pathway was complemented with the reaction scheme shown in FIG. 8. The pathway is favorable energetically as up to 0.78 moles of ATP are formed per mole of glucose consumed at the maximum theoretical yield of caprolactam. The ATP yield can be further improved to 1.63 moles of ATP produced per mole of glucose if phosphoenolpyruvate carboxykinase (PPCK) is assumed to function in the ATP-generating direction towards oxaloacetate formation.

The final amidohydrolase step is energetically and redox neutral, and thus the product and ATP molar yields associated with 6-aminocaproic acid production are equivalent to those associated with caprolactam production. Thus one can alternatively envision a microorganism and associated fermentation process that forms 6-aminocaproic acid instead of caprolactam followed by an additional unit operation to dehydrate/cyclize 6-aminocaproic acid to caprolactam.

TABLE 7

The maximum theoretical yield of caprolactam and the accompanying ATP yield per mole of glucose assuming that the reverse fatty acid degradation pathway is complemented with the reaction scheme from FIG. 8.

|  | Aerobic | Anaerobic |
|---|---|---|
| Caprolactam Yield | 0.80 | 0.80 |
| Max ATP yield @ max Caprolactam yield | 0.78 | 0.78 |
| Max ATP yield @ max Caprolactam yield PPCK assumed | 1.63 | 1.63 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of 6-aminocaproic acid or caprolactam, one or more exogenous DNA sequence(s) can be expressed in a host microorganism. In addition, the microorganism can have endogenous gene(s) functionally deleted. These modifications will allow the production of 6-aminocaproate or caprolactam using renewable feedstock.

Below is described a number of biochemically characterized candidate genes capable of encoding enzymes that catalyze each step of the caprolactam formation pathway described in FIG. 8. Although described for *E. coli*, one skilled in the art can apply these teachings to any other suitable host organism. Specifically, the genes listed are native to *E. coli* or are genes in other organisms that can be applied to catalyze the appropriate transformations when properly cloned and expressed.

Referring to FIG. 8, step 1 involves CoA-dependant aldehyde dehydrogenase. Exemplary genes that encode enzymes for catalyzing the reduction of an acyl-coA to its corresponding aldehyde include the *Acinetobacter calcoaceticus* acyl encoding a fatty acyl-CoA reductase (Reiser and Somerville, *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)) and the sucD gene from *Clostridium kluyveri* (Sohling and Gottschalk, *J. Bacteriol.* 178:871-880 (1996)), which can convert succinyl-CoA to succinate semialdehyde.

| Gene name | GenBank Accession # | Organism |
|---|---|---|
| acr1 | YP_047869.1 | *Acinetobacter calcoaceticus* |
|  | BAB85476.1 | *Acinetobacter* sp. Strain M-1 |
| sucD | P38947.1 | *Clostridium kluyveri* |

Referring to FIG. 8, step 2 involves transaminase. The second step in the pathway is conversion of the 6-aldehyde to an amine. This transformation can likely be accomplished by gamma-aminobutyrate transaminase (GABA transaminase), a native enzyme encoded by gabT that transfers an amino group from glutamate to the terminal aldehyde of succinyl semialdehyde (Bartsch et al., *J. Bacteriol.* 172:7035-7042 (1990)). GABA transaminases in *Mus musculus, Pseudomonas fluorescens*, and *Sus scrofa* have been shown to react with 6-aminocaproic acid (Cooper, *Methods Enzymol.* 113:80-82 (1985); Scott and Jakoby, *J. Biol. Chem.* 234:932-936 (1959)). The protein sequences for exemplary gene products can be found using the following GenBank accession numbers:

| gabT | NP_417148.1 | *Escherichia coli* |
|---|---|---|
| abat | NP_766549.2 | *Mus musculus* |
| gabT | YP_257332.1 | *Pseudomonas fluorescens* |
| abat | NP_999428.1 | *Sus scrofa* |

Referring to FIG. 8, step 2 can alternatively involve 6-aminocaproate dehydrogenase which comprises the reductive amination of adipate semialdehyde to form 6-aminocaproate. This transformation can be accomplished by lysine-6-dehydrogenase, which naturally converts L-lysine to 2-aminoadipate-6-semialdehyde. Exemplary enzymes can be found in *Geobacillus stearothermophilus* (Heydari et al., *Appl. Environ. Microbiol.* 70(2):937-942 (2004)), *Agrobacterium tumefaciens* (Hashimoto et al., J. Biochem. (Tokyo), 106(1):76-80 (1989); Misono et al., *J. Biochem.* (Tokyo), 105(6):1002-1008 (1989)), and *Achromobacter denitrificans* (Ruldeekulthamrong et al., *BMB Reports* 790-795 (2008)).

| lysDH | BAB39707 | *Geobacillus stearothermophilus* |
|---|---|---|
| lysDH | NP_353966 | *Agrobacterium tumefaciens* |
| lysDH | AAZ94428 | *Achromobacter denitrificans* |

Referring to FIG. 8, step 3 involves amidohydrolase. The final step of caprolactam synthesis is cyclization of 6-aminocaproic acid. This transformation has not been characterized enzymatically but it is very similar to the cyclization of lysine by D-lysine lactamase (EC 3.5.2.11) from *Cryptococcus laurentii* (Fukumura et al., *FEBS Lett.* 89:298-300 (1978)). However, the protein and nucleotide sequences of this enzyme are not currently known and, so far, lysine lactamase activity has not been demonstrated in other organisms.

Plasmids contained in several strains of *Pseudomonas* sp. isolated from soil have been shown to confer ability to grow on caprolactam as a sole carbon source (Boronin et al., *FEMS Microbiol. Lett.* 22:167-170 (1984)); however, associated gene or protein sequences have not been associated with this function to date.

The most closely related candidate enzyme with available sequence information is 6-aminohexanoate-cyclic dimer hydrolase, which has been characterized in *Pseudomonas* sp. and *Flavobacterium* sp. The nylB gene product from *Pseudomonas* sp NK87 was cloned and expressed in *E. coli* (Kanagawa et al., *J. Gen. Microbiol.* 139:787-795 (1993)). The substrate specificity of the enzyme was tested in *Flavobacterium* sp K172 and was shown to react with higher-order oligomers of 6-aminohexanoate but not caprolactam (Kinoshita et al., *Eur. J. Biochem.* 116:547-551 (1981)). The reversibility and ability of 6-aminohexanoate dimer hydrolases in other organisms to react with the desired substrate in the direction of interest can be further tested. The protein sequences for exemplary gene products can be found using the following GenBank accession numbers:

| nylB | AAA24929.1 | *Pseudomonas* sp NK87 |
| nylB | P13397 | *Flavobacterium* sp K172 |
| nylB | YP_949627.1 | *Arthrobacter aurescens* TC1 |

The above description provides an exemplary pathway to produce caprolactam and/or 6-aminocaproic acid by way of an adipyl-CoA pathway.

EXAMPLE IX

Preparation of a 6-Aminocaproate or Caprolactam Producing Microbial Organism Having a 3-Oxoadipate Pathway This example describes the generation of a microbial organism capable of producing adipate using the reverse degradation pathway and converting the intracellular adipate to 6-aminocaproate and/or caprolactam.

*Escherichia coli* is used as a target organism to engineer the necessary genes for adipate, 6-aminocaproate, and/or caprolactam synthesis (see FIG. 2 and FIG. 8). *E. coli* provides a good host for generating a non-naturally occurring microorganism capable of producing adipate, 6-aminocaproate, and/or caprolactam. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 6-aminocaproate and/or caprolactam, nucleic acids encoding the enzymes utilized in the reverse adipate degradation pathway and 6-aminocaproate or caprolactam synthesis pathways are expressed in *E. coli* using well known molecular biology techniques (see, for example, Sambrook, supra, 2001; Ausubel, supra, 1999). In particular, the paaJ (NP_415915.1), paaH (NP_415913.1), and maoC (NP_415905.1) genes encoding the succinyl-CoA:acetyl-CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. Lastly, the acyl (YP_047869.1), gabT (NP_417148.1), and nylB (AAA24929.1) genes encoding CoA-dependent aldehyde dehydrogenase, transaminase, and amidohydrolase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for 6-aminocaproate and/or caprolactam synthesis.

The resulting genetically engineered organism is cultured in glucose containing medium following procedures well known in the art (see, for example, Sambrook et al., supra, 2001). The expression of the 6-aminocaproate and caprolactam synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce 6-aminocaproate and/or caprolactam is confirmed using HPLC, gas chromatography-mass spectrometry (GCMS) and/or liquid chromatography-mass spectrometry (LCMS).

Microbial strains engineered to have a functional pathway for the synthesis of 6-aminocaproate and/or caprolactam are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproate and/or caprolactam. One modeling method is the bilevel optimization approach, OptKnock (Burgard et al., *Biotechnol. Bioengineer.* 84:647-657 (2003)), which is applied to select gene knockouts that collectively result in better production of 6-aminocaproate and/or caprolactam. Adaptive evolution also can be used to generate better producers of, for example, the acetyl-CoA and succinyl-CoA intermediates of the products. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 6-aminocaproate and/or caprolactam producer to further increase production.

For large-scale production of 6-aminocaproate and/or caprolactam, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

EXAMPLE X

Adipate Synthesis Via 2-Hydroxyadipyl-CoA

This example describes two exemplary adipate synthesis pathways proceeding from alpha-ketoadipate and passing through a 2-hydroxyadipyl-CoA intermediate.

As described in example VI, alpha-ketoadipate is a known intermediate in lysine biosynthesis that can be formed from alpha-ketoglutarate via homocitrate synthase, homoaconitase, and homoisocitrate dehydrogenase. Alpha-ketoadipate can be converted to 2-hydroxyadipyl-CoA by the two routes depicted in FIG. 9. 2-hydroxyadipyl-CoA can be subsequently dehydrated and reduced to adipyl-CoA which can then be converted to adipate as shown in FIG. 9. The maximum yield of adipate from glucose via these pathways is 0.67 mol/mol.

Conversion of alpha-ketoadipate into 2-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977). Alternatively, enzymes capable of reducing alpha-ketoglutarate to 2-hydroxyglutarate may also show activity on alpha-ketoadipate, which is only one carbon atom longer. One such enzyme possessing alpha-ketoglutarate reductase activity is serA of *Escherichia coli* (Zhao and Winkler, *J. Bacteriol.* 178(1): 232-9 (1996)). Additional exemplary enzymes can be found in *Arabidopsis thaliana* (Ho, et al., *J. Biol. Chem.* 274(1):397-402 (1999)) and *Haemophilus influenzae*.

| serA | NP_417388.1 | *Escherichia coli* |
| PGDH | NP_564034 | *Arabidopsis thaliana* |
| serA | P43885 | *Haemophilus influenzae* |

Referring to FIG. 9, 2-hydroxyadipate can likely be converted to 2-hydroxyadipyl-CoA by the synthetases, transferases, phosphotransadipylases and kinases described in example I. Alternatively, enzymes with 2-hydroxyglutarate CoA-transferase or glutaconate CoA-transferase activity are likely suitable to transfer a CoA moiety to 2-hydroxyadipate.

One example of such an enzyme is encoded by the gctA and gctB genes of *Acidaminococcus fermentans* (Buckel, et al., *Eur. J. Biochem.* 118(2):315-321 (1981); Mack, et al., *Eur. J. Biochem.* 226(1):41-51 (1994)). Similarly, synthetase, transferase, or phosphotransadipylase and kinase activities would be required to convert alpha-ketoadipate into alpha-ketoadipyl-CoA, as depicted in FIG. 9. Conversion of alpha-ketoadipyl-CoA to 2-hydroxyadipyl-CoA can be carried out by an alpha-hydroxyacyl-CoA dehydrogenase enzyme. A similar activity was reported in propionate-adapted *E. coli* cells whose extracts catalyzed the oxidation of lactyl-CoA to form pyruvyl-CoA (Megraw et al., *J. Bacteriol.* 90(4): 984-988 (1965)). Additional hydroxyacyl-CoA dehydrogenases were described in example I.

| gctA | Q59111 | *Acidaminococcus fermentans* |
| gctB | Q59112 | *Acidaminococcus fermentans* |

The dehydration of 2-hydroxyadipyl-CoA to form 5-carboxy-2-pentenoyl-CoA can be carried out by a 2-hydroxyacyl-CoA dehydratase. A 2-hydroxyglutaryl-CoA dehydratase system has been characterized in *Acidaminococcus fermentans* and requires both the hgdA and hgdB subunits and the activator protein, hgdC, for optimal activity (Dutscho et al., *Eur. J. Biochem.* 181(3):741-746 (1989); Locher et al. *J. Mol. Biol.* 307(1):297-308; Muller and Buckel, *Eur. J. Biochem.* 230(2):698-704 (2001); Schweiger et al. *Eur. J. Biochem.* 169(2):441-448 (1987)). This enzyme system is similar in mechanism to the lactoyl-CoA dehydratase from *Clostridium propionicum* (Hofmeister and Buckel, *Eur. J. Biochem.* 206 (2):547-552 (1992); Kuchta and Abeles, *J. Biol. Chem.* 260 (24):13181-13189 (1985)). Homologs to hgdA, hgdB, and hgdC exist in several organisms.

| hgdA | P11569 | *Acidaminococcus fermentans* |
| hgdB | P11570 | *Acidaminococcus fermentans* |
| hgdC | P11568 | *Acidaminococcus fermentans* |
| hgdA | ZP_03731126.1 | *Clostridium* sp. M62/1 |
| hgdB | ZP_03731125.1 | *Clostridium* sp. M62/1 |
| hgdC | ZP_03731127.1 | *Clostridium* sp. M62/1 |
| hgdA | NP_603114.1 | *Fusobacterium nucleatum* ATCC 25586 |
| hgdB | NP_603115.1 | *Fusobacterium nucleatum* ATCC 25586 |
| hgdC | NP_603113.1 | *Fusobacterium nucleatum* ATCC 25586 |

Conversion of 5-carboxy-2-pentenoyl-CoA to adipate is carried out by the enzymes described in Example I.

The above description provides an exemplary adipate synthesis pathway by way of a 2-hydroxyadipyl-CoA pathway.

EXAMPLE XI

Preparation of an Adipate Producing Microbial Organism Having a 2-Hydroxyadipyl-CoA Pathway This example describes the generation of a microbial organism capable of producing adipate using a 2-hydroxyadipyl-CoA pathway.

*Escherichia coli* is used as a target organism to engineer the necessary genes for adipate synthesis (see FIG. 9). *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in a 2-hydroxyadipyl-CoA to adipate pathway are expressed in *E. coli* using well known molecular biology techniques (see, for example, Sambrook, supra, 2001; Ausubel, supra, 1999). In particular, the serA (NP_417388.1), gctA (Q59111), and gctB (Q59112) genes encoding the 2-hydroxyadipate dehydrogenase and 2-hydroxyadipyl-CoA:acetyl-CoA transferase activities, respectively, are cloned into the pZE13 vector (Expressys, Ruelzheim, Germany) under the PA1/lacO promoter. In addition, the hgdA (P11569), hgdB (P11570), and hgdC (P11568) genes encoding 2-hydroxyadipyl-CoA dehydratase activity, respectively, are cloned into the pZA33 vector (Expressys, Ruelzheim, Germany) under the PA1/lacO promoter. Further, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for adipate synthesis.

The resulting genetically engineered organism is cultured in glucose containing medium following procedures well known in the art (see, for example, Sambrook et al., supra, 2001). The expression of the 2-hydroxyadipyl-CoA pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the alpha-ketoadipate intermediate or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the 2-hydroxyadipyl-CoA pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

This example describes the preparation of an adipate-producing microbial organism containing a 2-hydroxyadipyl-CoA pathway.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for producing adipyl-CoA, comprising culturing a host microbial organism in which at least one exogenous nucleic acid is introduced under conditions and for a sufficient period of time to produce adipyl-CoA, wherein said host microbial organism comprises at least one exogenous nucleic acid encoding a set of adipyl-CoA pathway enzymes that are expressed in a sufficient amount to produce adipvl-CoA, wherein said set of adipyl-CoA pathway enzymes convert succinyl-CoA and acetyl-CoA to 3-oxoadipyl-CoA, 3-oxoadipyl-CoA to 3-hydroxyadipyl-CoA, 3-hydroxyadipyl-CoA to 5-carboxy-2pentenoyl-CoA and 5-carboxy-2-pentenoyl-CoA to adipyl-CoA.

2. The method of claim 1, wherein said host microbial organism is in a substantially anaerobic culture medium.

3. The method of claim 1, wherein said at least one exogenous nucleic acid is a heterologous nucleic acid.

4. The method of claim 1, wherein said set of adipyl-CoA pathway enzymes comprise a succinyl-CoA:acetyl-CoA acyl transferase, a 3-hydroxyacyl-CoA dehydrogenase, a 3-hydroxyadipyl-CoA dehydratase and a 5-carboxy-2-pentenoyl-CoA reductase.

5. A method for producing adipate, comprising culturing a host microbial organism in which at least one exogenous nucleic acid is introduced under conditions and for a sufficient period of time to produce adipate, wherein said host microbial organism comprises at least one exogenous nucleic acid encoding a set of adipyl-CoA pathway enzymes that are expressed in a sufficient amount to produce adipyl-CoA, wherein said set of adipyl-CoA pathway enzymes convert succinyl-CoA and acetyl-CoA to 3-oxoadipyl-CoA, 3-oxoadipyl-CoA to 3-hydroxyadipyl-CoA, 3-hydroxyadipyl-CoA to 5-carboxy-2-pentenoyl-CoA and 5-carboxy-2-pentenoyl-CoA to adipyl-CoA, and wherein said host microbial organism comprises at least one exogenous nucleic acid encoding an adipate pathway enzyme expressed in a sufficient amount to produce adipate, wherein said adipate pathway enzyme is selected from the group consisting of an adipyl-CoA synthetase, a phosphotransadipylase/adipate kinase, an adipyl-CoA:acetyl-CoA transferase and an adipyl-CoA hydrolase.

6. The method of claim 5, wherein said host microbial organism is in a substantially anaerobic culture medium.

7. The method of claim 5, wherein said at least one exogenous nucleic acid is a heterologous nucleic acid.

8. The method of claim 5, wherein said at least one exogenous nucleic acid encoding an adipate pathway enzyme encodes a set of adipate pathway enzymes that are expressed in a sufficient amount to produce adipate, said set of adipate pathway enzymes comprising an adipyl-CoA synthetase, a phosphotransadipylase/adipate kinase, an adipyl-CoA:acetyl-CoA transferase and an adipyl-CoA hydrolase.

9. A method for producing adipate, comprising culturing a host microbial organism in which at least one exogenous nucleic acid is introduced under conditions and for a sufficient period of time to produce adipate, wherein said host microbial organism comprises at least one exogenous nucleic acid encoding a set of adipyl-CoA pathway enzymes that are expressed in a sufficient amount to produce adipyl-CoA, wherein said set of adipyl-CoA pathway enzymes convert succinyl-CoA and acetyl-CoA to 3-oxoadipyl-CoA, 3-oxoadipyl-CoA to 3-hydroxyadipyl-CoA, 3-hydroxyadipyl-CoA to 5-carboxy-2-pentenoyl-CoA and 5-carboxy-2-pentenoyl-CoA to adipyl-CoA, and wherein said host microbial organism comprises at least one exogenous nucleic acid encoding an adipate pathway enzyme expressed in a sufficient amount to produce adipate, wherein said adipate pathway enzyme is selected from the group consisting of a succinyl-CoA:acetyl-CoA acyl transferase, a 3-oxoadipyl-CoA transferase, a 3-oxoadipate reductase, a 3-hydroxyadipate dehydratase, and a 2-enoate reductase.

10. The method of claim 9, wherein said host microbial organism is in a substantially anaerobic culture medium.

11. The method of claim 9, wherein said at least one exogenous nucleic acid is a heterologous nucleic acid.

12. The method of claim 9, wherein said at least one exogenous nucleic acid encoding an adipate pathway enzyme encodes a set of adipate pathway enzymes that are expressed in a sufficient amount to produce adipate, said set of adipate pathway enzymes comprising a succinyl-CoA:acetyl-CoA acyl transferase, a 3-oxoadipyl-CoA transferase, a 3-oxoadipate reductase, a 3-hydroxyadipate dehydratase, and a 2-enoate reductase.

* * * * *